(12) United States Patent
Parham et al.

(10) Patent No.: US 12,193,325 B2
(45) Date of Patent: Jan. 7, 2025

(54) NITROGEN-CONTAINING HETEROCYCLES FOR USE IN OLEDS

(71) Applicant: Merck Patent GmbH, Darmstadt (DE)

(72) Inventors: Amir Parham, Frankfurt am Main (DE); Jonas Kroeber, Frankfurt am Main (DE); Dominik Joosten, Frankfurt am Main (DE); Aurélie Ludemann, Frankfurt am Main (DE); Tobias Grossmann, Darmstadt (DE); Philipp Stoessel, Frankfurt am Main (DE); Christian Eickhoff, Mannheim (DE)

(73) Assignee: MERCK PATENT GMBH (DE)

( * ) Notice: Subject to any disclaimer, the term of this patent is extended or adjusted under 35 U.S.C. 154(b) by 0 days.

(21) Appl. No.: 16/466,655

(22) PCT Filed: Dec. 4, 2017

(86) PCT No.: PCT/EP2017/081292
§ 371 (c)(1),
(2) Date: Jun. 5, 2019

(87) PCT Pub. No.: WO2018/104195
PCT Pub. Date: Jun. 14, 2018

(65) Prior Publication Data
US 2020/0066994 A1    Feb. 27, 2020

(30) Foreign Application Priority Data

Dec. 5, 2016 (EP) .................................... 16202147

(51) Int. Cl.
| | |
|---|---|
| *H10K 85/60* | (2023.01) |
| *C07D 403/04* | (2006.01) |
| *C07D 403/14* | (2006.01) |
| *C07D 471/06* | (2006.01) |
| *C07D 471/16* | (2006.01) |
| *C07D 491/06* | (2006.01) |
| *C07D 491/16* | (2006.01) |
| *C07D 495/06* | (2006.01) |
| *C07D 495/16* | (2006.01) |
| *C07D 495/22* | (2006.01) |
| *C07D 519/00* | (2006.01) |
| *C09K 11/06* | (2006.01) |
| *H10K 50/11* | (2023.01) |
| *H10K 101/10* | (2023.01) |

(52) U.S. Cl.
CPC ......... *H10K 85/657* (2023.02); *C07D 403/04* (2013.01); *C07D 403/14* (2013.01); *C07D 471/06* (2013.01); *C07D 471/16* (2013.01); *C07D 491/06* (2013.01); *C07D 491/16* (2013.01); *C07D 495/06* (2013.01); *C07D 495/16* (2013.01); *C07D 495/22* (2013.01); *C07D 519/00* (2013.01); *C09K 11/06* (2013.01); *H10K 85/6572* (2023.02); *H10K 85/6574* (2023.02); *C09K 2211/1018* (2013.01); *H10K 50/11* (2023.02); *H10K 2101/10* (2023.02)

(58) Field of Classification Search
CPC .................................................. H01L 51/0071
See application file for complete search history.

(56) References Cited

U.S. PATENT DOCUMENTS

| | | | |
|---|---|---|---|
| 2017/0077416 A1 | 3/2017 | Kim et al. | |
| 2017/0213984 A1* | 7/2017 | Kim | ............ H01L 51/0054 |
| 2019/0006601 A1* | 1/2019 | Nishimae | ............ C07D 491/06 |
| 2019/0173022 A1 | 6/2019 | Kim et al. | |

FOREIGN PATENT DOCUMENTS

| | | |
|---|---|---|
| CN | 106661037 A | 5/2017 |
| CN | 108699058 A | 10/2018 |
| EP | 3305792 A1 | 4/2018 |
| JP | 2016-535735 | 11/2016 |
| JP | 2017-538657 A | 12/2017 |
| JP | 2018-516850 A | 6/2018 |
| KR | 20150111106 A | 10/2015 |
| KR | 10-2016-0029662 | 3/2016 |
| KR | 20160056521 A | 5/2016 |
| KR | 10-2016-0111345 | 9/2016 |
| KR | 10-2017-0063394 | 6/2017 |
| KR | 1020170116983 | * 10/2017 |
| KR | 10-2017-0120767 | 11/2017 |
| TW | 201708228 A | 3/2017 |
| WO | 2015/122711 A1 | 8/2015 |
| WO | WO-2016006791 A1 | 1/2016 |
| WO | WO-2016195441 A1 | 12/2016 |
| WO | WO-2017109722 A1 | 6/2017 |
| WO | WO-2017109727 A1 | 6/2017 |
| WO | 2018/034242 | 6/2019 |

OTHER PUBLICATIONS

International Search Report for PCT/EP2017/081292 mailed Jan. 22, 2018.
Written Opinion of the International Searching Authority for PCT/EP2017/081292 mailed Jan. 22, 2018.
International Preliminary Report on Patentability received for PCT Patent Application No. PCT/EP2017/081292, mailed on Jun. 20, 2019, 20 pages (12 pages of English Translation and 8 pages of Original Document).

* cited by examiner

*Primary Examiner* — William D Young
(74) *Attorney, Agent, or Firm* — Faegre Drinker Biddle & Reath LLP

(57) ABSTRACT

The present invention describes nitrogen-containing heterocycles substituted by carbazole groups, especially for use in electronic devices. The invention further relates to a process for preparing the compounds of the invention and to electronic devices comprising these.

13 Claims, No Drawings

NITROGEN-CONTAINING HETEROCYCLES FOR USE IN OLEDS

CROSS-REFERENCE TO RELATED APPLICATIONS

This application is a national stage application (under 35 U.S.C. § 371) of PCT/EP2017/081292, filed Dec. 4, 2017, which claims benefit of European Application No. 16202147.1, filed Dec. 5, 2016, both of which are incorporated herein by reference in their entirety.

The present invention describes nitrogen-containing heterocycles substituted by carbazole groups, especially for use in electronic devices. The invention further relates to a process for preparing the compounds of the invention and to electronic devices comprising these compounds.

Emitting materials used in organic electroluminescent devices (OLEDs) are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime. The properties of organic electroluminescent devices are not only determined by the emitters used. Also of particular significance here are especially the other materials used, such as host/matrix materials, hole blocker materials, electron transport materials, hole transport materials and electron or exciton blocker materials. Improvements to these materials can lead to distinct improvements to electroluminescent devices.

Frequently used according to the prior art as matrix materials for phosphorescent compounds and as electron transport materials are heteroaromatic compounds, for example quinazoline derivatives. In addition, carbazole derivatives are also used as matrix materials, and there are also known compounds having both carbazole structures and structures derived from quinazolines.

In general terms, in the case of these materials, for example for use as matrix materials, hole transport materials or electron transport materials, there is still a need for improvement, particularly in relation to the lifetime, but also in relation to the efficiency and operating voltage of the device.

The problem addressed by the present invention is therefore that of providing compounds which are suitable for use in an organic electronic device, especially in an organic electroluminescent device, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials, the hole conductor materials or the electron transport materials too have an essential influence on the lifetime and efficiency of the organic electroluminescent device.

A further problem addressed by the present invention can be considered that of providing compounds suitable for use in a phosphorescent or fluorescent OLED, especially as a matrix material. More particularly, a problem addressed by the present invention is that of providing matrix materials suitable for red-, yellow- and green-phosphorescing OLEDs.

In addition, the compounds, especially when they are used as matrix materials, as hole conductor materials or as electron transport materials in organic electroluminescent devices, should lead to devices having excellent colour purity.

Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. The present invention therefore provides these compounds and electronic devices, especially organic electroluminescent devices, containing such compounds, and the corresponding preferred embodiments.

The present invention therefore provides a compound comprising at least one structure of the following formula (I):

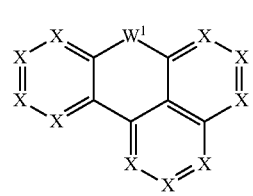

Formula (I)

where the symbols used are as follows:

X is the same or different at each instance and is N or $CR^1$ or C-(CAB);

$W^1$ is O, S, SO, $SO_2$, $Si(R^1)_2$ or C=O, preferably O, S, SO, $SO_2$ or C=O, more preferably O, S or C=O, most preferably O or S;

$R^1$ is the same or different at each instance and is H, D, F, Cl, Br, I, CN, $NO_2$, $N(Ar^1)_2$, $N(R^2)_2$, $OAr^1$, $OR^2$, $SAr^1$, $SR^1$, C(=O)$Ar^1$, C(=O)$R^2$, P(=O)$(Ar^1)_2$, $P(Ar^1)_2$, $B(Ar^1)_2$, $Si(Ar^1)_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, and where one or more nonadjacent $CH_2$ groups may be replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 40 aromatic ring atoms, and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a combination of these systems; at the same time, two or more preferably adjacent R¹ substituents together may also form a mono- or polycyclic, aliphatic, heteroaliphatic, aromatic or heteroaromatic ring system;

Ar¹ is the same or different at each instance and is an aromatic or heteroaromatic ring system which has 5 to 30 aromatic ring atoms and may be substituted by one or more nonaromatic R² radicals; at the same time, it is possible for two Ar¹ radicals bonded to the same silicon atom, nitrogen atom, phosphorus atom or boron atom also to be joined together via a bridge by a single bond or a bridge selected from B(R²), C(R²)₂, Si(R²)₂, C=O, C=NR², C=C(R²)₂, O, S, S=O, SO₂, N(R²), P(R²) and P(=O)R²;

R² is the same or different at each instance and is H, D, F, Cl, Br, I, CN, B(OR³)₂, OR³, SR³, NO₂, C(=O)R³, CR³=C(R³)₂, C(=O)OR³, C(=O)N(R³)₂, Si(R³)₃, P(R³)₂, B(R¹³)₂, N(R³)₂, NO₂, P(=O)(R³)₂, OSO₂R³, OR³, S(=O)R³, S(=O)₂R³, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R³ radicals, and where one or more nonadjacent CH₂ groups may be replaced by —R³C=CR³—, —C≡C—, Si(R³)₂, C=O, C=S, C=NR³, —C(=O)O—, —C(=O)NR³—, NR³, P(=O)(R³), —O—, —S—, SO or SO₂ and where one or more hydrogen atoms may be replaced by D, F, Cl, Br, I, CN or NO₂, or an aromatic or heteroaromatic ring system which has 5 to 40 aromatic ring atoms and may be substituted in each case by one or more R³ radicals, or an aryloxy or heteroaryloxy group which has 5 to 40 aromatic ring atoms and may be substituted by one or more R³ radicals, or a combination of these systems; at the same time, two or more preferably adjacent R² substituents together may also form a mono- or polycyclic, aliphatic, heteroaliphatic, aromatic or heteroaromatic ring system;

R³ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more preferably adjacent R³ substituents together to form a mono- or polycyclic, aliphatic ring system;

with the proviso that at least one X group is N which is adjacent to a group in which X is C-(CAB) in which CAB is a group of the formula (CAB-1)

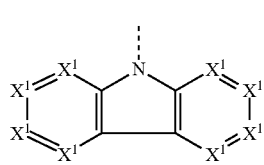

Formula (CAB-1)

in which X¹ is the same or different at each instance and is CR¹ or N and the dotted line represents the bond to the carbon atom of the aromatic ring to which the group of the formula (CAB-1) is bonded.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

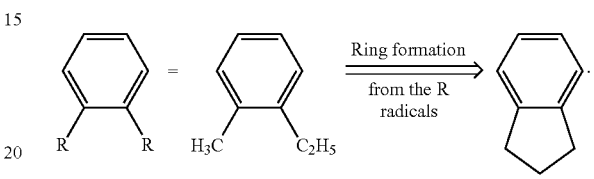

In addition, however, the abovementioned wording shall also be understood to mean that, if one of the two radicals is hydrogen, the second radical is bonded to the position to which the hydrogen atom was bonded, forming a ring. This shall be illustrated by the following scheme:

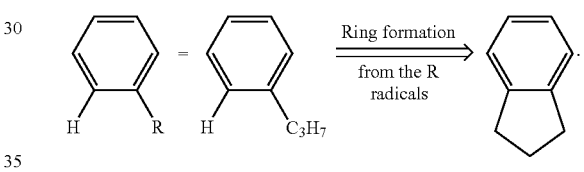

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, exactly one X group is (C-CAB).

In a preferred configuration, the compounds of the invention may comprise at least one structure of the formula (IIa), (IIb), (IIc) or (IId)

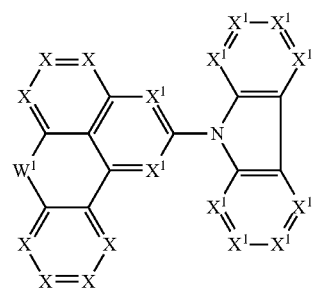

Formula (IIa)

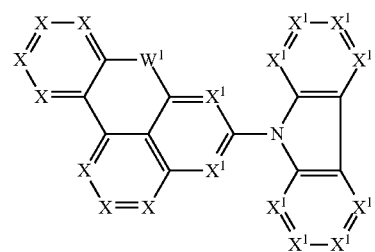

Formula (IIb)

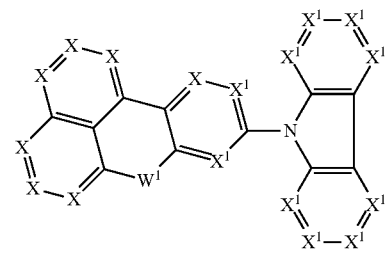

Formula (IIc)

-continued

Formula (IId)

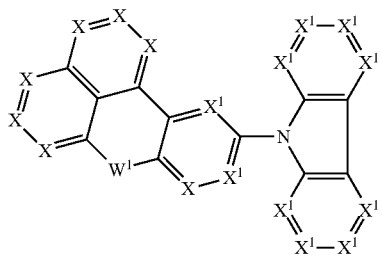

where the symbols $W^1$ and X used have the definition given above, especially for formula (I), and $X^1$ is the same or different and is N or $CR^1$, where at least one $X^1$ group adjacent to the carbon atom to which the (aza)carbazole group is bonded is N. X here is preferably the same or different and is $CR^1$ or N, more preferably $CR^1$.

Preferably, the compounds of the invention may comprise at least one structure of the formula (IIIa), (IIIb), (IIIc) or (IIId)

Formula (IIIa)

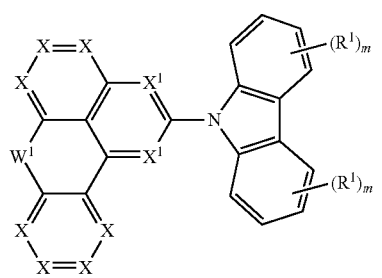

Formula (IIIb)

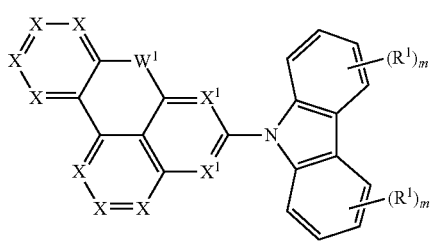

Formula (IIIc)

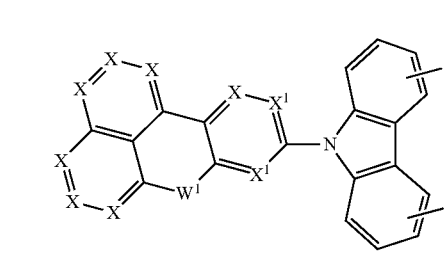

Formula (IIId)

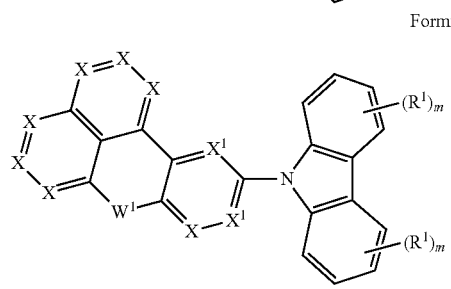

where the symbols $R^1$, $W^1$ and X have the definition given above, especially for formula (I), m is 0, 1, 2, 3 or 4, preferably 0, 1, 2 or 3, and $X^1$ is the same or different and is N or $CR^1$, where at least one $X^1$ group is N. X here is preferably the same or different and is $CR^1$ or N, more preferably $CR^1$.

Preference is also given to compounds having structures in which not more than two X groups per ring are N and preferably at least one, more preferably at least two, of the X groups per ring are selected from C—H and C-D.

Preferably, the compounds of the invention may may comprise at least one structure of the formula (IVa), (IVb), (IVc) or (IVd)

Formula (IVa)

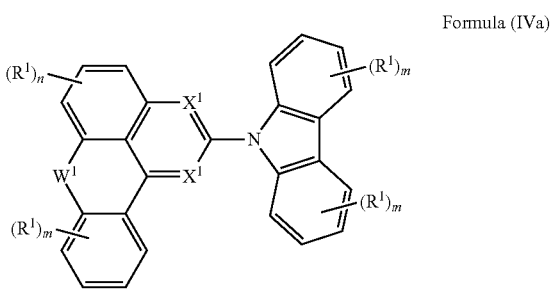

Formula (IVb)

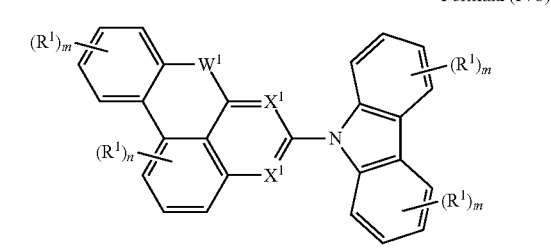

Formula (IVc)

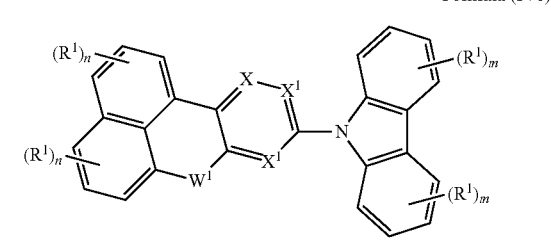

Formula (IVd)

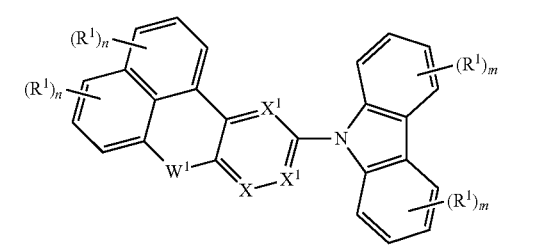

where the symbols $R^1$, $W^1$ and X used have the definition set out above, especially for formula (I), m is the same or different and is 0, 1, 2, 3 or 4, preferably 0, 1, 2 or 3, n is the same or different and is 0, 1, 2 or 3, preferably 0, 1 or 2, and $X^1$ is the same or different and is N or $CR^1$, where at least one $X^1$ group is N. X in formula (IVc) and (IVd) is preferably $CR^1$.

Preferably, the compounds of the invention may comprise at least one structure of the formula (Va), (Vb), (Vc) or (Vd)

Formula (Va)

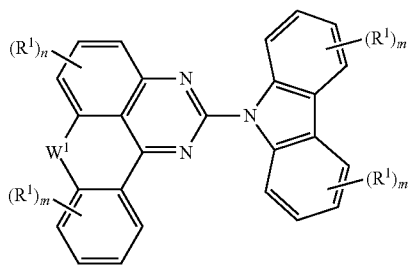

Formula (Vb)

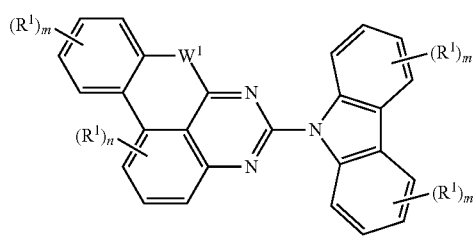

Formula (Vc)

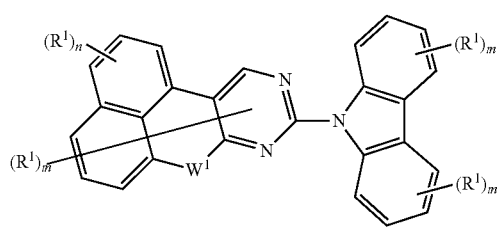

Formula (Vd)

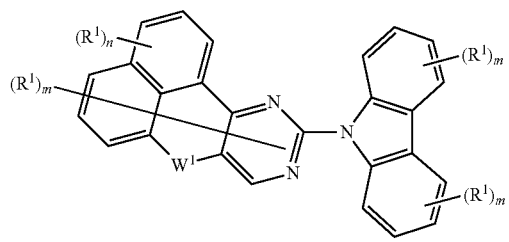

where the symbols $R^1$ and $W^1$ used have the definition set out above, especially for formula (I), m is the same or different and is 0, 1, 2, 3 or 4, preferably 0, 1, 2 or 3, and n is 0, 1, 2 or 3, preferably 0, 1 or 2.

In addition, in the structures of the formulae set out above and hereinafter, it may be the case that two adjacent $R^1$ radicals in the group of the formula (CAB-1) form a ring of the formula (DB-1), (DB-2) or (DB-3)

Formula (DB-1)

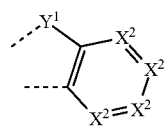

Formula (DB-2)

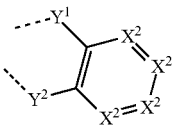

Formula (DB-3)

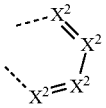

where $X^2$ is the same or different and is N or $CR^2$, preferably $CR^2$, $Y^1$ and $Y^2$ independently at each instance are O, S, $C(R^2)_2$ or $NR^2$ and the dotted lines represent the bond to the aryl or heteroaryl group, where $R^2$ has the definition given above, especially for formula (I). For reasons of clarity, it should be emphasized that the group of the formula (DB-3) together with an aromatic or heteroaromatic radical in the group of the formula (CAB-1) forms a fused ring system.

In a further-preferred embodiment, the compounds of the invention may have at least one structure of the formula (VIa), (VIb), (VIc) or (VId)

Formula (VIa)

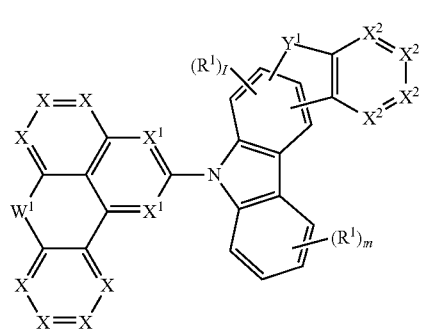

Formula (VIb)

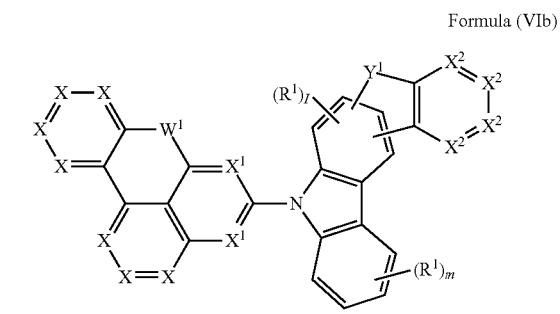

Formula (VIc)

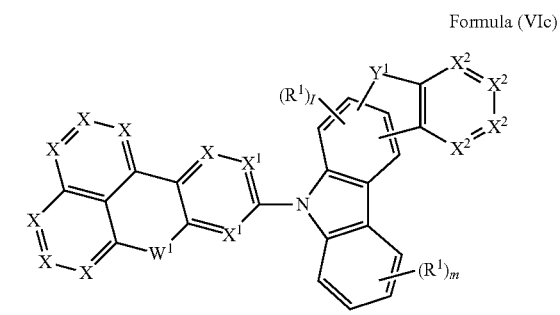

Formula (VId)

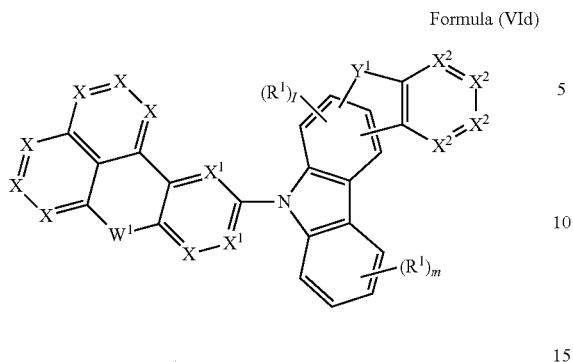

where the symbols $W^1$ and X used have the definition given above, especially for formula (I), the symbols $Y^1$ and $X^2$ have the definition given above, especially for formula (DB-1), l is 0, 1 or 2, preferably 0 or 1, m is 0, 1, 2, 3 or 4, preferably 0, 1 or 2, and $X^1$ is N or $CR^1$, where at least one $X^1$ group is N. X here is preferably the same or different and is $CR^1$ or N, more preferably $CR^1$.

The formulae depicted above and elucidated in detail hereinafter include the fusion of the (DB-1) to (DB-2) groups in any possible position and orientation. This is shown hereinafter by way of example for the compound (VIa), where $R^1$ radicals are not shown for the sake of clarity:

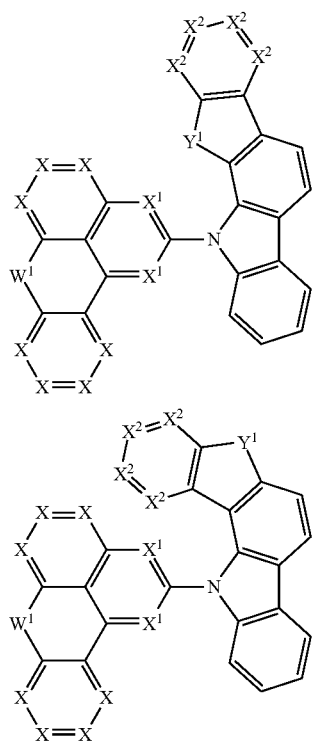

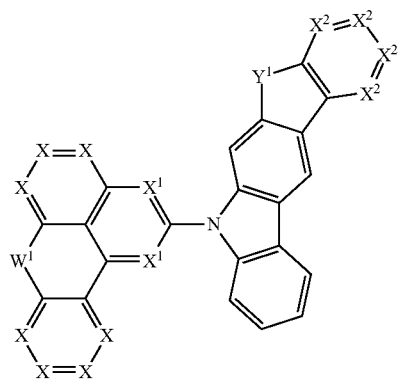

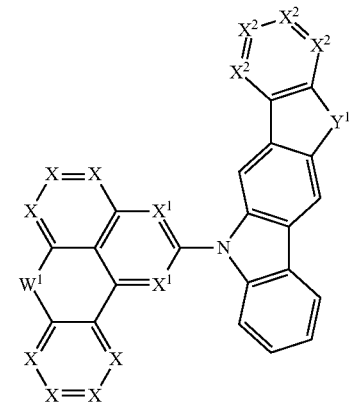

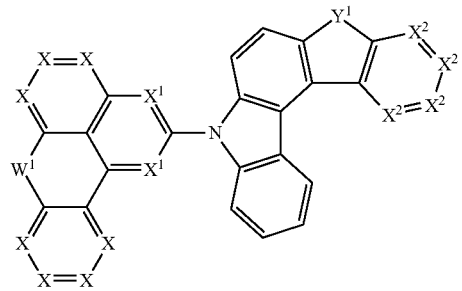

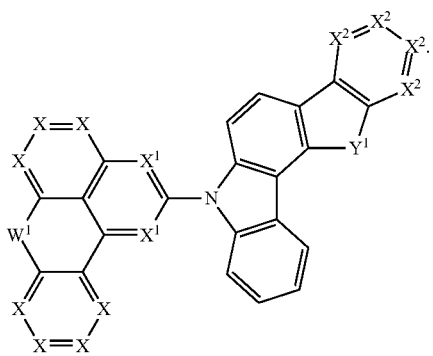

It may further be the case that compounds of the invention comprise at least one structure of the formula (VIIa), (VIIb), (VIIc) or (VIId)

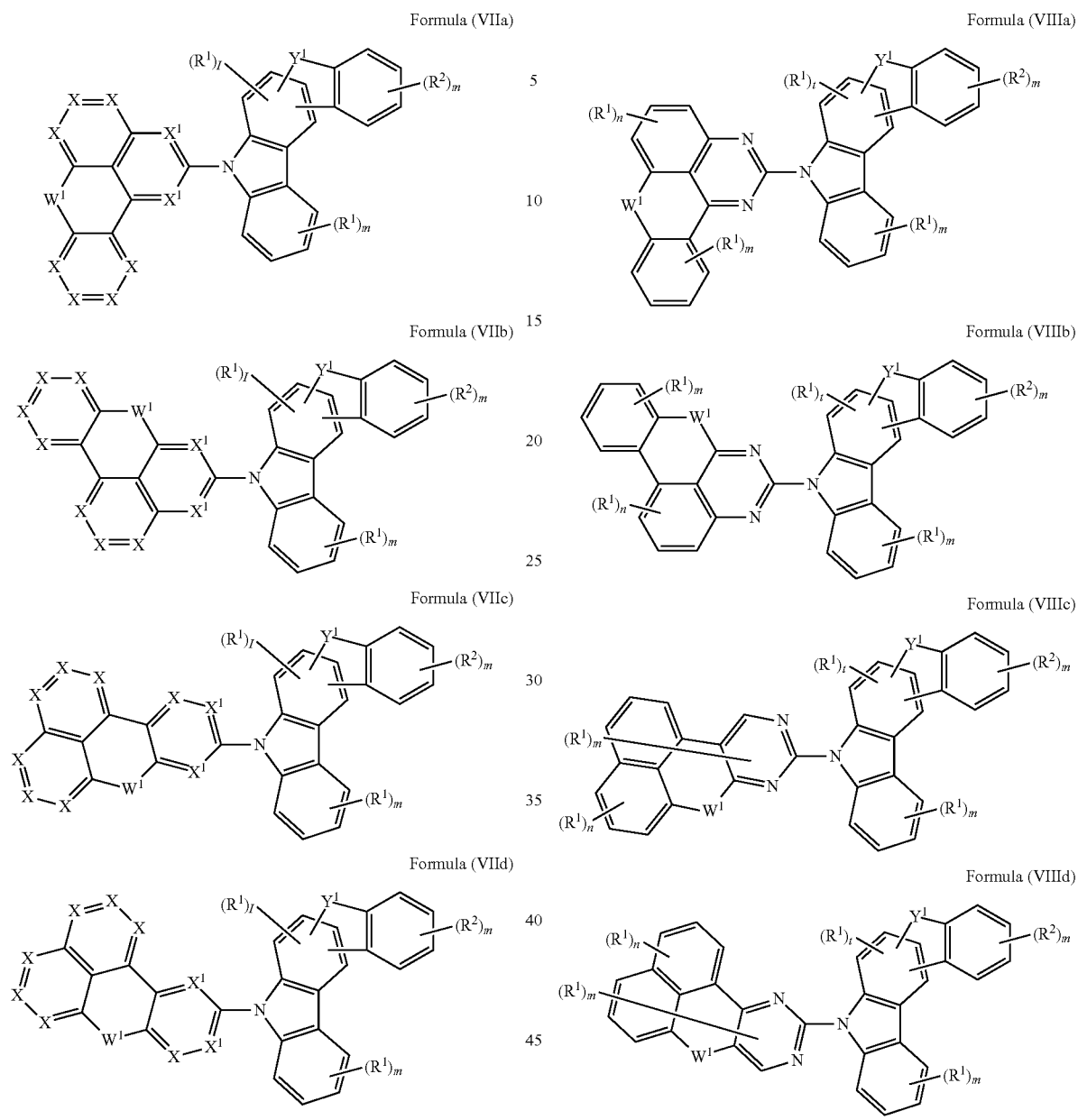

Formula (VIIa)
Formula (VIIb)
Formula (VIIc)
Formula (VIId)
Formula (VIIIa)
Formula (VIIIb)
Formula (VIIIc)
Formula (VIIId)

where the symbols $W^1$, $R^1$, $R^2$ and X used have the definition set out above, especially for formula (I), the symbol $Y^1$ has the definition given above, especially for formula (DB-1), l is 0, 1 or 2, preferably 0 or 1, m is the same or different and is 0, 1, 2, 3 or 4, preferably 0, 1 or 2, and $X^1$ is N or $CR^1$, where at least one $X^1$ group is N. X here is preferably the same or different and is $CR^1$ or N, more preferably $CR^1$.

Preference is further given to compounds comprising at least one structure of formula (VIIIa), (VIIIb), (VIIIc) or (VIIId)

where the symbols $W^1$, $R^1$ and $R^2$ used have the definition set out above, especially for formula (I), the symbol $Y^1$ has the definition given above, especially for formula (DB-1), l is 0, 1 or 2, preferably 0 or 1, n is 0, 1, 2 or 3, preferably 0, 1 or 2, and m is the same or different and is 0, 1, 2, 3 or 4, preferably 0, 1 or 2.

In a further-preferred embodiment, the compounds of the invention may comprise at least one structure of the formula (IXa), (IXb), (IXc) or (IXd)

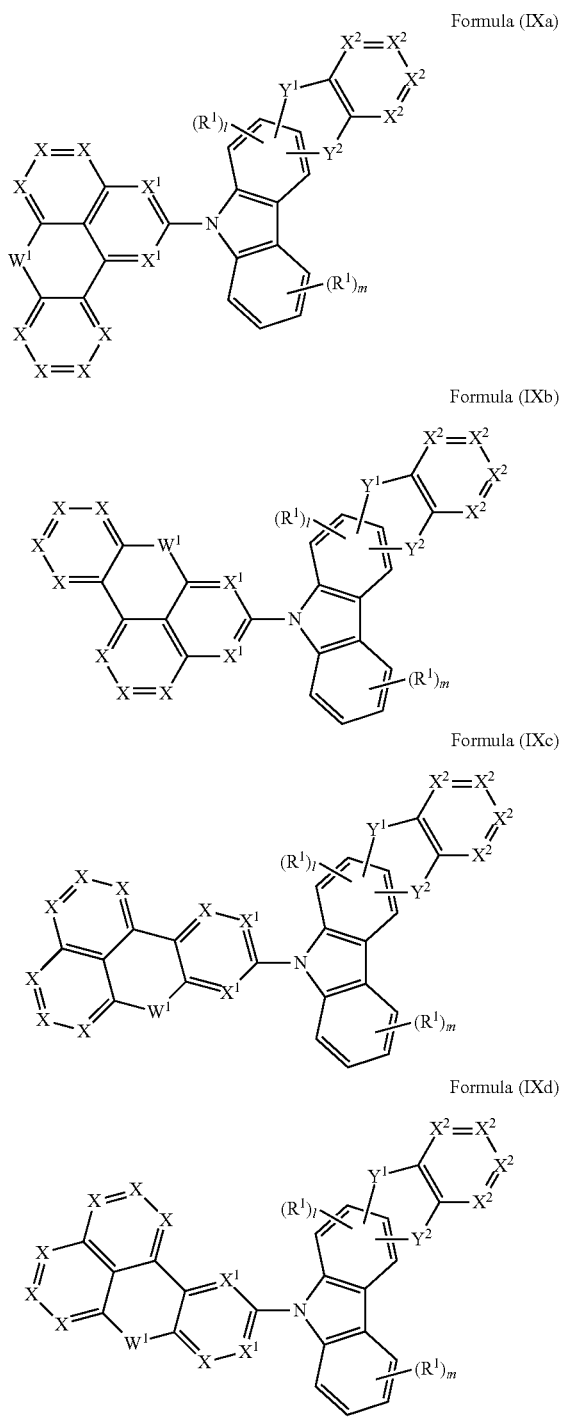

Formula (IXa)

Formula (IXb)

Formula (IXc)

Formula (IXd)

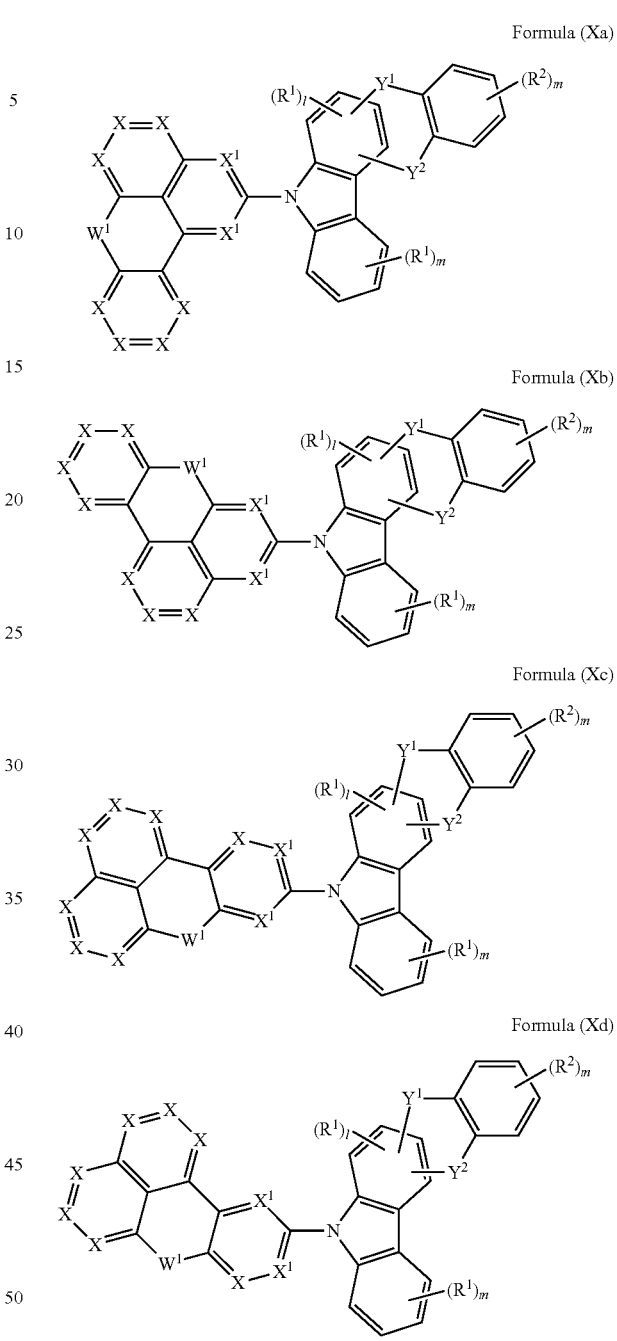

Formula (Xa)

Formula (Xb)

Formula (Xc)

Formula (Xd)

where the symbols $W^1$, $R^1$ and X used have the definition set out above, especially for formula (I), the symbols $Y^1$, $Y^2$ and $X^2$ have the definition given above, especially for formula (DB-2), l is 0, 1 or 2, preferably 0 or 1, m is 0, 1, 2, 3 or 4, preferably 0, 1 or 2, and $X^1$ is the same or different and is N or $CR^1$, where at least one $X^1$ group is N. X here is preferably the same or different and is $CR^1$ or N, more preferably $CR^1$.

In addition, the compounds of the invention may comprise at least one structure of the formula (Xa), (Xb), (Xc) or (Xd)

where the symbols $W^1$, $R^1$, $R^2$ and X used have the definition set out above, especially for formula (I), the symbols $Y^1$ and $Y^2$ have the definition given above, especially for formula (DB-2), l is 0, 1 or 2, preferably 0 or 1, m is the same or different and is 0, 1, 2, 3 or 4, preferably 0, 1 or 2, and $X^1$ is N or $CR^1$, where at least one $X^1$ group is N. X here is preferably the same or different and is $CR^1$ or N, more preferably $CR^1$.

Preference is further given to compounds comprising at least one structure of formula (XIa), (XIb), (XIc) or (XId)

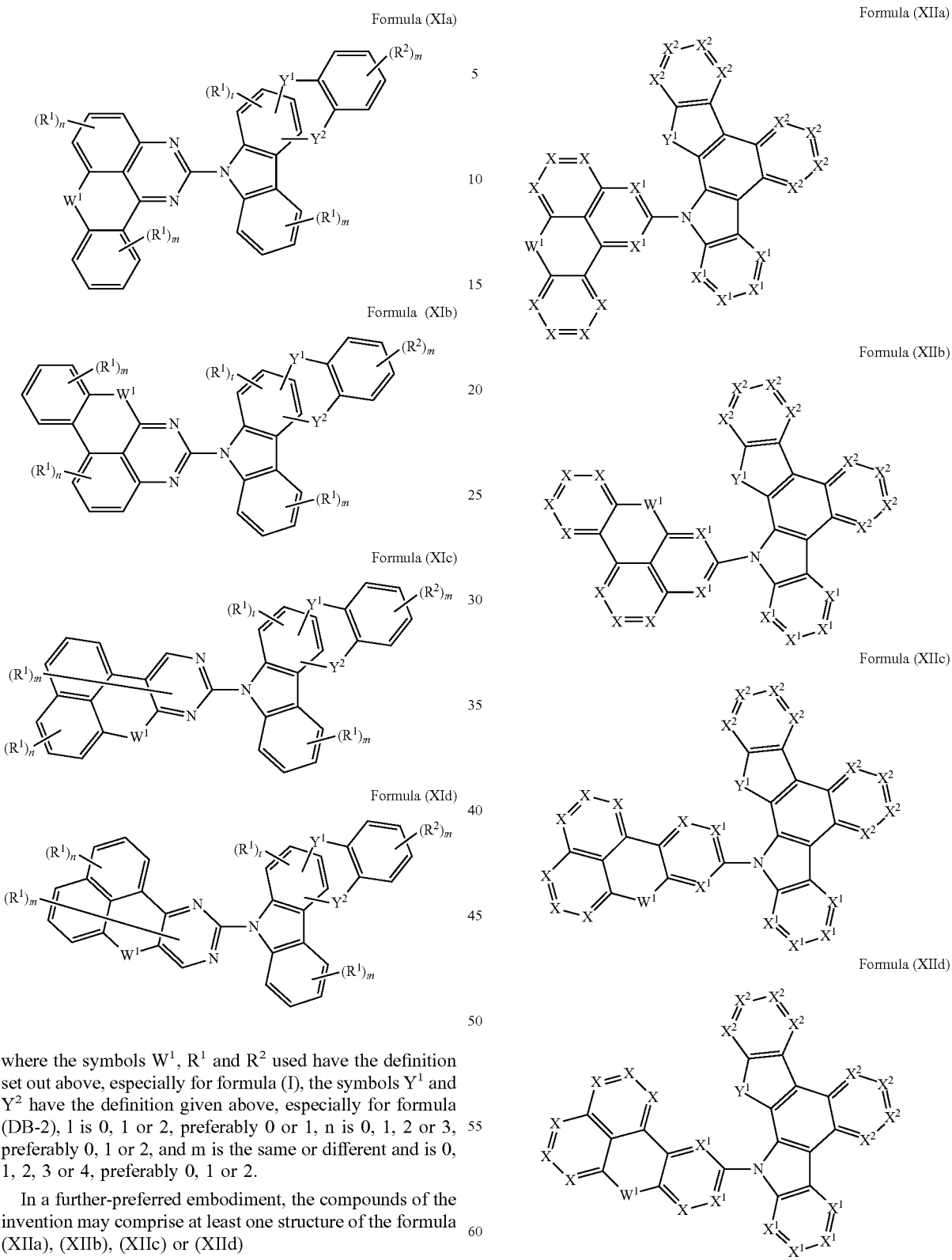

where the symbols $W^1$, $R^1$ and $R^2$ used have the definition set out above, especially for formula (I), the symbols $Y^1$ and $Y^2$ have the definition given above, especially for formula (DB-2), l is 0, 1 or 2, preferably 0 or 1, n is 0, 1, 2 or 3, preferably 0, 1 or 2, and m is the same or different and is 0, 1, 2, 3 or 4, preferably 0, 1 or 2.

In a further-preferred embodiment, the compounds of the invention may comprise at least one structure of the formula (XIIa), (XIIb), (XIIc) or (XIId)

where the symbols $W^1$ and X used have the definition set out above, especially for formula (I), the symbols $X^2$ and $Y^1$ have the definition given above, especially for formula (DB-2) and (DB-3), and $X^1$ is N or $CR^1$, where at least one $X^1$ group adjacent to the carbon atom to which the carbazole derivative group is bonded is N. X here is preferably the same or different and is $CR^1$ or N, more preferably $CR^1$.

In addition, the compounds of the invention may comprise at least one structure of the formula (XIIIa), (XIIIb), (XIIIc) or (XIIId)

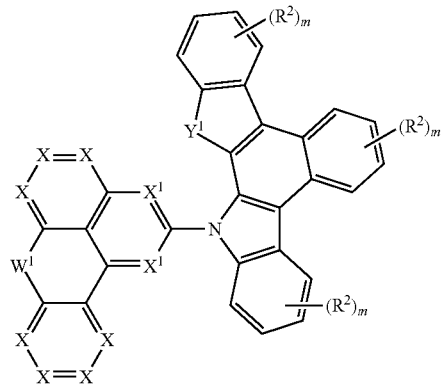

Formula (XIIIa)

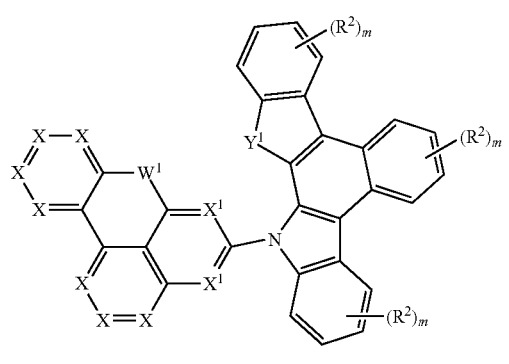

Formula (XIIIb)

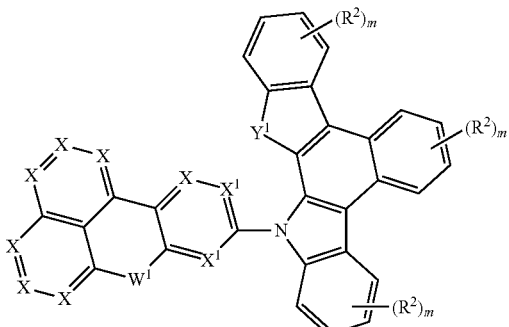

Formula (XIIIc)

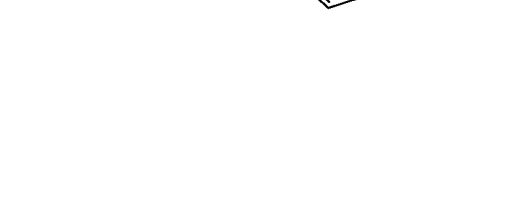

Formula (XIIId)

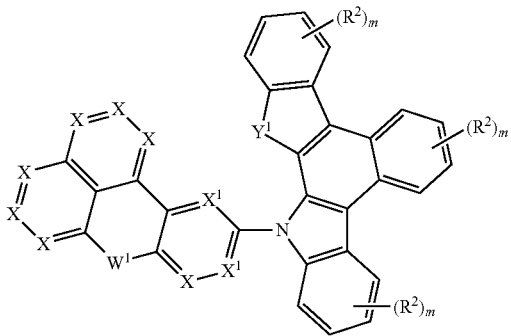

where the symbols $W^1$, $R^2$ and X used have the definition set out above, especially for formula (I), the symbol $Y^1$ has the definition given above, especially for formula (DB-2), l is 0, 1 or 2, preferably 0 or 1, m is the same or different and is 0, 1, 2, 3 or 4, preferably 0, 1 or 2, and $X^1$ is N or $CR^1$, where at least one $X^1$ group is N. X here is preferably the same or different and is $CR^1$ or N, more preferably $CR^1$.

Preference is further given to compounds comprising at least one structure of formula (XIVa), (XIVb), (XIVc) or (XIVd)

Formula (XIVa)

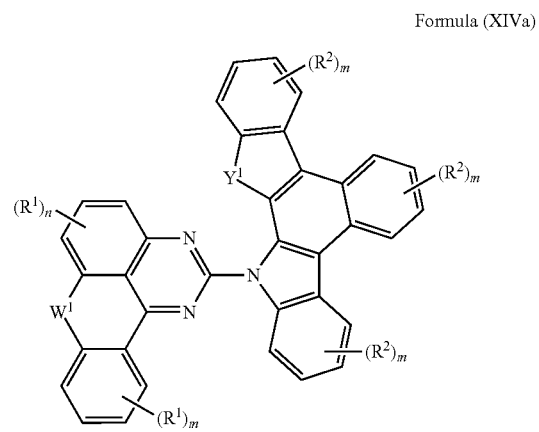

Formula (XIVb)

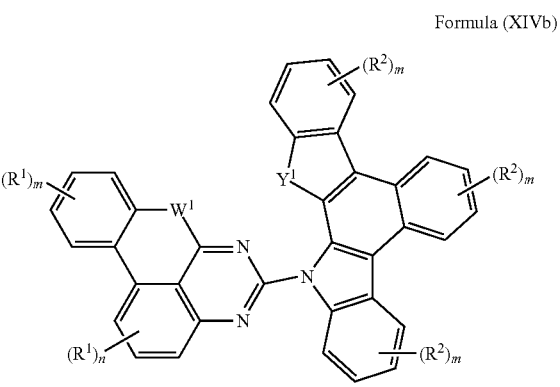

Formula (XIVc)

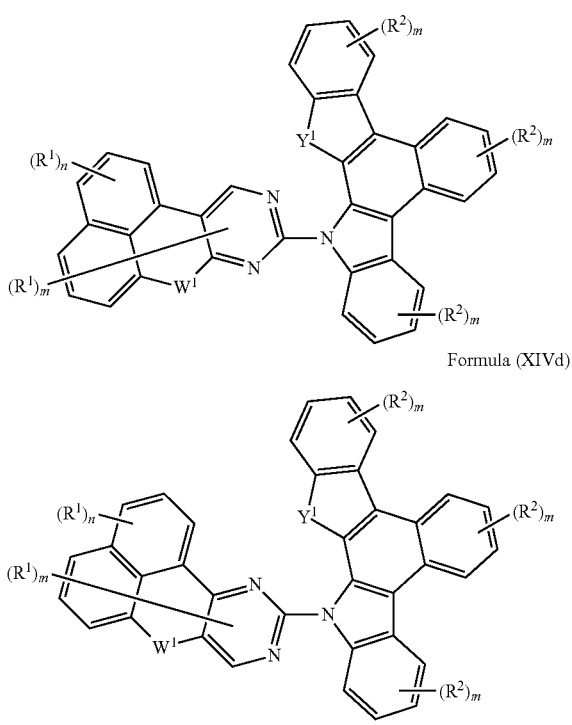

Formula (XIVd)

where the symbols $W^1$, $R^1$, $R^2$ and X used have the definition set out above, especially for formula (I), the symbol $Y^1$ has the definition given above, especially for formula (DB-2), l is 0, 1 or 2, preferably 0 or 1, m is the same or different and is 0, 1, 2, 3 or 4, preferably 0, 1 or 2, and $X^1$ is N or $CR^1$, where at least one $X^1$ group is N.

In a further embodiment, it may be the case that, in the formulae (VIa), (VIb), (VIc), (VId), (VIIa), (VIIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc) and/or (XIVd), the symbols $W^1$ and $Y^1$ are the same. In addition, the symbols $W^1$ and $Y^1$ may be different.

Preference is further given to compounds which are characterized in that, in the formulae (VIa), (VIb), (VIc), (VId), (VIIa), (VIIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc) and/or (XIVd), the symbol $W^1$ is O and the symbol $Y^1$ is O, S, $C(R^2)_2$ or $NR^2$.

Preference is also given to compounds which are characterized in that, in the formulae (VIa), (VIb), (VIc), (VId), (VIIa), (VIIb), (VIIc), (VIIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc) and/or (XIVd), the symbol $W^1$ is S and the symbol $Y^1$ is O, S, $C(R^2)_2$ or $NR^2$.

In a further embodiment, it may be the case that, in the formulae (IXa), (IXb), (IXc), (IXd), (Xa), (Xb), (Xc), (Xd), (XIa), (XIb), (XIc) and/or (XId), the symbols $W^1$ and $Y^2$ are the same. In addition, the symbols $W^1$ and $Y^2$ may be different.

Preference is further given to compounds which are characterized in that, in the formulae (IXa), (IXb), (IXc), (IXd), (Xa), (Xb), (Xc), (Xd), (XIa), (XIb), (XIc) and/or (XId), the symbol $W^1$ is O and the symbol $Y^2$ is O, S, $C(R^2)_2$ or $NR^2$.

Preference is also given to compounds which are characterized in that, in the formulae (IXa), (IXb), (IXc), (IXd), (Xa), (Xb), (Xc), (Xd), (XIa), (XIb), (XIc) and/or (XId), the symbol $W^1$ is S and the symbol $Y^2$ is O, S, $C(R^2)_2$ or $NR^2$.

In a further embodiment, it may be the case that, in the formulae (IXa), (IXb), (IXc), (IXd), (Xa), (Xb), (Xc), (Xd), (XIa), (XIb), (XIc) and/or (XId), the symbols $Y^1$ and $Y^2$ are the same. In addition, the symbols $Y^1$ and $Y^2$ may be different.

Furthermore, preference is given to compounds having structures of formula (IIa), (IIb), (IIc), (IId), (IIIa), (IIIb), (IIIc), (IIId), (VIa), (VIb), (VIc), (VId), (VIIa), (VIIb), (VIIc), (VIIId), (IXa), (IXb), (IXc), (IXd), (Xa), (Xb), (Xc) and/or (Xd) in which not more than four, preferably not more than two, X groups are N, and more preferably all the X groups are $CR^1$, where preferably at most four, more preferably at most three and especially preferably at most two of the $CR^1$ groups that X represents are not the CH group.

In addition, it may be the case that the $R^1$ substituents of the carbazole group of formula (CAB-1), together with the ring atoms of the carbazole group, do not form a fused aromatic or heteroaromatic ring system, preferably any fused ring system. This includes the formation of a fused ring system with possible $R^2$, $R^3$ substituents which may be bonded to the $R^1$ radicals. It may preferably be the case that the $R^1$ substituents of the carbazole group of formula (CAB-1) do not form any fused ring system with the ring atoms of the carbazole group. This includes the formation of a ring system with possible $R^2$, $R^3$ substituents which may be bonded to the $R^1$ radicals. When the $R^1$ substituents of the carbazole group of formula (CAB-1) form a fused ring system, this is preferably a group of the above-described formula (DB-1), (DB-2) and/or (DB-3).

If the group of the formula (CAB-1) is a simple carbazole, i.e. more particularly when no group of the above-described formulae (DB-1), (DB-2) and/or (DB-3) is attached by fusion, it is preferable when the carbazole has exactly one $R^1$ substituent. This $R^1$ substituent is preferably in the para position to the nitrogen atom of the carbazole radical.

In a further-preferred embodiment, the compounds of the invention may comprise at least one structure of the formula (XVa), (XVb), (XVc) or (XVd)

Formula (XVa)

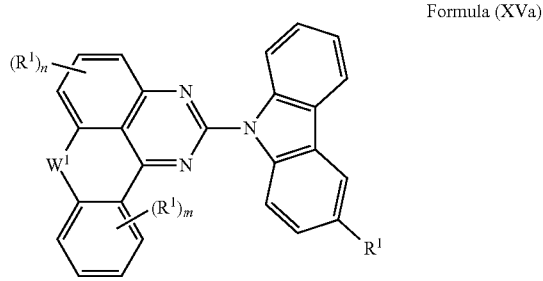

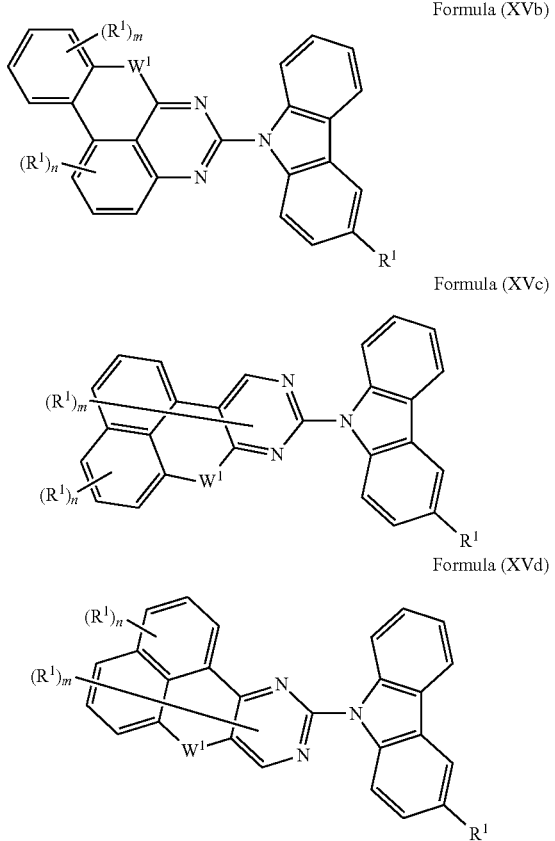

Formula (XVb)

Formula (XVc)

Formula (XVd)

where the symbols $W^1$ and $R^1$ used have the definition set out above, especially for formula (I), n is 0, 1, 2 or 3, preferably 0, 1 or 2, and m is 0, 1, 2, 3 or 4, preferably 0, 1 or 2.

Preferably, the $R^1$ radical bonded to the carbazole group of the formula (XVa), (XVb), (XVc) or (XVd) is an aromatic or heteroaromatic ring system which has 5 to 24 aromatic ring atoms and may be substituted in each case by one or more $R^2$ radicals, but is preferably unsubstituted, particular preference being given to an aromatic ring system, especially an aryl group. Preferably, the $R^1$ radical bonded to the carbazole group of the formula (XVa), (XVb), (XVc) or (XVd) is an aromatic or heteroaromatic ring system which has 5 to 24, preferably 6 to 12, aromatic ring atoms and may be substituted in each case by one or more $R^2$ radicals, but is preferably unsubstituted. The preferred groups that the $R^1$ radical bonded to the carbazole group in the formula (XVa), (XVb), (XVc) or (XVd) may represent especially include phenyl, ortho-, meta- or para-biphenyl, terphenyl, especially branched terphenyl, quaterphenyl, especially branched quaterphenyl, 1- or 2-naphthyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl, 1-, 2-, 3- or 4-carbazolyl and indenocarbazolyl, each of which may be substituted by one or more $R^2$ radicals, but are preferably unsubstituted.

In addition, in the structures of the formulae (IIa), (IIb), (IIc), (IId), (IIIa), (IIIb), (IIIc), (IIId), (VIa), (VIb), (VIc), (VId), (VIIa), (VIIb), (VIIc), (VIId), (IXa), (IXb), (IXc), (IXd), (Xa), (Xb), (Xc), (Xd), (XIa), (XIb), (XIc), (XId), (XIIIa), (XIIIb), (XIIIc), (XIIId), (XIVa), (XIVb), (XIVc), (XIVd), (XVa), (XVb), (XVc) and/or (XVd), it may be the case that the sum total of the indices l, m and n is not more than 6, preferably not more than 4 and more preferably not more than 2.

In addition, it may be the case that the $R^1$ substituents of the heteroaromatic ring system of the formulae (I), (IIa), (IIb), (IIc), (IId), (IIIa), (IIIb), (IIIc), (IIId), (IVa), (IVb), (IVc), (IVd), (Va), (Vb), (Vc), (Vd), (VIa), (VIb), (VIc), (VId), (VIIa), (VIIb), (VIIc), (VIIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc), (XIVd), (XVa), (XVb), (XVc) and/or (XVd), together with the ring atoms of the heteroaromatic ring system, do not form a fused aromatic or heteroaromatic ring system, preferably any fused ring system. This includes the formation of a fused ring system with possible $R^2$, $R^3$ substituents which may be bonded to the $R^1$ radicals. It may preferably be the case that the $R^1$ substituents of the heteroaromatic ring system of the formulae (I), (IIa), (IIb), (IIc), (IId), (IIIa), (IIIb), (IIIc), (IIId), (IVa), (IVb), (IVc), (IVd), (Va), (Vb), (Vc), (Vd), (VIa), (VIb), (VIc), (VId), (VIa), (VIIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc), (XIVd), (XVa), (XVb), (XVc) and/or (XVd) do not form any ring system with the ring atoms of the heteroaromatic ring system. This includes the formation of a ring system with possible $R^2$, $R^3$ substituents which may be bonded to the $R^1$ radicals.

In a preferred configuration, compounds of the invention can be represented by structures of the formula (I), (IIa), (IIb), (IIc), (IId), (IIIa), (IIIb), (IIIc), (IIId), (IVa), (IVb), (IVc), (IVd), (Va), (Vb), (Vc), (Vd), (VIa), (VIb), (VIc), (VId), (VIIa), (VIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc), (XIVd), (XVa), (XVb), (XVc) and/or (XVd).

Preferably, compounds comprising structures of formula (I), (IIa), (IIb), (IIc), (IId), (IIIa), (IIIb), (IIIc), (IIId), (IVa), (IVb), (IVc), (IVd), (Va), (Vb), (Vc), (Vd), (VIa), (VIb), (VIc), (VId), (VIIa), (VIIb), (VIIc), (VIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc), (XIVd), (XVa), (XVb), (XVc) and/or (XVd) have a molecular weight of not more than 5000 g/mol, preferably not more than 4000 g/mol, especially preferably not more than 3000 g/mol, specifically preferably not more than 2000 g/mol and most preferably not more than 1200 g/mol.

In addition, it is a feature of preferred compounds of the invention that they are sublimable. These compounds generally have a molar mass of less than about 1200 g/mol.

Preferably, the aromatic or heteroaromatic group of the aromatic or heteroaromatic ring system represented by the symbol $Ar^1$ is bonded to the respective atom of the further group directly, i.e. via an atom of the aromatic or heteroaromatic group, where the symbol $Ar^1$ more preferably represents an aryl or heteroaryl radical.

In a further preferred embodiment of the invention, $Ar^1$ is the same or different at each instance and is an aromatic or heteroaromatic ring system, preferably an aryl or heteroaryl radical having 5 to 24 aromatic ring atoms, preferably having 6 to 18 aromatic ring atoms, and is more preferably an aromatic ring system, preferably an aryl radical having 6 to 12 aromatic ring atoms, or a heteroaromatic ring system, preferably a heteroaryl group which has 5 to 13 aromatic ring atoms, which may be substituted in each case by one or more $R^2$ radicals, but is preferably unsubstituted, where $R^2$ may have the definition detailed above, especially in formula (I).

Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $R^2$ radicals do not form a fused ring system with the ring atoms of the aryl group or heteroaryl group $Ar^1$ to which the $R^2$ radicals may be bonded. This includes the formation of a fused ring system with possible $R^3$ substituents which may be bonded to the $R^2$ radicals.

When X or $X^1$ is $CR^1$ or when the aromatic and/or heteroaromatic groups are substituted by $R^1$ substituents, these $R^1$ substituents are preferably selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^2$ radicals, but is preferably unsubstituted, or an aralkyl or heteroaralkyl group which has 5 to 25 aromatic ring atoms and may be substituted by one or more $R^2$ radicals; at the same time, it is optionally possible for two $R^1$ substituents preferably bonded to adjacent carbon atoms to form a monocyclic or polycyclic, aliphatic, aromatic or heteroaromatic ring system which may be substituted by one or more $R^1$ radicals, where the $Ar^1$ group has the definition given above, especially for formula (I).

More preferably, these $R^1$ substituents are selected from the group consisting of H, D, F, CN, $N(Ar^1)_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more $R^2$ radicals, but is preferably unsubstituted, or an aromatic or heteroaromatic ring system which has 5 to 24 aromatic ring atoms, preferably 6 to 18 aromatic ring atoms, more preferably 6 to 13 aromatic ring atoms, and may be substituted in each case by one or more nonaromatic $R^1$ radicals, but is preferably unsubstituted; at the same time, it is optionally possible for two $R^1$ substituents preferably bonded to adjacent carbon atoms to form a monocyclic or polycyclic aliphatic ring system which may be substituted by one or more $R^2$ radicals, but is preferably unsubstituted, where $Ar^1$ may have the definition set out above.

Most preferably, the $R^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^2$ radicals, but is preferably unsubstituted. Examples of suitable $R^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

It may additionally be the case that, in a structure of formula (I), (IIa), (IIb), (IIc), (IId), (IIIa), (IIIb), (IIIc), (IIId), (IVa), (IVb), (IVc), (IVd), (Va), (Vb), (Vc), (Vd), (VIa), (VIb), (VIc), (VId), (VIIa), (VIIb), (VIIIc), (VIIId), (VIIIa), (VIIIb), (VIIIc), (VIIId), (IXa), (IXb), (IXc), (IXd), (Xa), (Xb), (Xc), (Xd), (XIa), (XIb), (XIc), (XId), (XIIa), (XIIb), (XIIc), (XIId), (XIIIa), (XIIIb), (XIIIc), (XIIId), (XIVa), (XIVb), (XIVc), (XIVd), (XVa), (XVb), (XVc) and/or (XVd), at least one $R^1$ or $Ar^1$ radical is a group selected from the formulae ($R^1$-1) to ($R^1$-80)

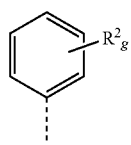

Formula ($R^1$-1)

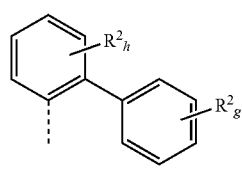

Formula ($R^1$-2)

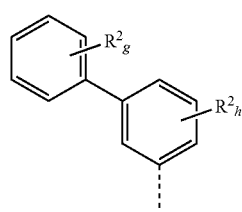

Formula ($R^1$-3)

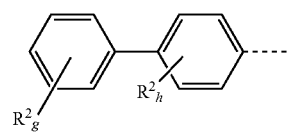

Formula ($R^1$-4)

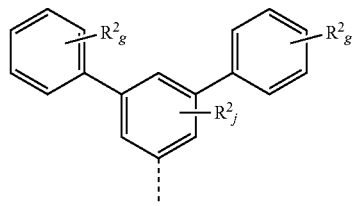

Formula ($R^1$-5)

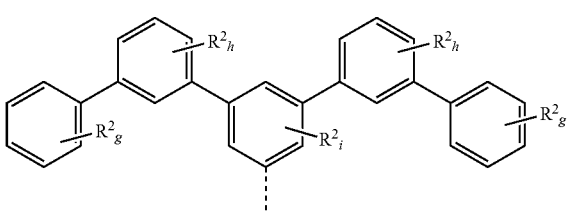

Formula ($R^1$-6)

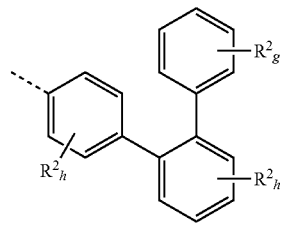
Formula (R¹-7)
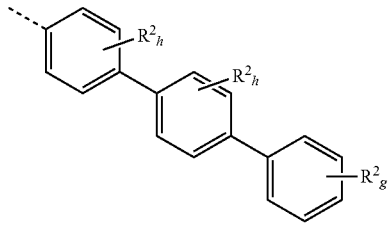
Formula (R¹-8)
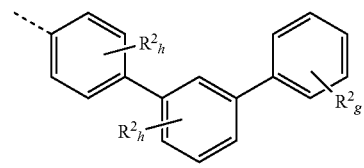
Formula (R¹-9)
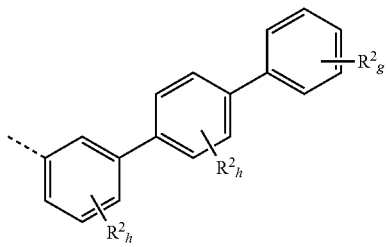
Formula (R¹-10)
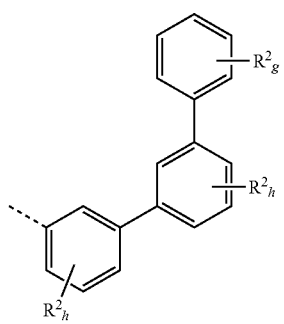
Formula (R¹-11)
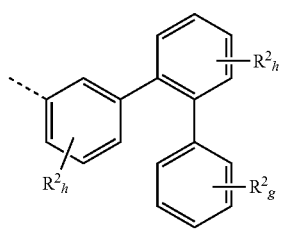
Formula (R¹-12)
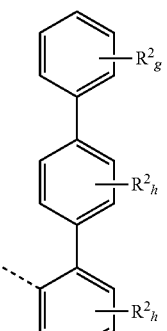
Formula (R¹-13)
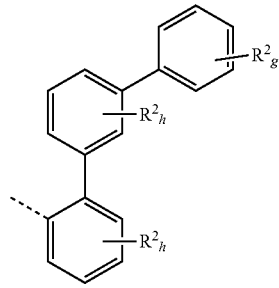
Formula (R¹-14)
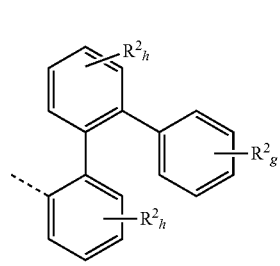
Formula (R¹-15)
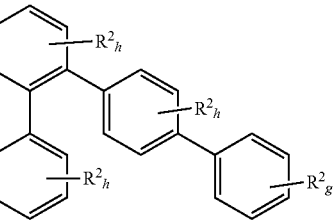
Formula (R¹-16)
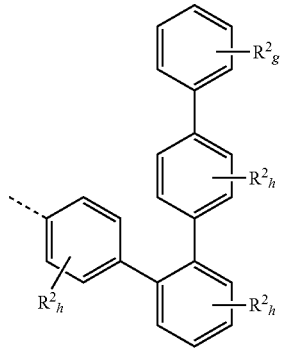
Formula (R¹-17)

Formula (R¹-18)
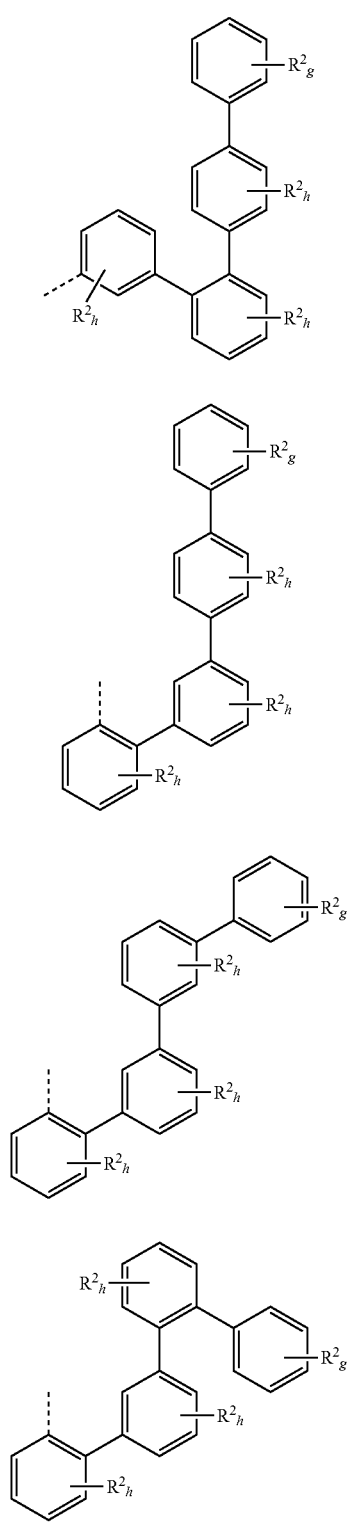
Formula (R¹-19)
Formula (R¹-20)
Formula (R¹-21)
Formula (R¹-22)
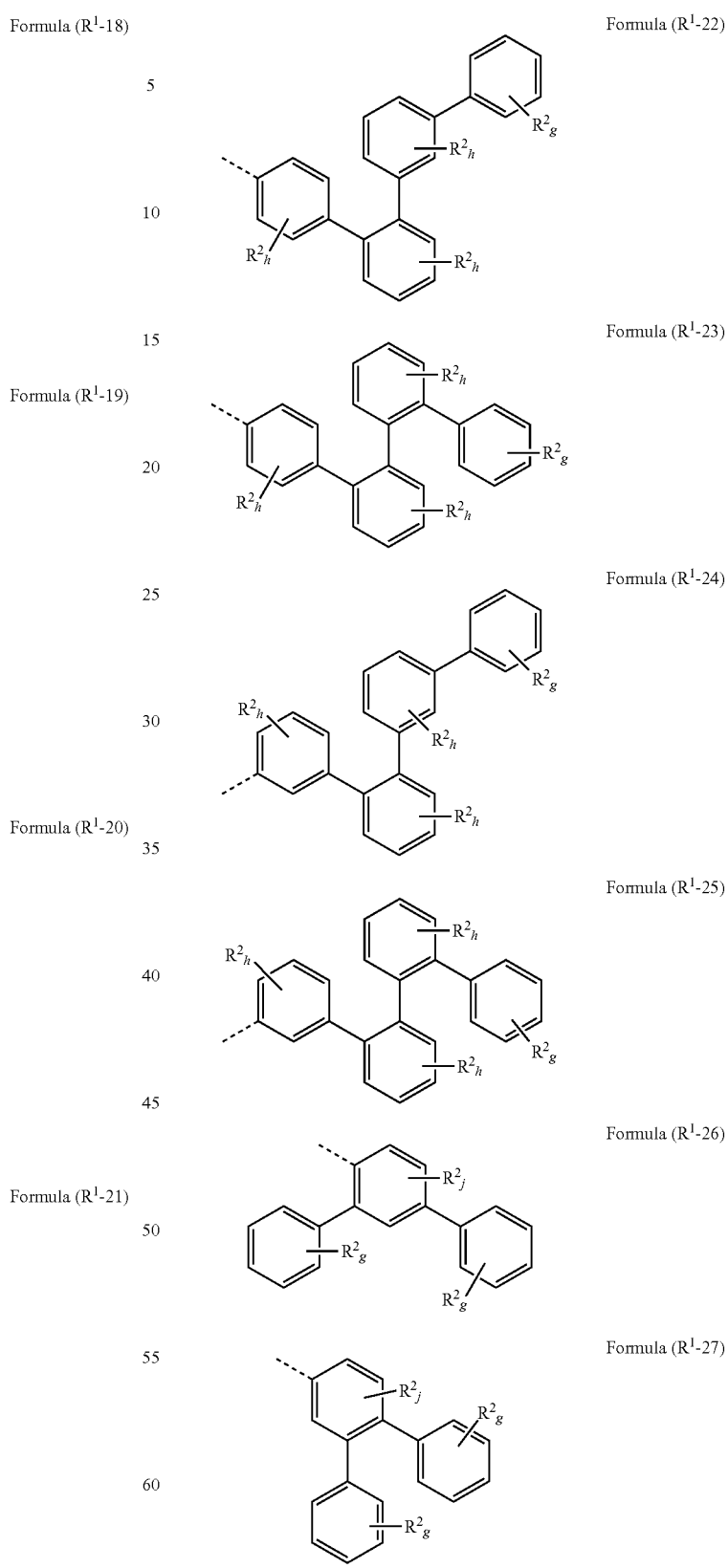
Formula (R¹-23)
Formula (R¹-24)
Formula (R¹-25)
Formula (R¹-26)
Formula (R¹-27)

-continued
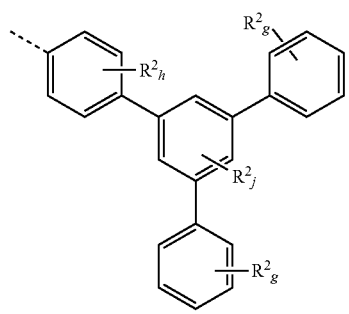
Formula (R¹-28)
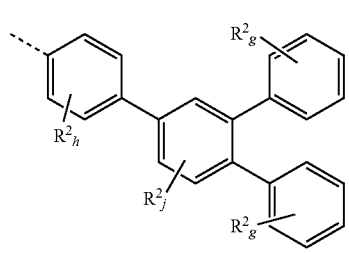
Formula (R¹-29)
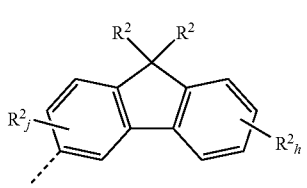
Formula (R¹-30)
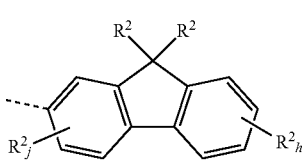
Formula (R¹-31)
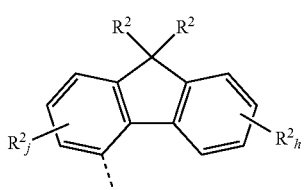
Formula (R¹-32)
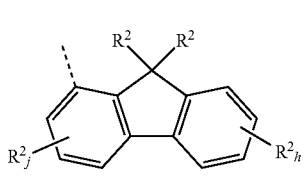
Formula (R¹-33)
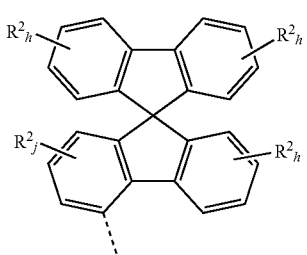
Formula (R¹-34)
-continued
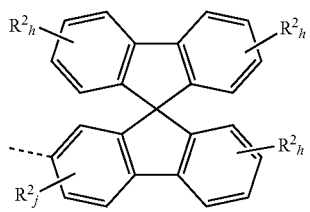
Formula (R¹-35)
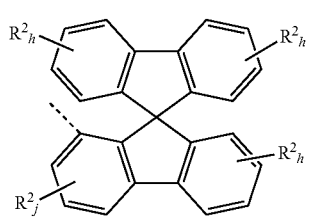
Formula (R¹-36)
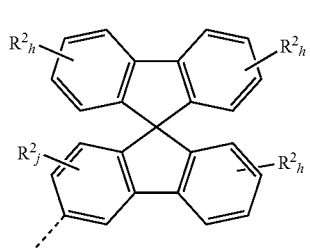
Formula (R¹-37)
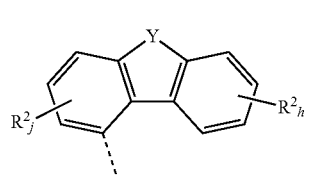
Formula (R¹-38)
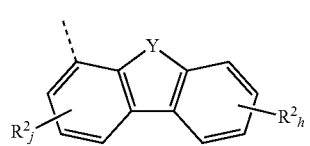
Formula (R¹-39)
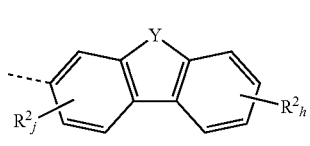
Formula (R¹-40)
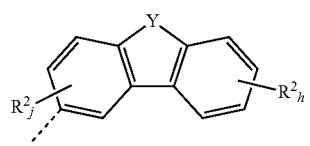
Formula (R¹-41)
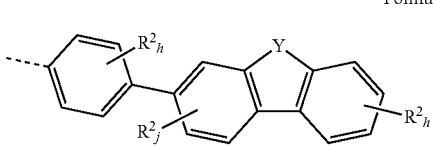
Formula (R¹-42)

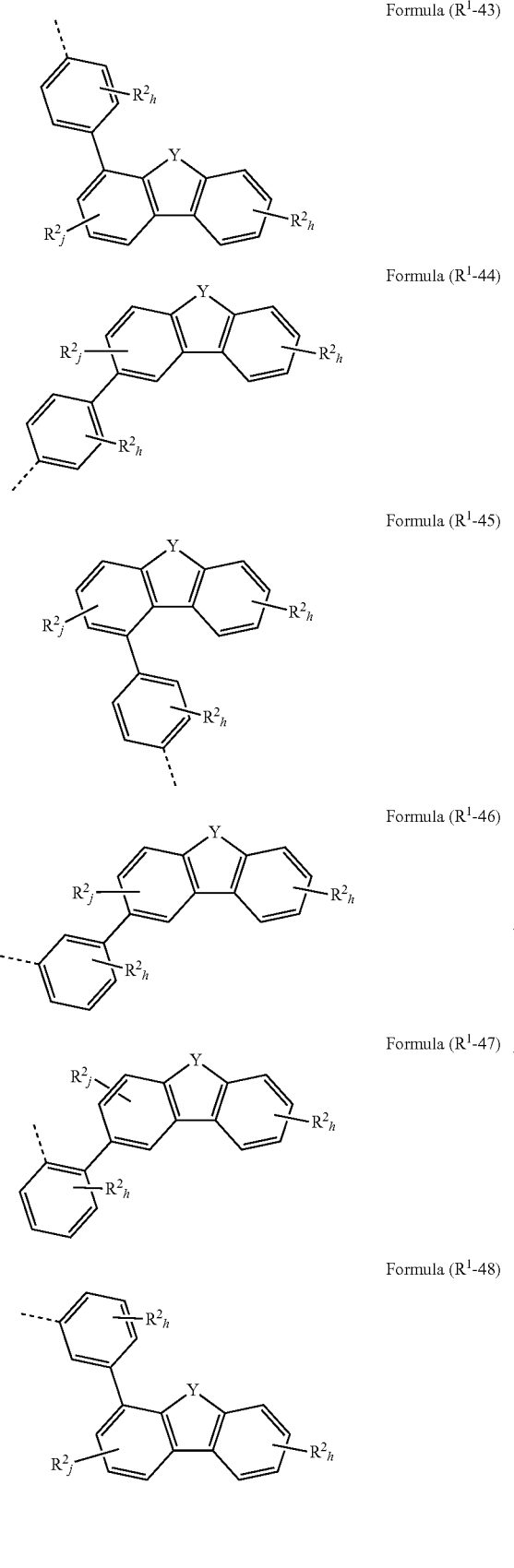
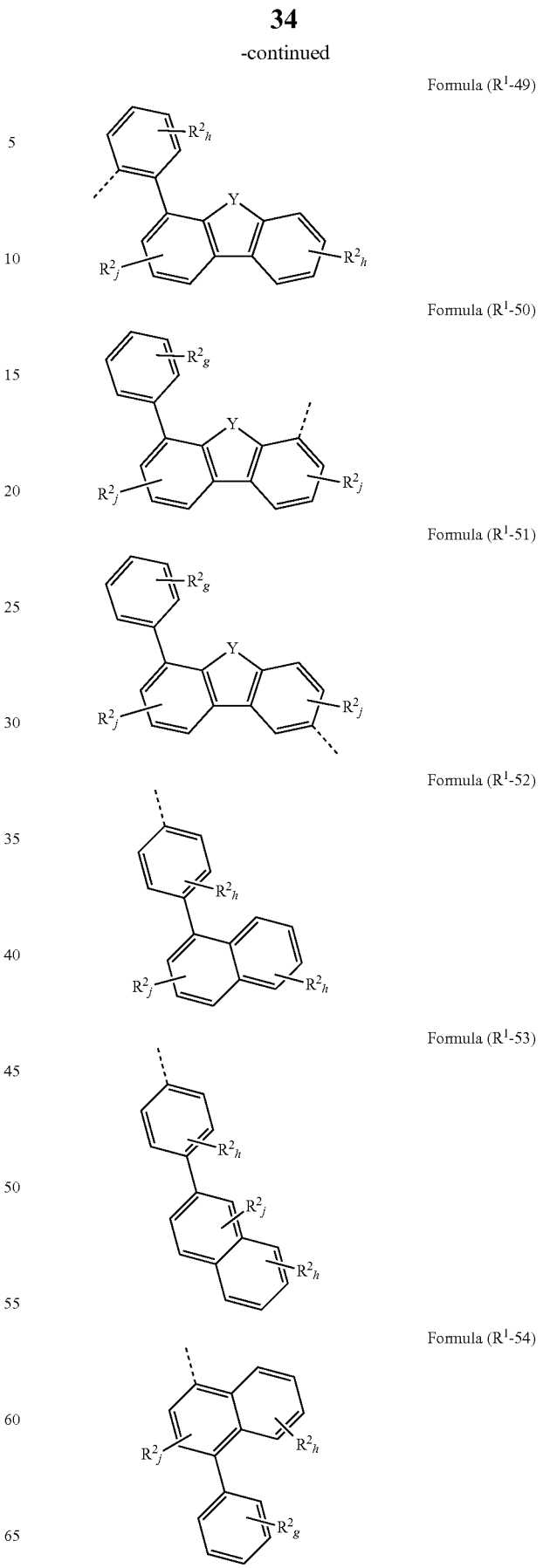

Formula (R¹-55)
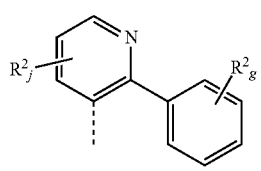
Formula (R¹-56)
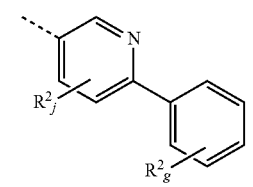
Formula (R¹-57)
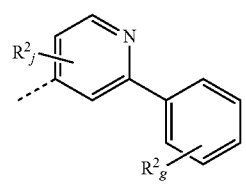
Formula (R¹-58)
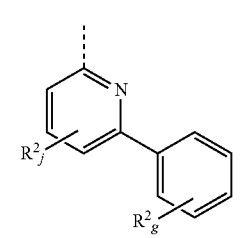
Formula (R¹-59)
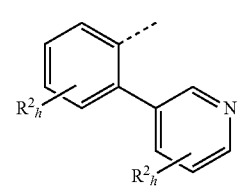
Formula (R¹-60)
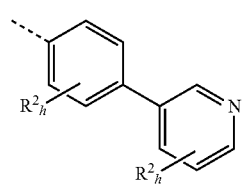
Formula (R¹-61)
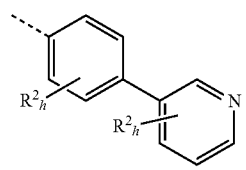
Formula (R¹-62)
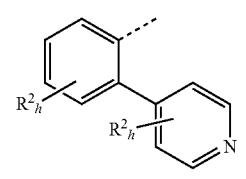
Formula (R¹-63)
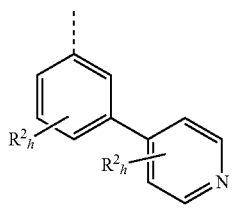
Formula (R¹-64)
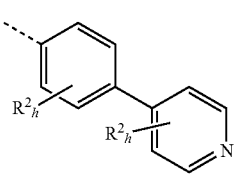
Formula (R¹-65)
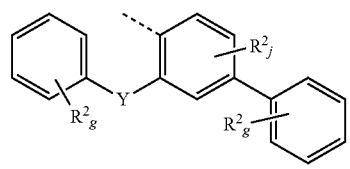
Formula (R¹-66)
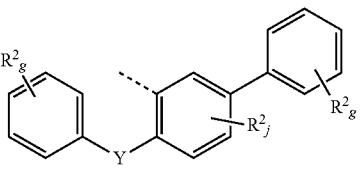
Formula (R¹-67)
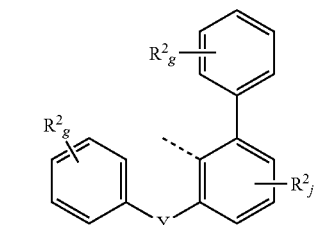
Formula (R¹-68)
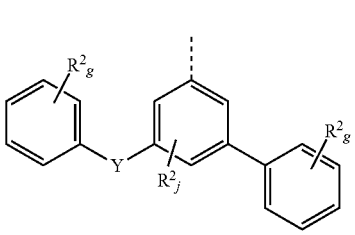
Formula (R¹-69)
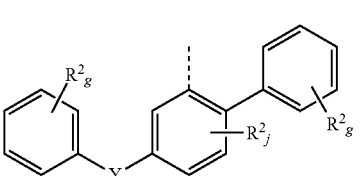
Formula (R¹-70)
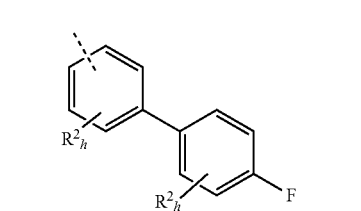

Formula (R¹-71)

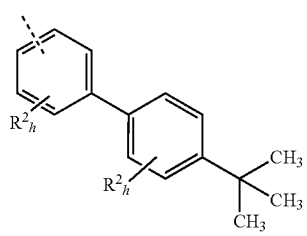

(Formula (R¹-72)

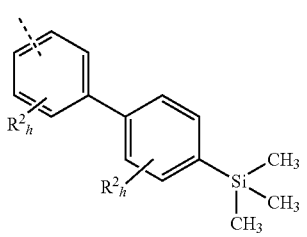

Formula (R¹-73)

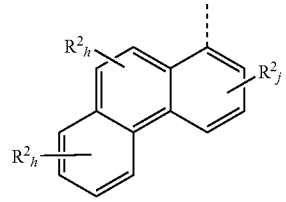

Formula (R¹-74)

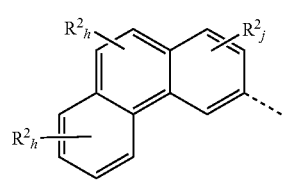

Formula (R¹-75)

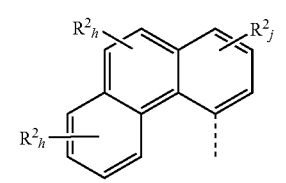

Formula (R¹-76)

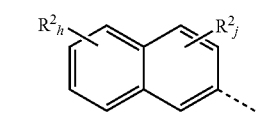

Formula (R¹-77)

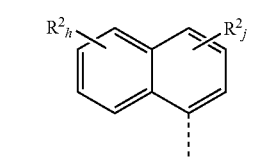

Formula (R¹-78)

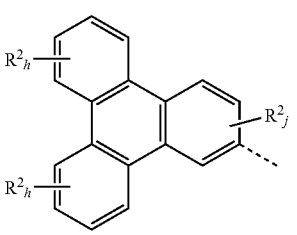

Formula (R¹-79)

Formula (R¹-80)

where the symbols used are as follows:
Y is O, S or NR², preferably O or S;
i at each instance is independently 0, 1 or 2;
j at each instance is independently 0, 1, 2 or 3;
h at each instance is independently 0, 1, 2, 3 or 4;
g at each instance is independently 0, 1, 2, 3, 4 or 5;
R² may have the definition given above, especially for formula (I); and the dotted bond marks the attachment position.

Preference is given here to the groups of the formulae R¹-1 to R¹-56, particular preference to the R¹-1, R¹-3, R¹-5, R¹-6, R¹-15, R¹-29, R¹-30, R¹-31, R¹-32, R¹-33, R¹-38, R¹-39, R¹-40, R¹-41, R¹-42, R¹-43, R¹-44 and/or R¹-45 groups.

It may preferably be the case that the sum total of the indices i, j, h and g in the structures of the formula (R¹-1) to (R¹-80) is not more than 3 in each case, preferably not more than 2 and more preferably not more than 1.

Preferably, the R² radicals in the formulae (R¹-1) to (R¹-80) do not form a fused aromatic or heteroaromatic ring system, and preferably do not form any fused ring system, with the ring atoms of the aryl group or heteroaryl group to which the R² radicals are bonded. This includes the formation of a fused ring system with possible R³ substituents which may be bonded to the R² radicals.

When the compound of the invention is substituted by aromatic or heteroaromatic R¹ or R² groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

In a further preferred embodiment of the invention, R², for example in a structure of formula (I) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Preferably, the $R^2$ radicals do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

In a further preferred embodiment of the invention, $R^3$, for example in a structure of formula (I) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

Examples of suitable compounds of the invention are the structures of the following formulae 1 to 114 shown below:

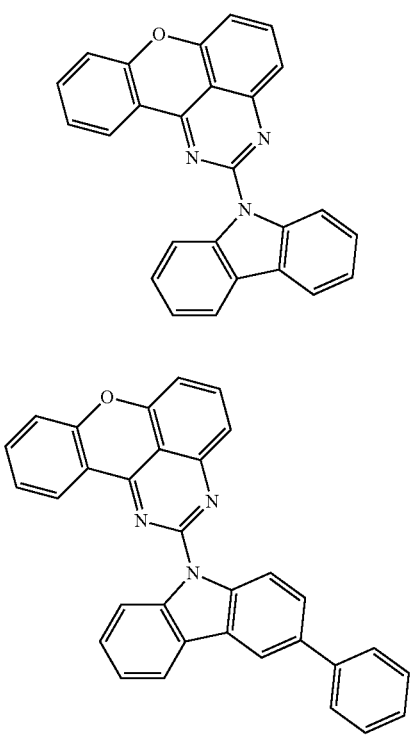

Formula 1

Formula 2

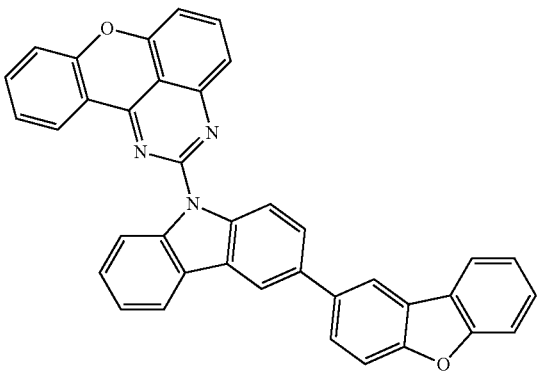

Formula 3

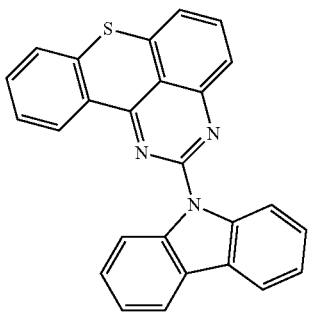

Formula 4

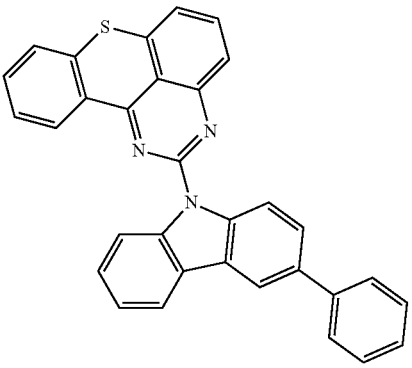

Formula 5

Formula 6

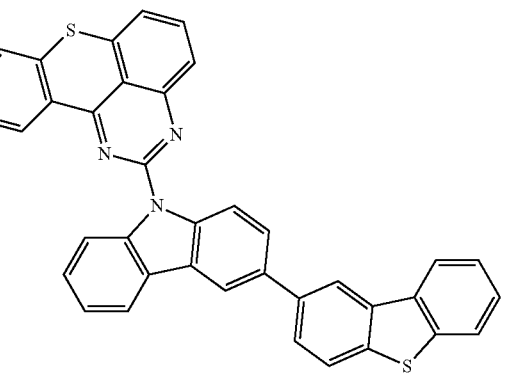

Formula 7
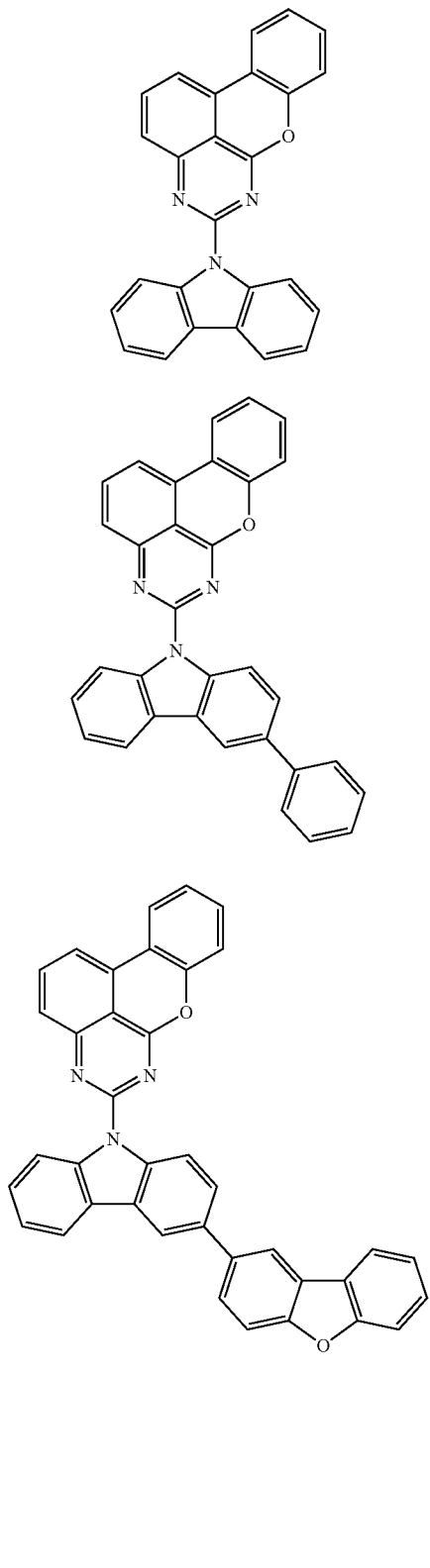
Formula 8
Formula 9
Formula 10
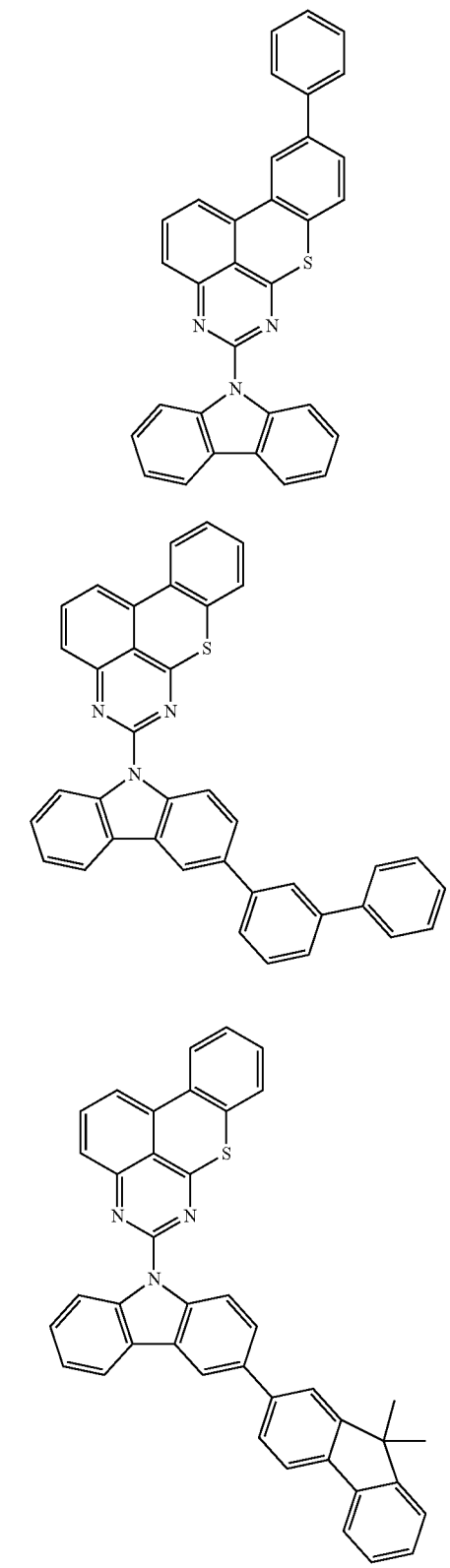
Formula 11
Formula 12

Formula 13
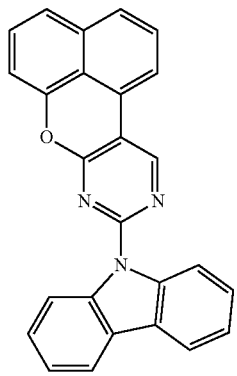
Formula 14
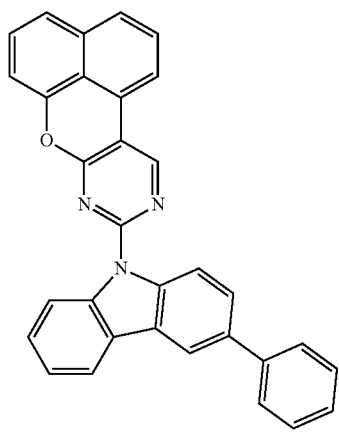
Formula 15
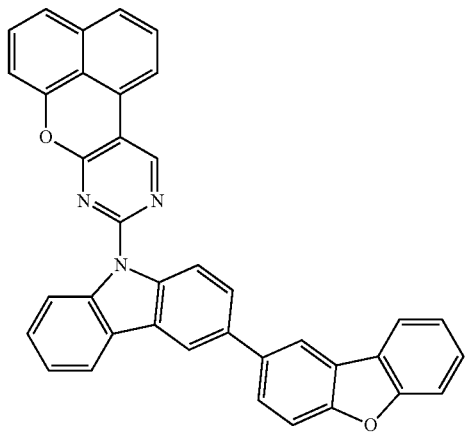
Formula 16
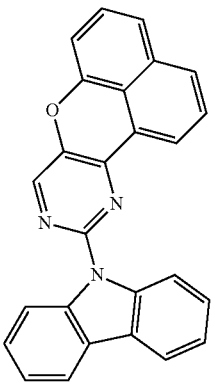
Formula 17
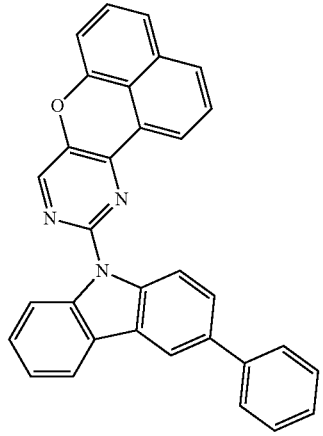
Formula 18
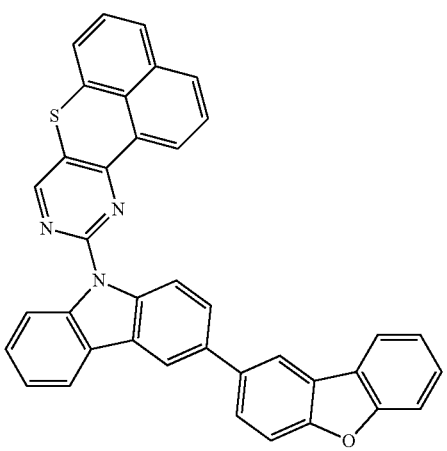
Formula 19
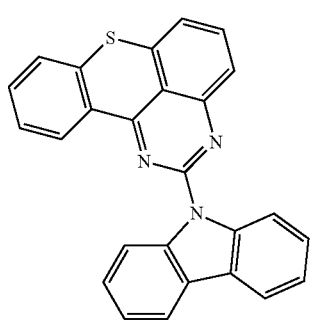

Formula 20
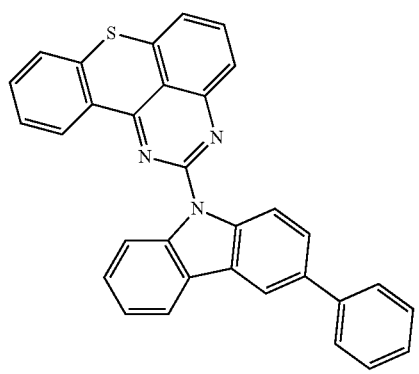
Formula 21
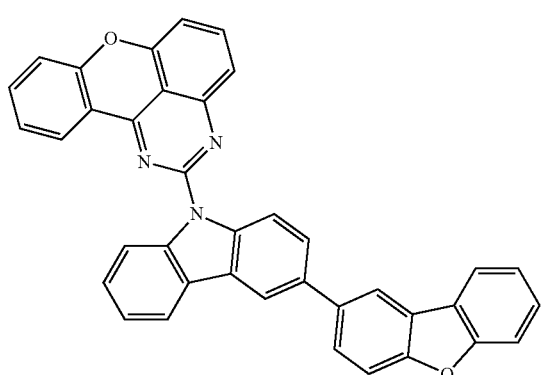
Formula 22
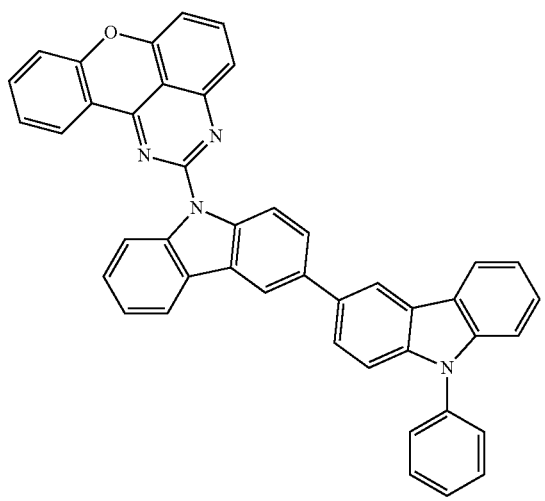
Formula 23
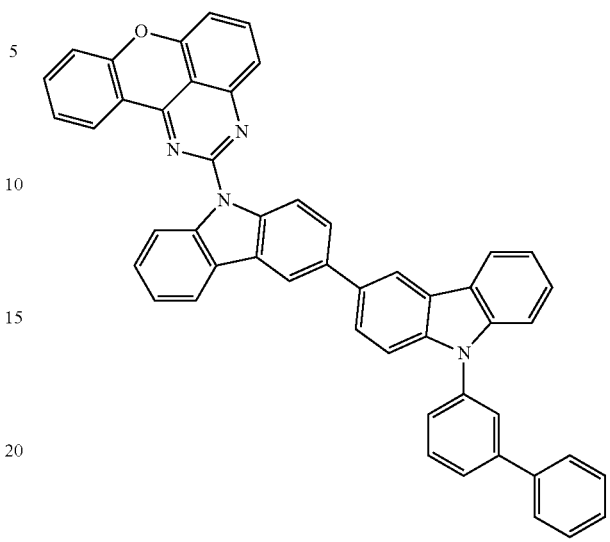
Formula 24
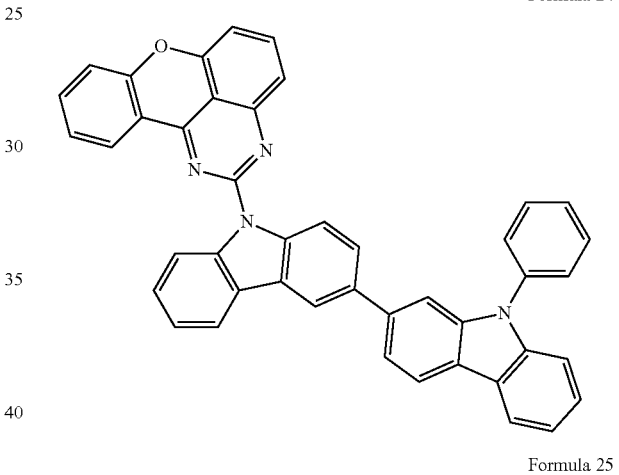
Formula 25
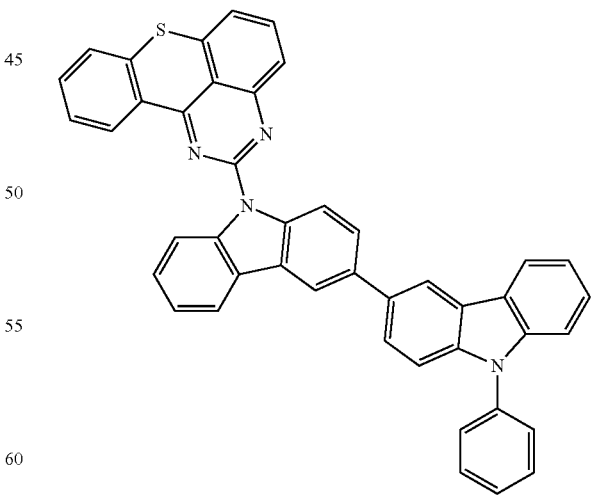

Formula 26
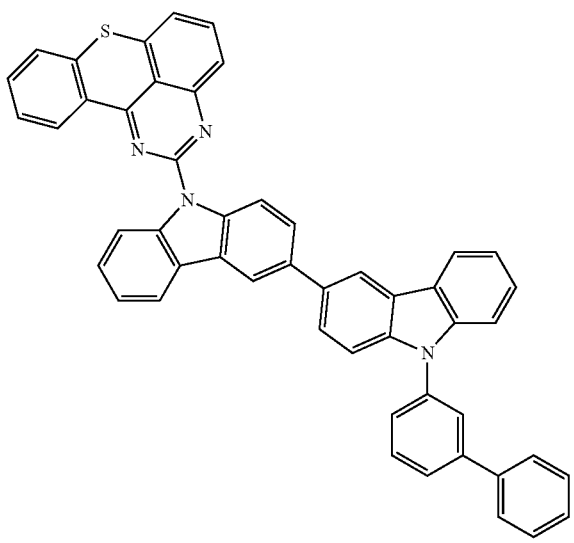
Formula 27
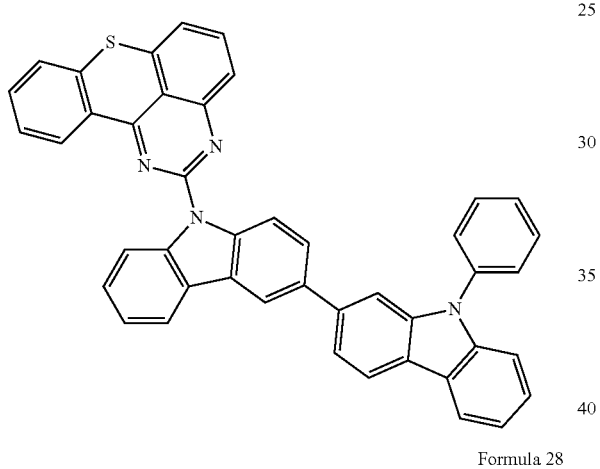
Formula 28
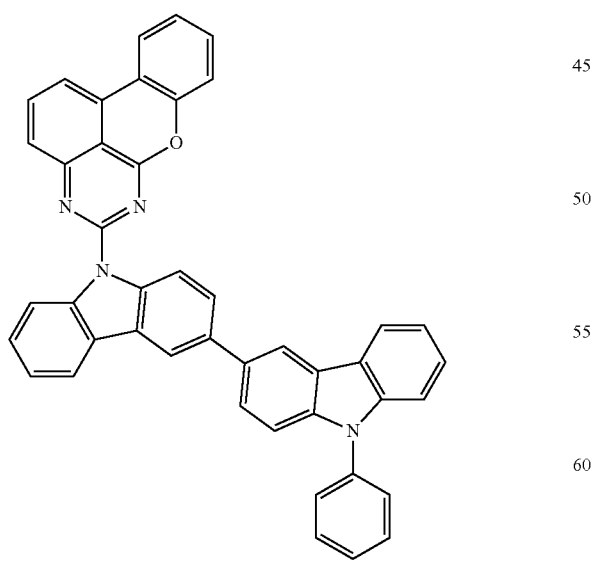
Formula 29
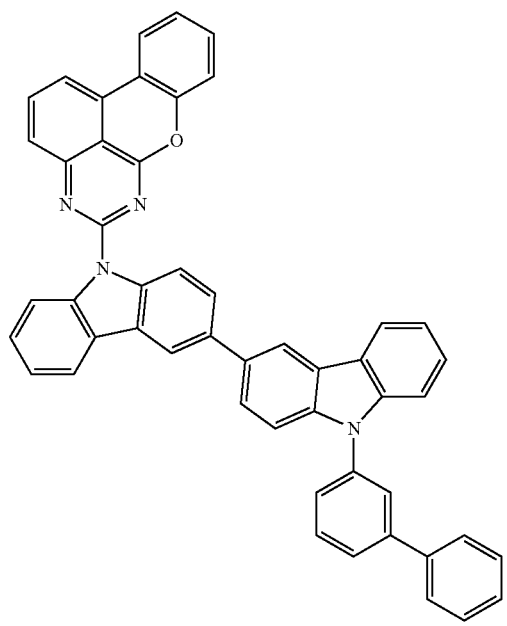
Formula 30
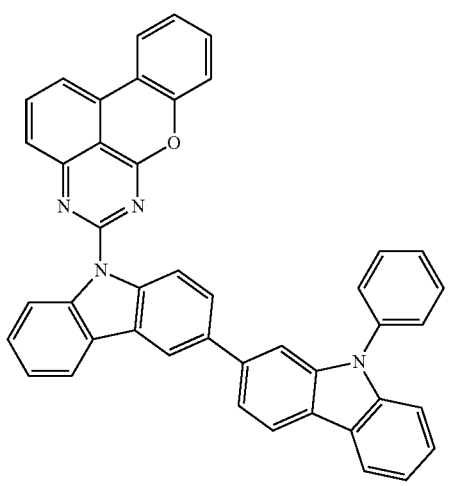

Formula 31
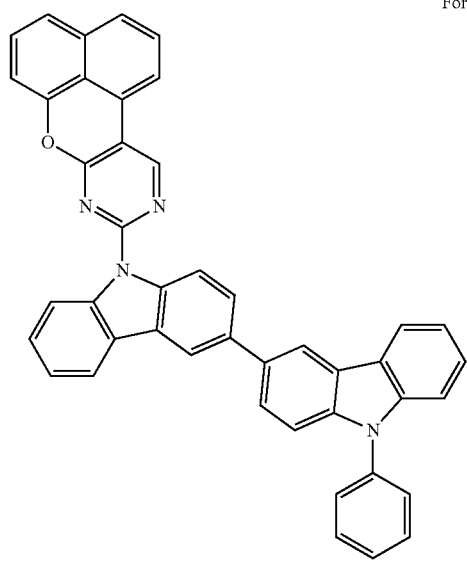
Formula 32
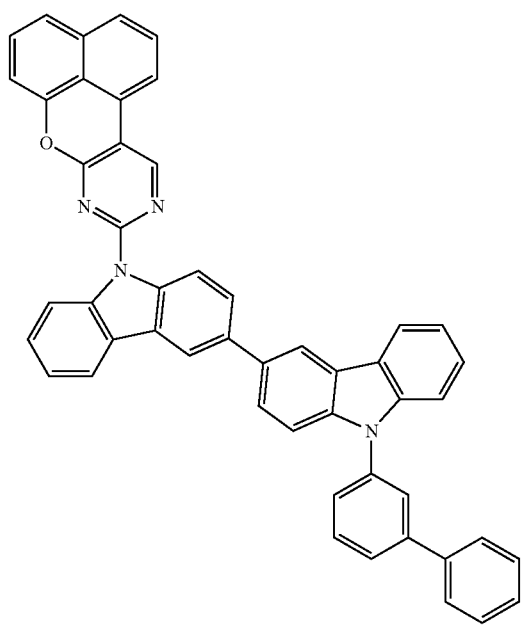
Formula 33
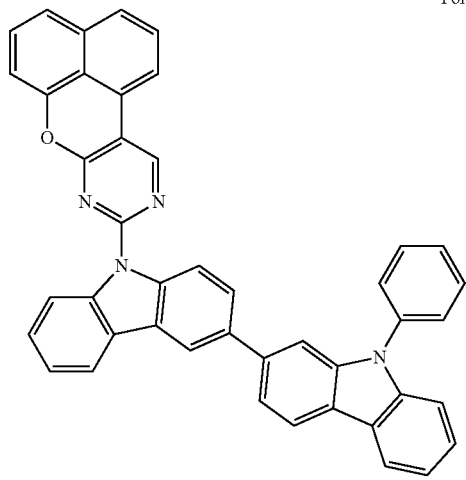
Formula 34
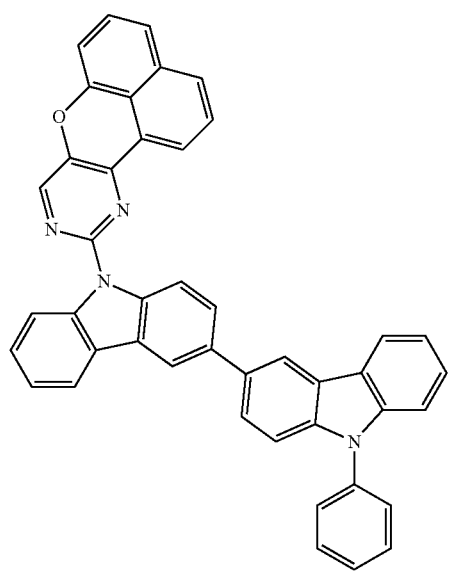

Formula 35
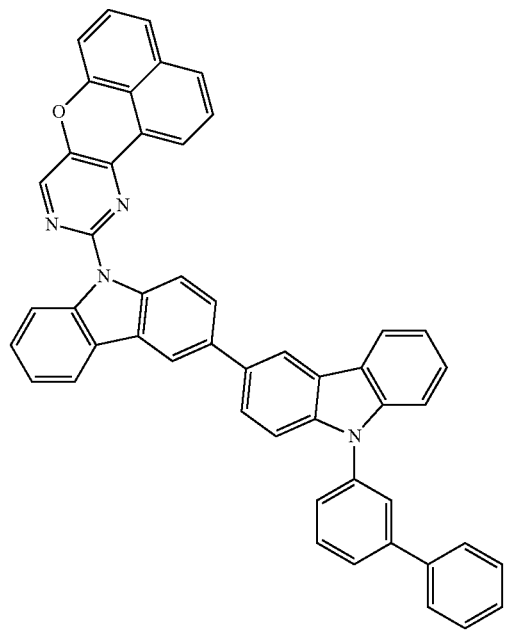
Formula 36
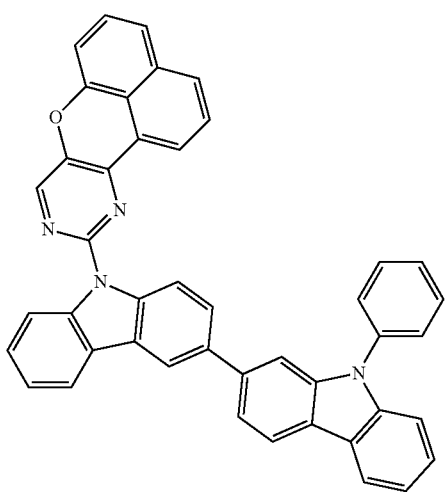
Formula 37
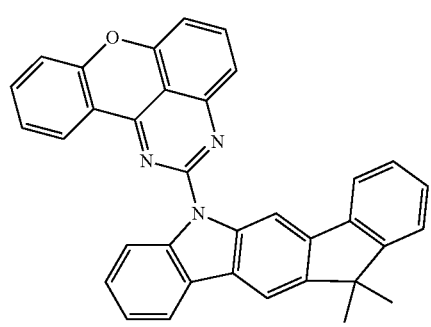
Formula 38
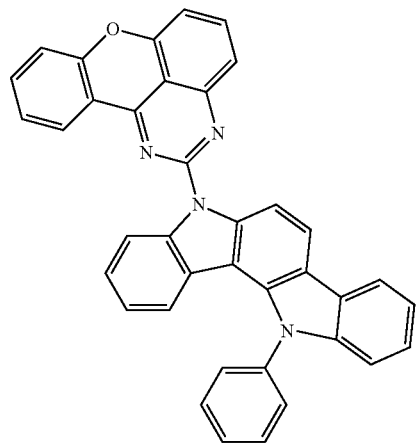
Formula 39
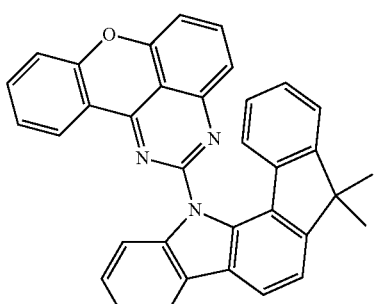
Formula 40
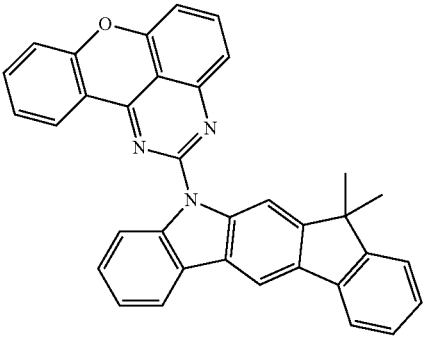
Formula 41
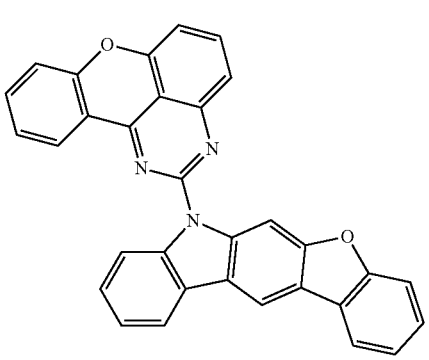

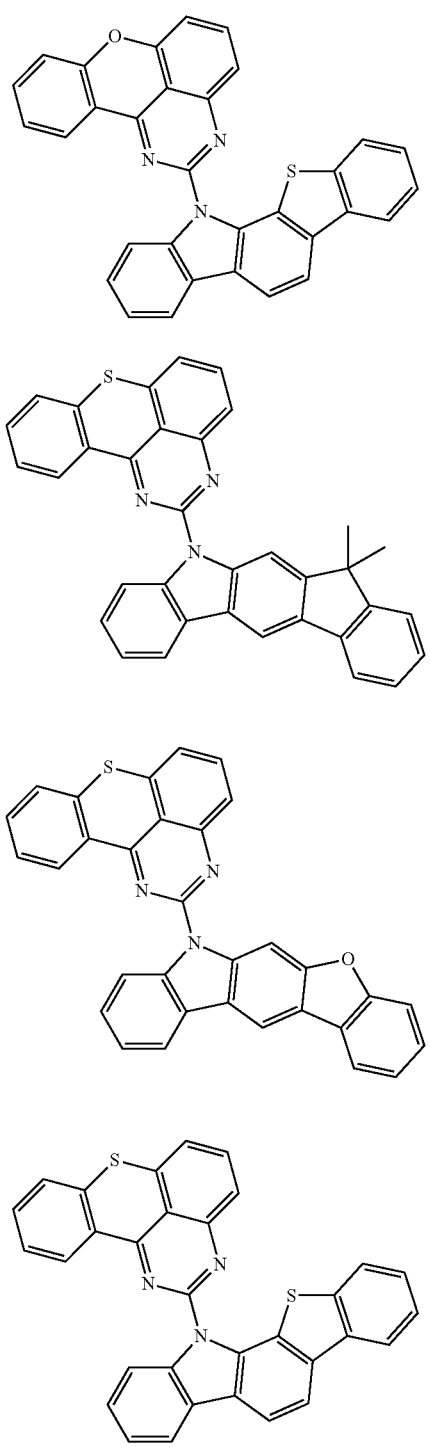
Formula 42
Formula 43
Formula 44
Formula 45
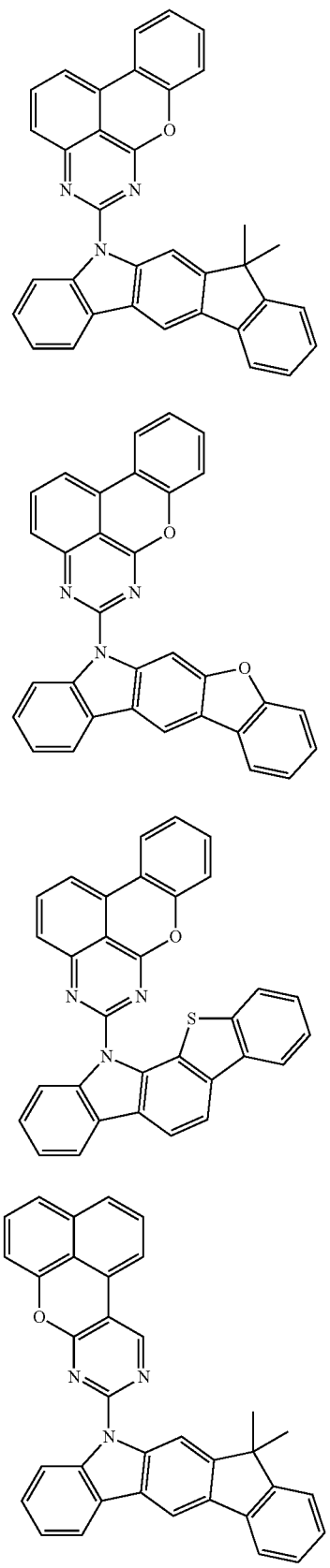
Formula 46
Formula 47
Formula 48
Formula 49

Formula 50
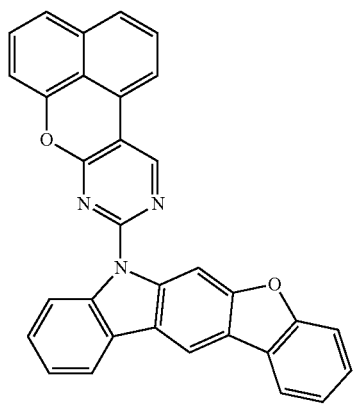
Formula 51
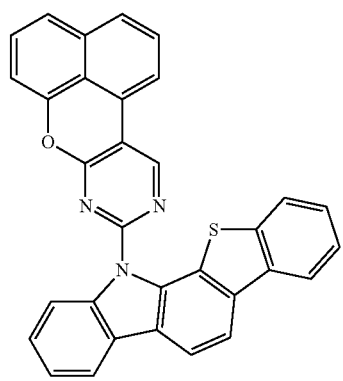
Formula 52
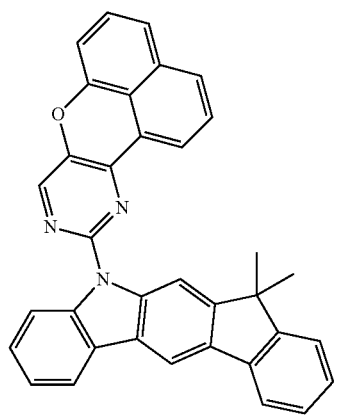
Formula 53
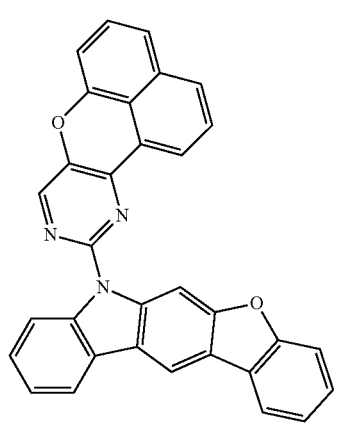
Formula 54
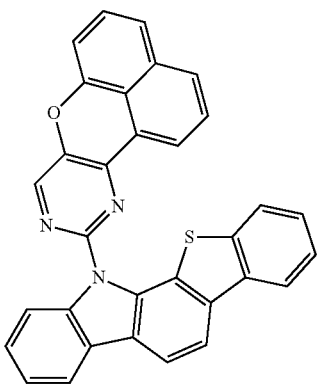
Formula 55
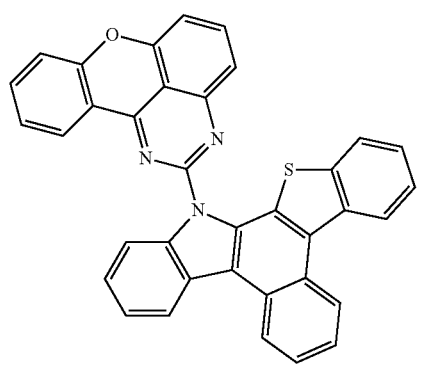
Formula 56
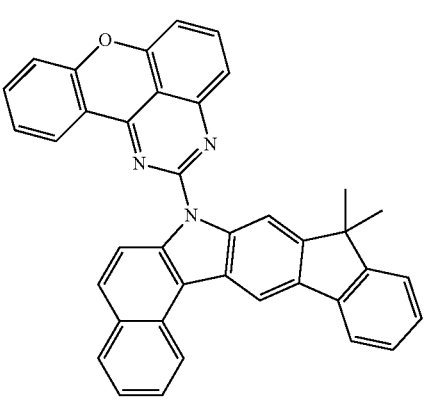
Formula 57
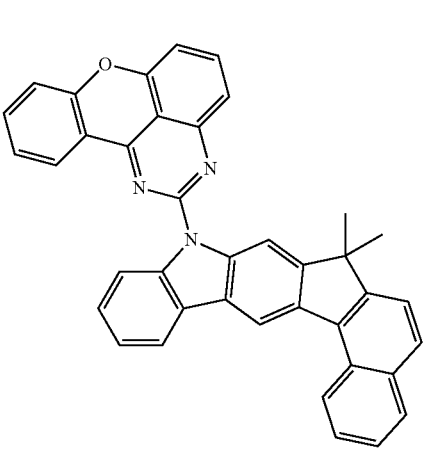

Formula 58
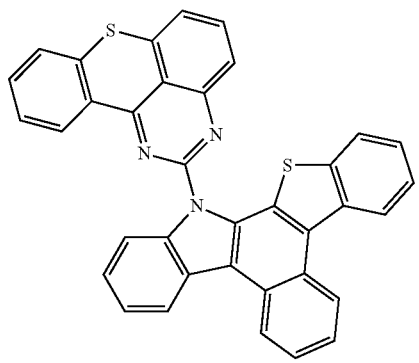
Formula 59
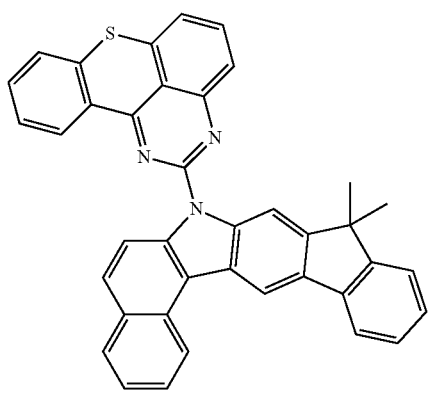
Formula 60
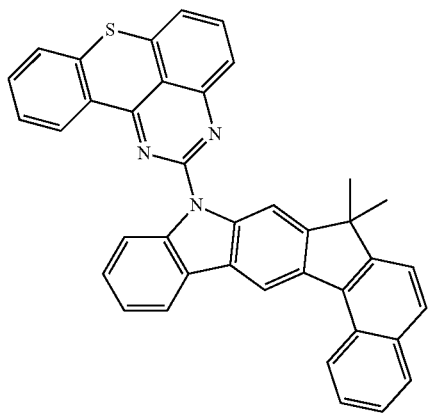
Formula 61
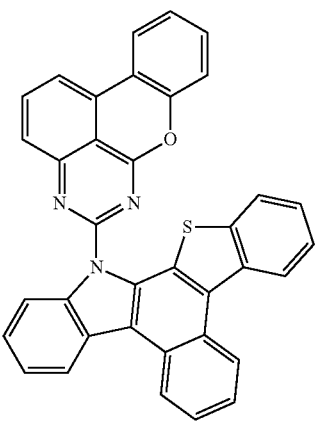
Formula 62
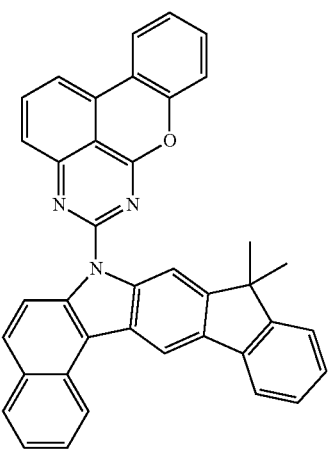
Formula 63
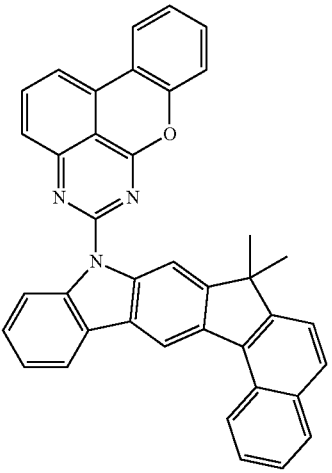

Formula 64
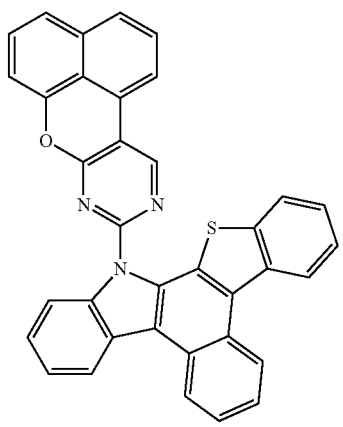
Formula 65
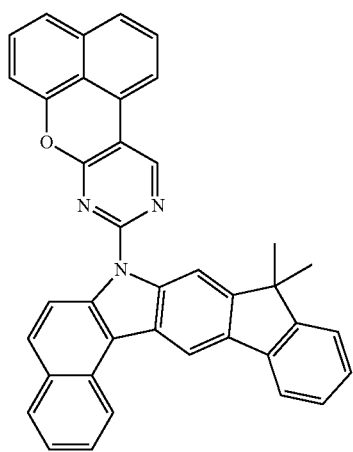
Formula 66
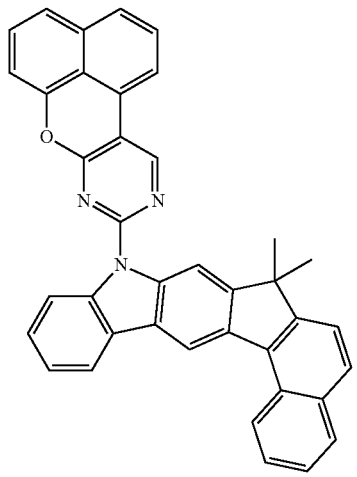
Formula 67
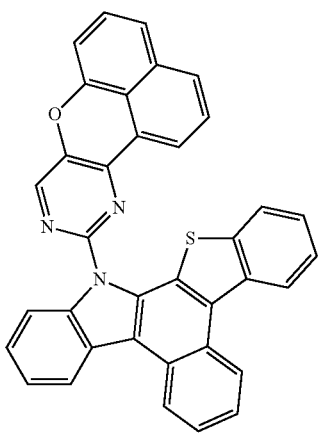
Formula 68
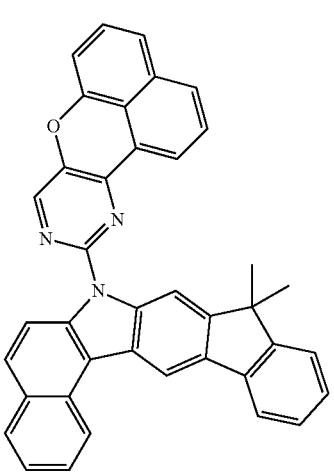
Formula 69
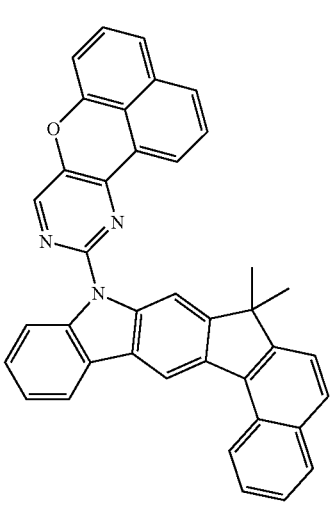

-continued
Formula 70
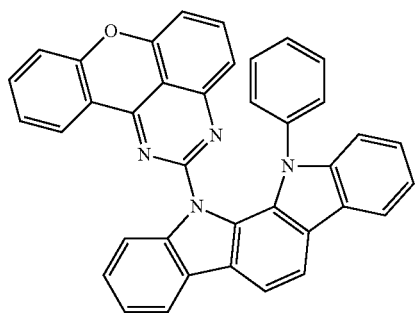
Formula 71
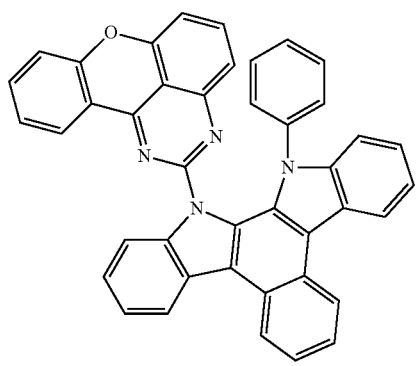
Formula 72
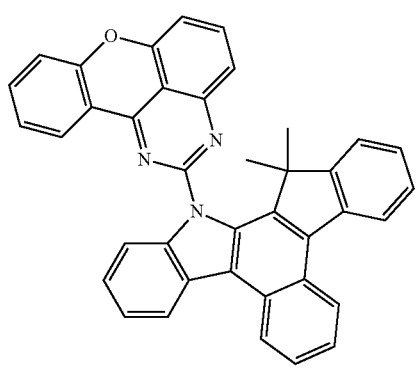
Formula 73
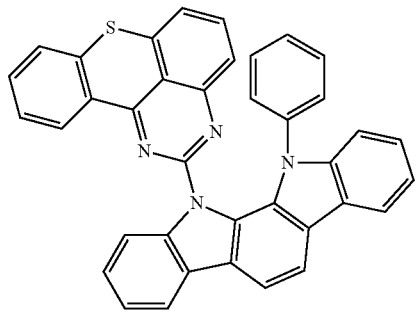
-continued
Formula 74
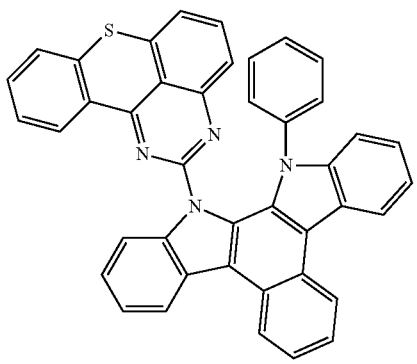
Formula 75
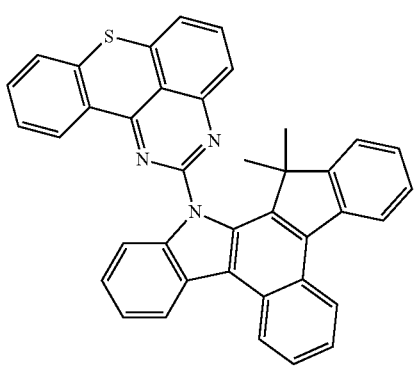
Formula 76
Formula 77

Formula 78
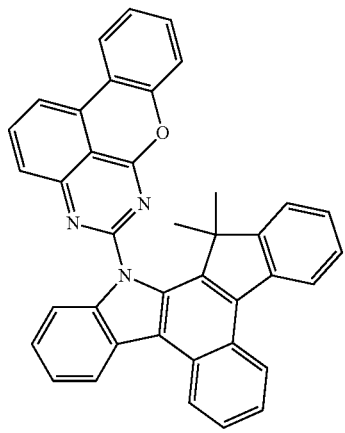
Formula 79
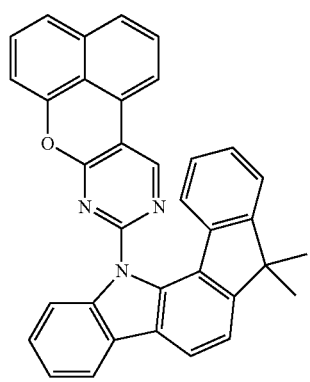
Formula 80
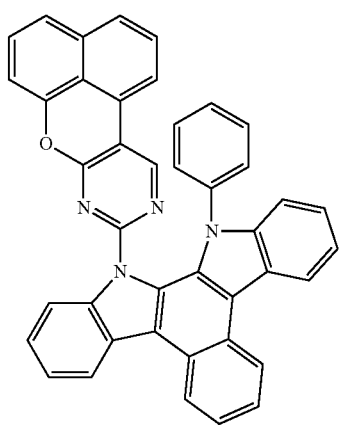
Formula 81
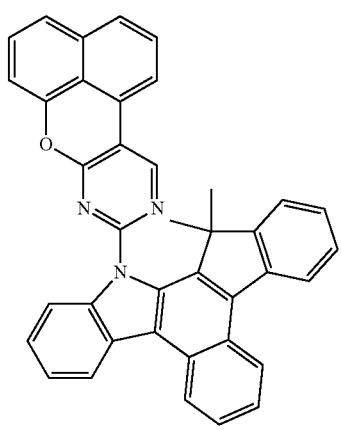
Formula 82
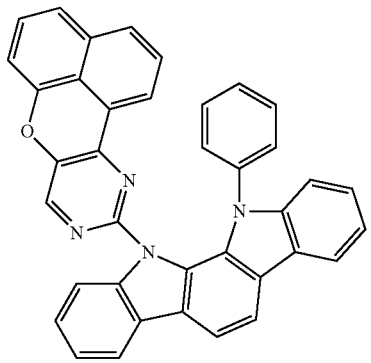
Formula 83
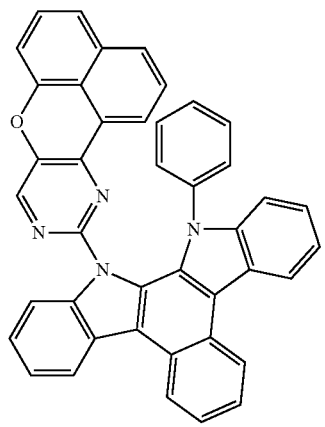
Formula 84
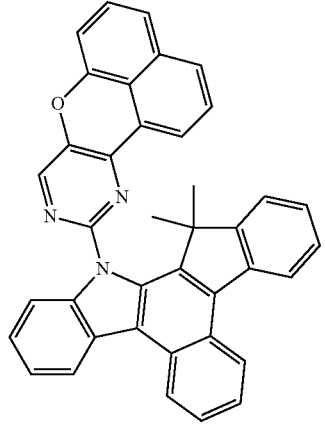
Formula 85
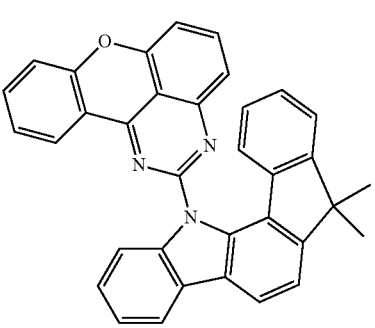

Formula 86
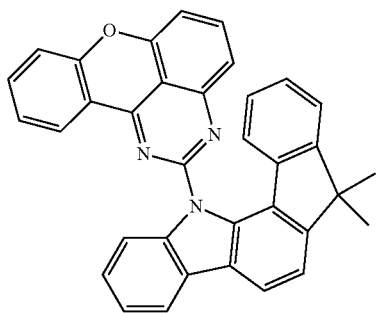
Formula 87
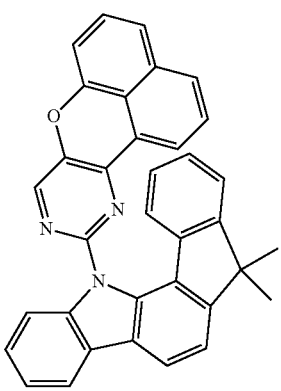
Formula 88
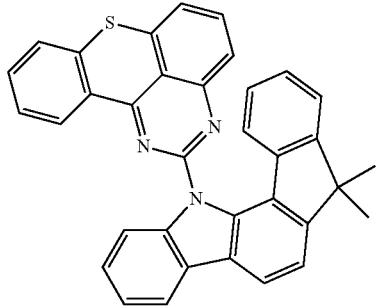
Formula 89
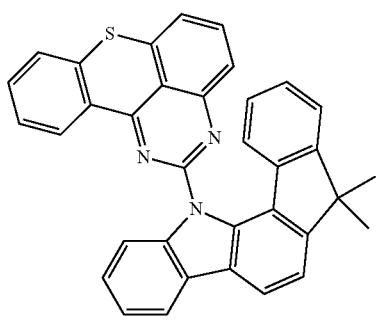
Formula 90
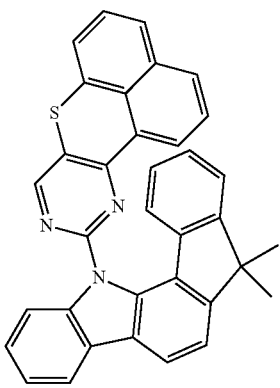
Formula 91
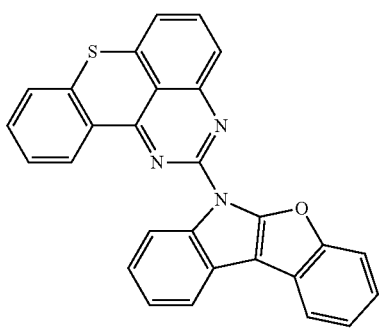
Formula 92
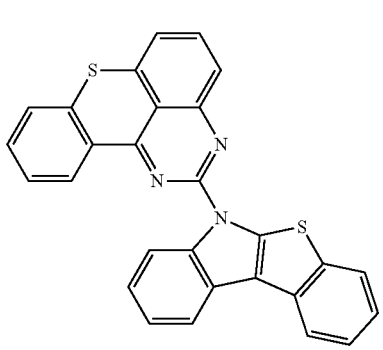
Formula 93
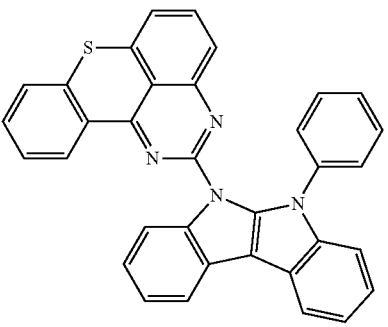

Formula 94
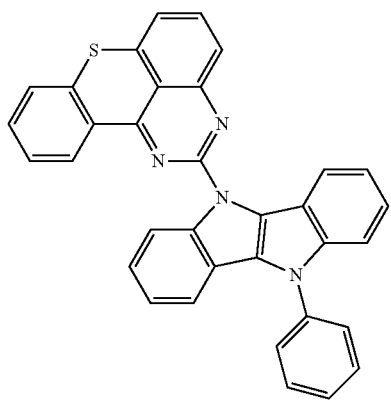
Formula 95
Formula 96
Formula 97
Formula 98
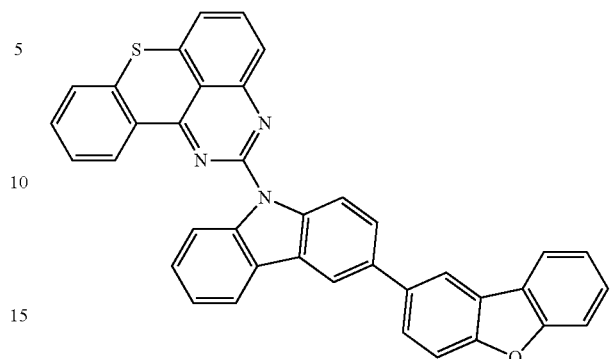
Formula 99
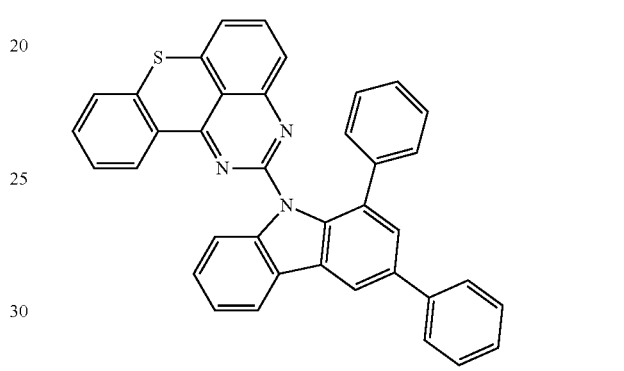
Formula 100
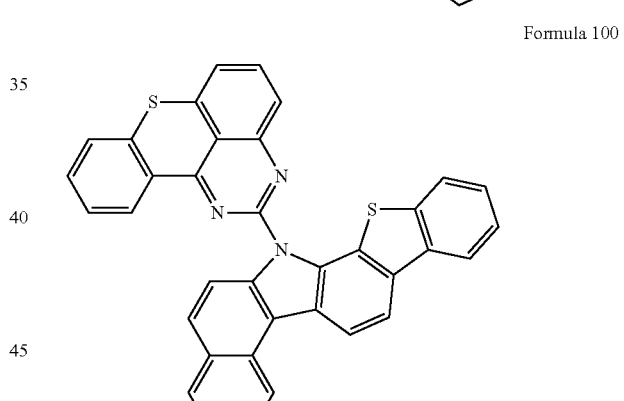
Formula 101
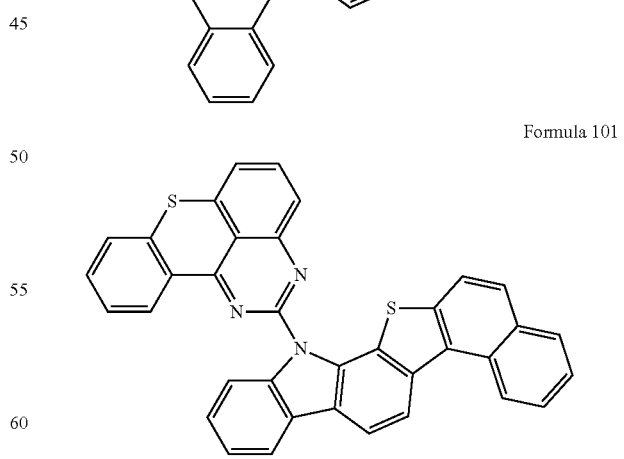

Formula 102
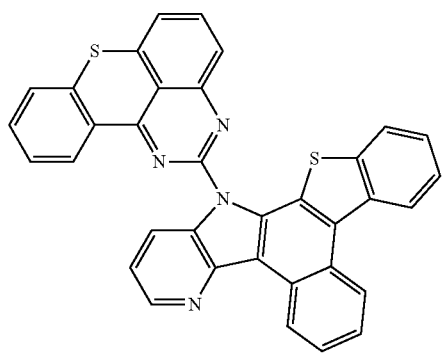
Formula 103
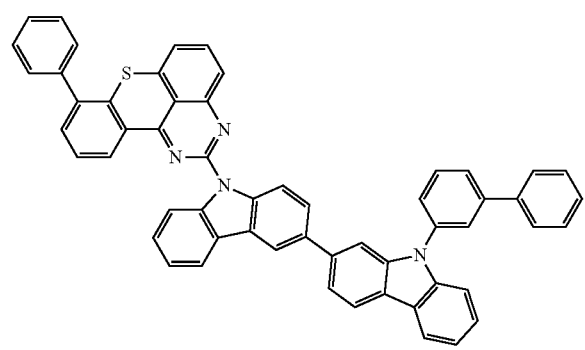
Formula 104
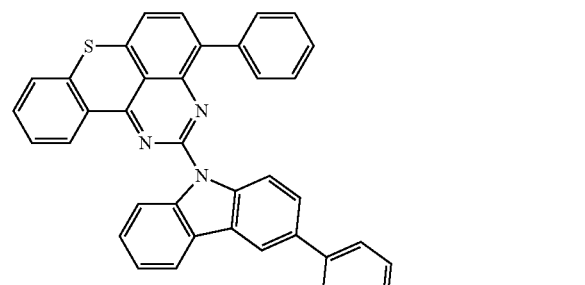
Formula 105
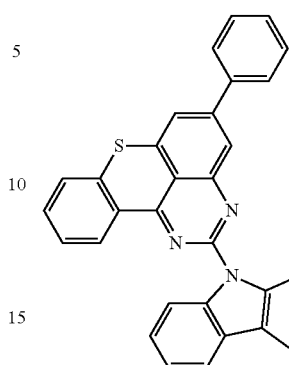
Formula 106
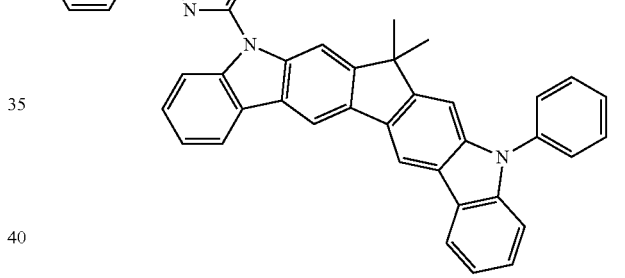
Formula 107
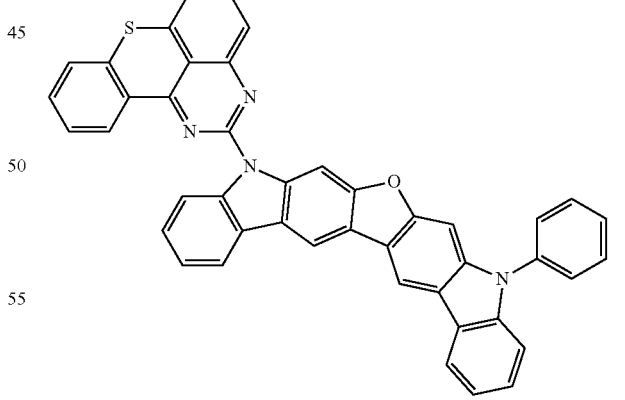

Formula 108
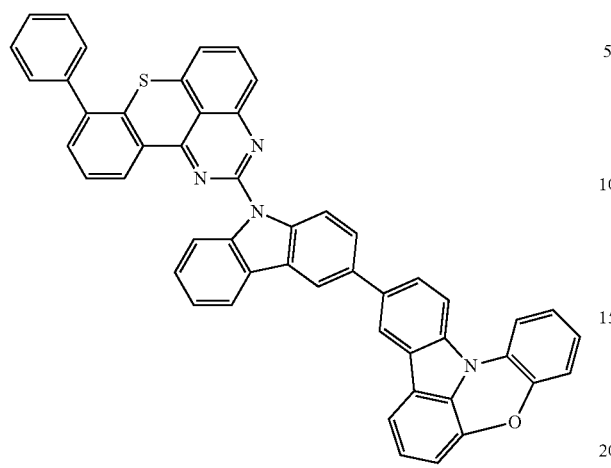
Formula 109
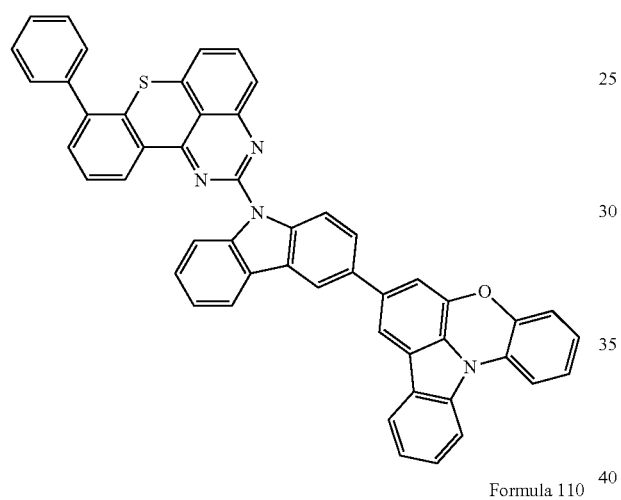
Formula 110
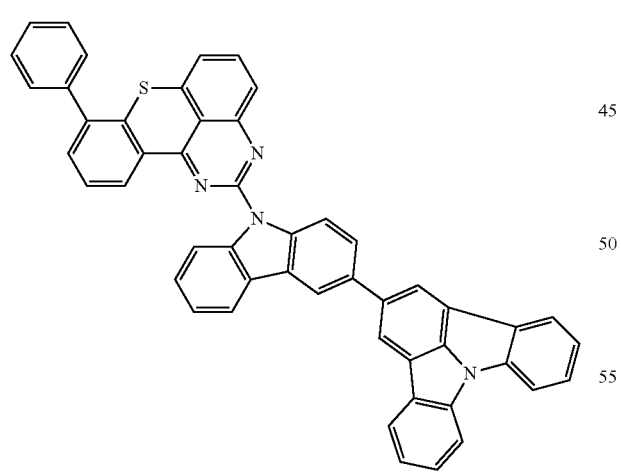
Formula 111
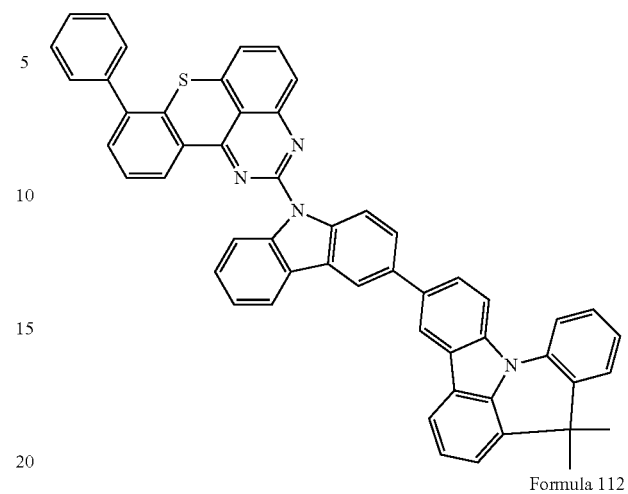
Formula 112
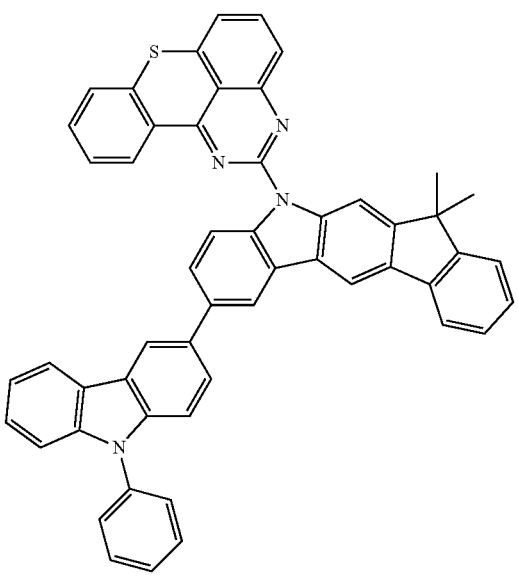
Formula 113
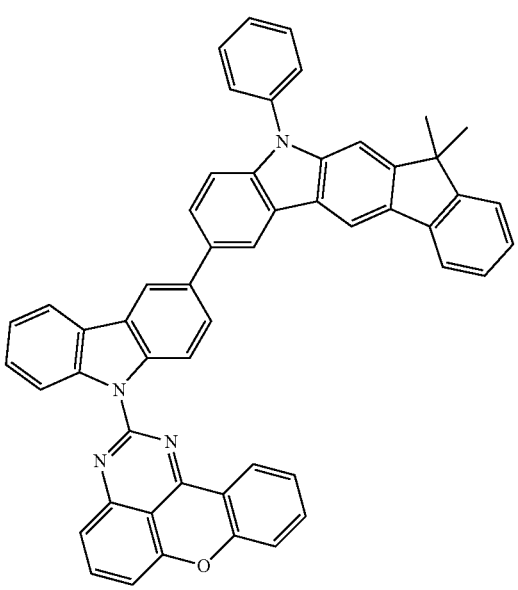

Formula 114

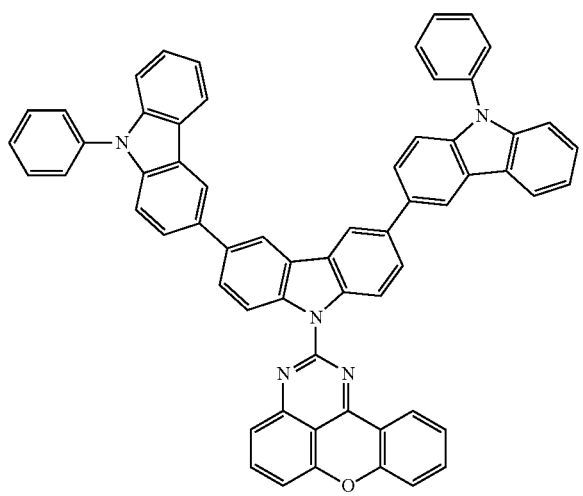

Scheme 1

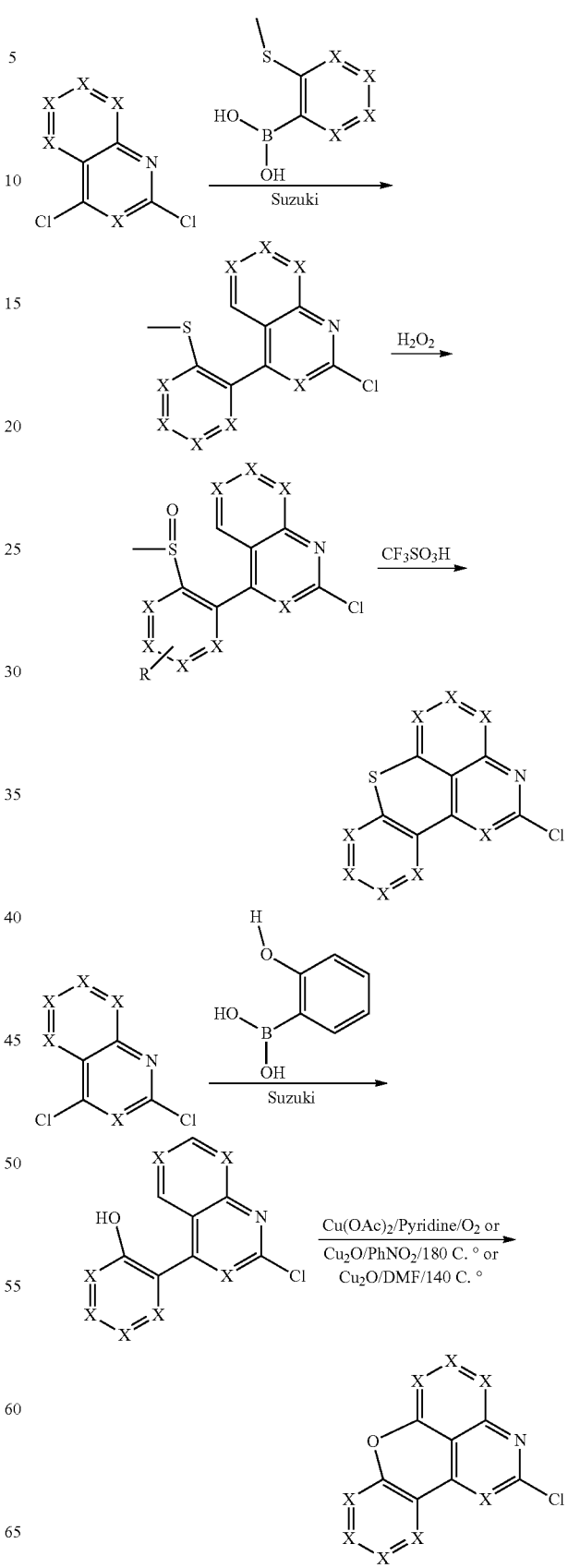

Preferred embodiments of compounds of the invention are recited specifically in the examples, these compounds being usable alone or in combination with further compounds for all purposes of the invention.

Provided that the conditions specified in Claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (I) in which, in a coupling reaction, a compound comprising at least one nitrogen-containing heterocyclic group, preferably a bridged quinazoline group, is joined to a compound comprising at least one carbazole group.

Suitable compounds having a carbazole group are in many cases commercially available, and the starting compounds detailed in the examples are obtainable by known processes, and so reference is made thereto.

These compounds can be reacted with further aryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

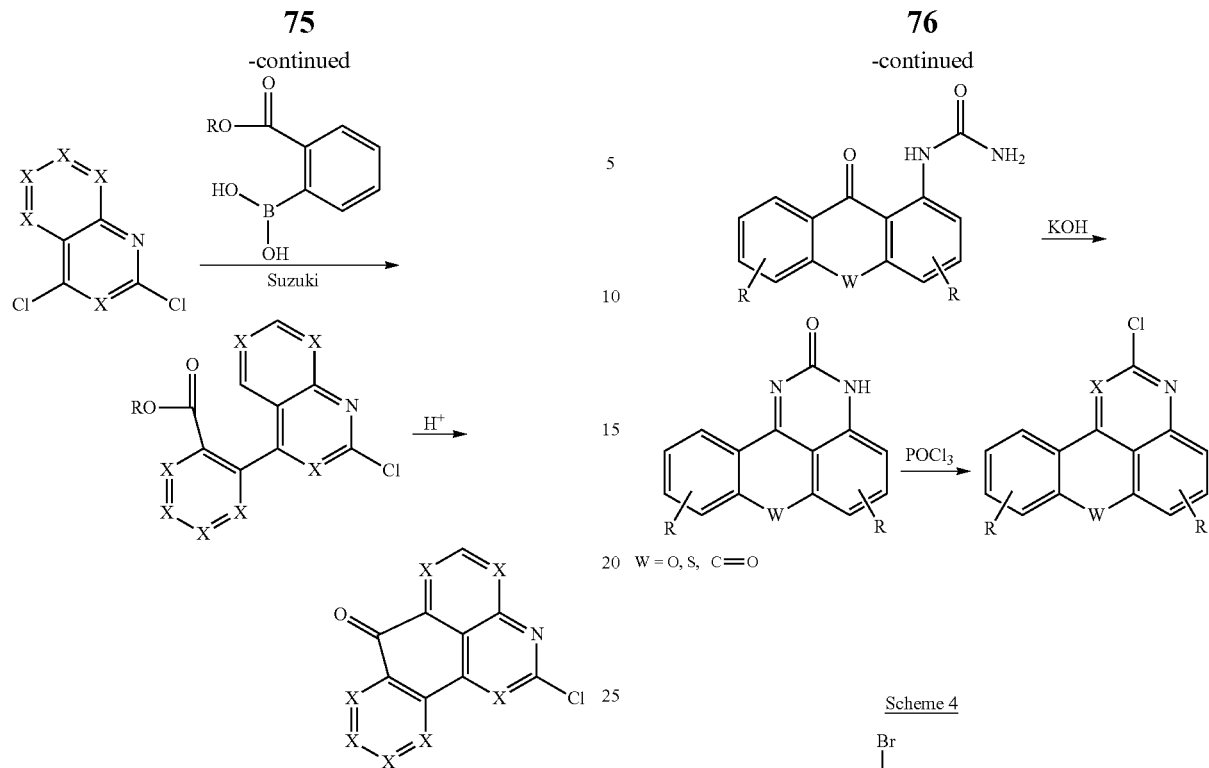
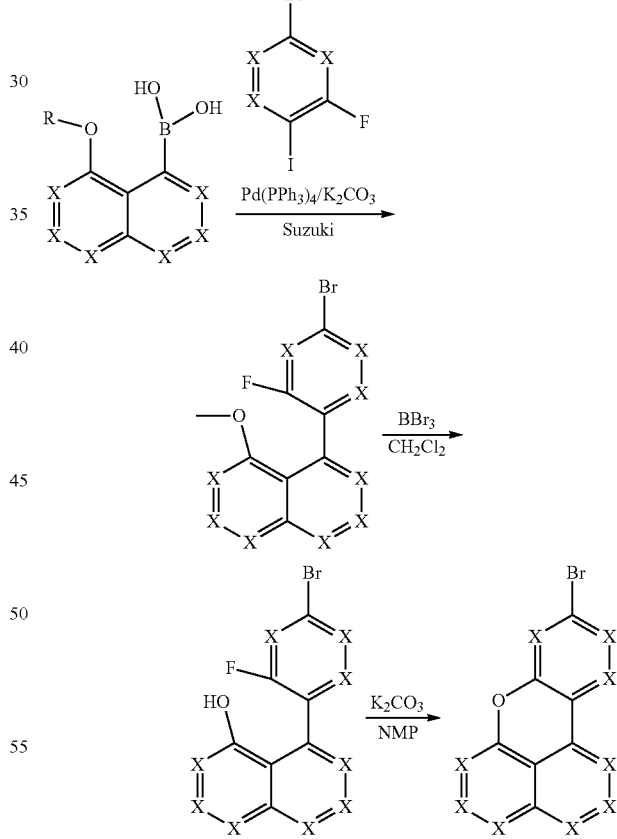
Scheme 4
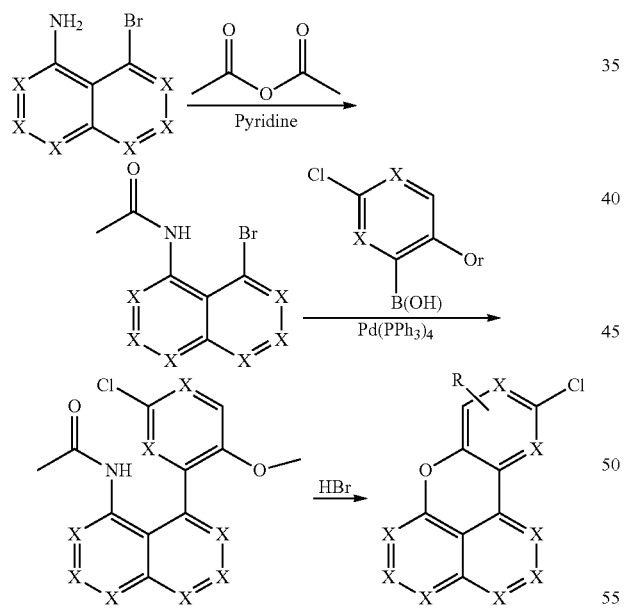
Scheme 2
Scheme 3
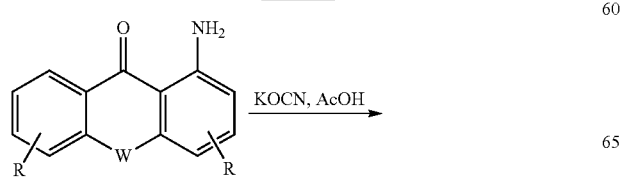

Scheme 5

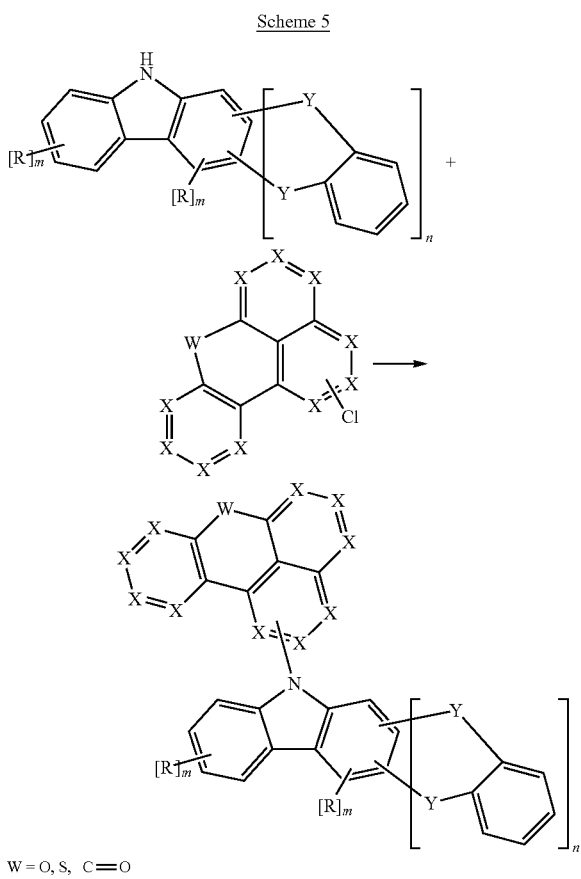

W = O, S, C=O

The definition of the symbols used in Schemes 1 to 5 corresponds essentially to those defined for formula (I), dispensing with numbering for reasons of clarity.

The chlorine or bromine substituents in the structures in the schemes shown above can be reacted in a coupling reaction with the appropriate carbazole group (CAB-1) unsubstituted on the nitrogen atom to give the compound of the invention.

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (I) in high purity, preferably more than 99% (determined by means of $^1$H NMR and/or HPLC).

The compounds of the invention may also have suitable substituents, for example relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration, in order to be able to process the compounds from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) or compounds of the invention, wherein one or more bonds of the compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, for example a fluorescent dopant, a phosphorescent dopant or a compound that exhibits TADF (thermally activated delayed fluorescence), especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode.

Preferably, the organically functional material is selected from the group consisting of fluorescent emitters, phosphorescent emitters, host materials, electron transport materials, electron injection materials, hole conductor materials, hole injection materials, electron blocker materials, hole blocker materials, wide band gap materials and n-dopants.

The present invention therefore also relates to a composition comprising at least one compound comprising structures of formula (I) or the preferred embodiments recited above and hereinafter and at least one further matrix material. According to a particular aspect of the present invention, the further matrix material has hole-transporting properties.

The present invention further provides a composition comprising at least one compound comprising at least one structure of formula (I) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO(eV)=((HEh*27.212)-0.9899)/1.1206$$

$$LUMO(eV)=((LEh*27.212)-2.0041)/1.385$$

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) or the preferred embodiments recited above and hereinafter and at least one phosphorescent emitter, the term "phosphorescent emitters" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and the as yet unpublished applications EP16179378.1 and EP16186313.9. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced below.

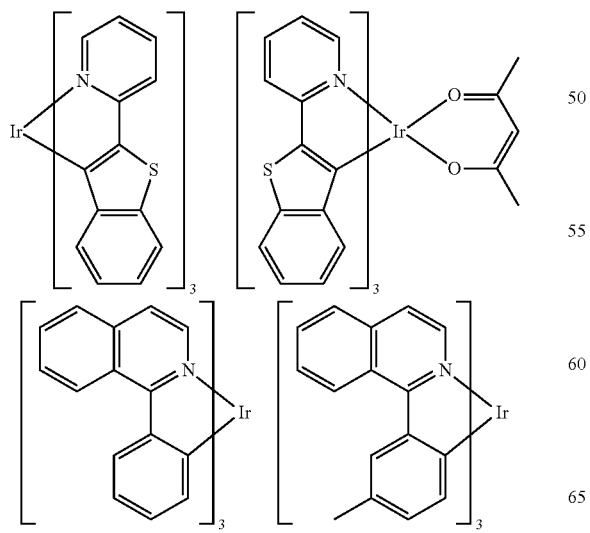

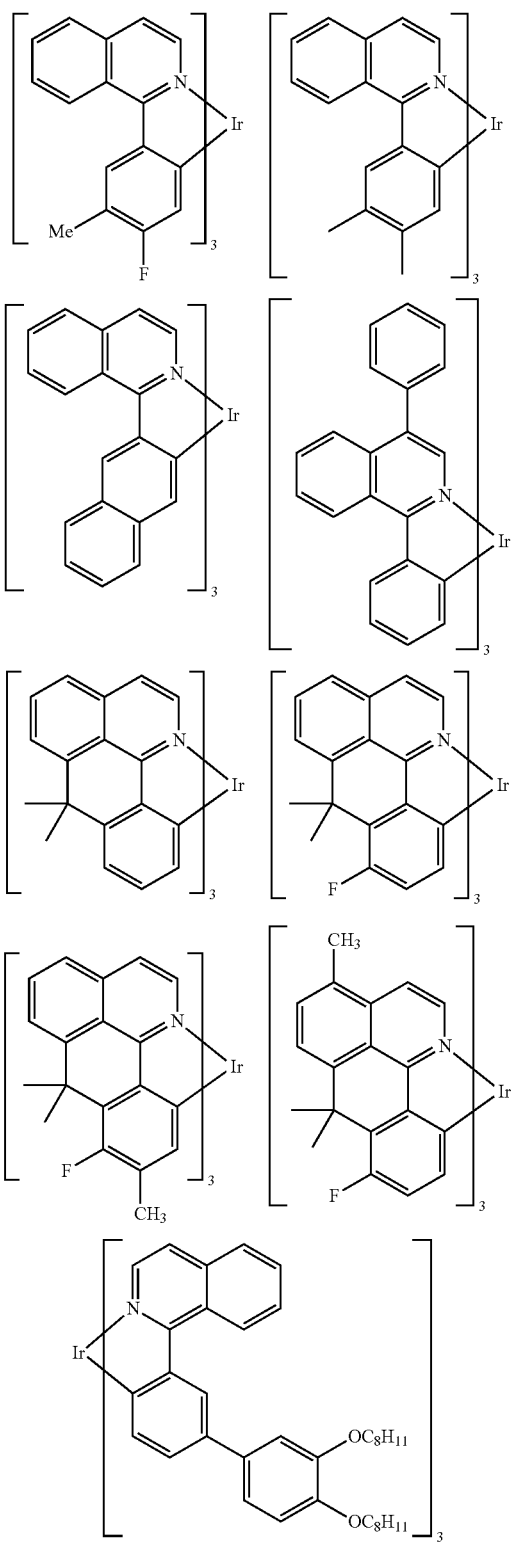

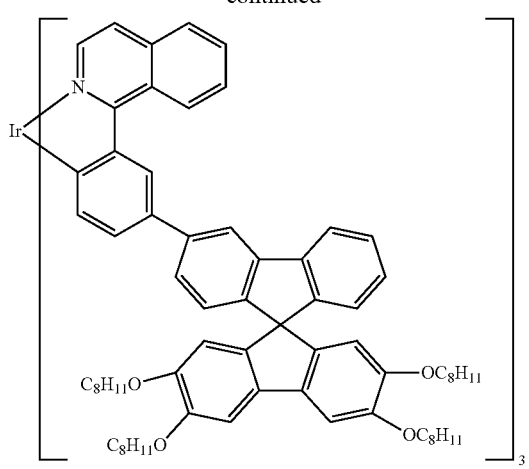
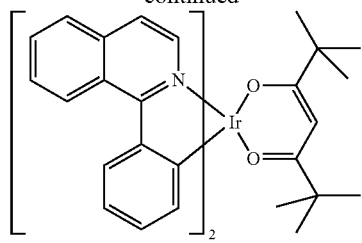
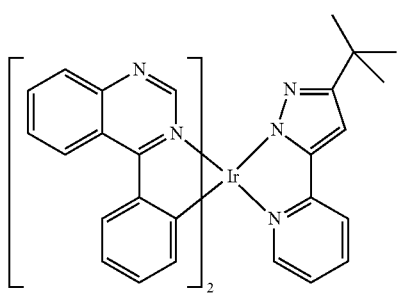
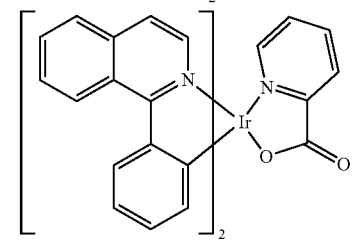
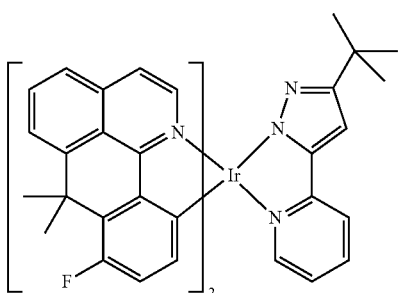
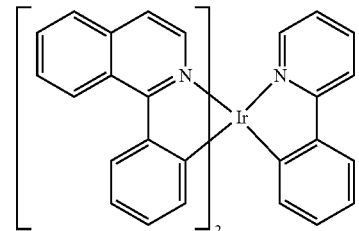
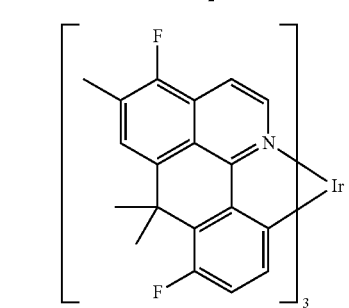
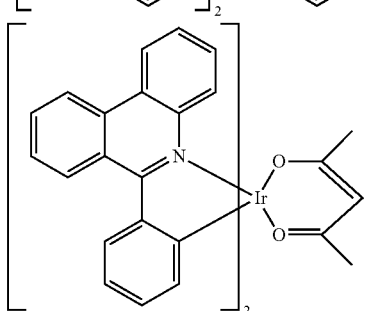
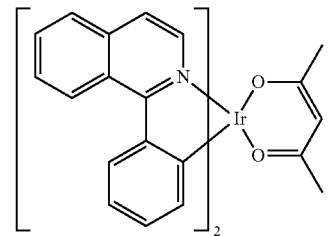
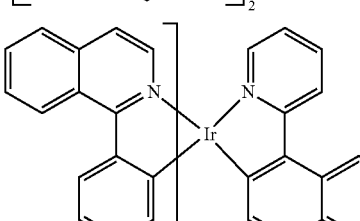
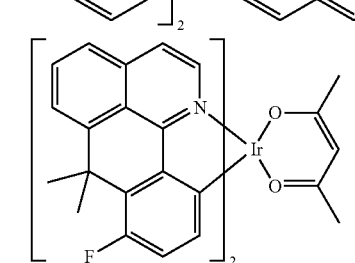
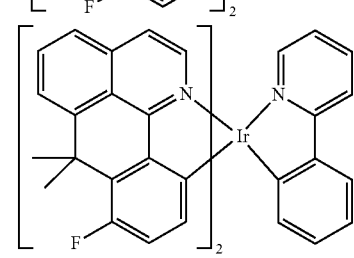

-continued
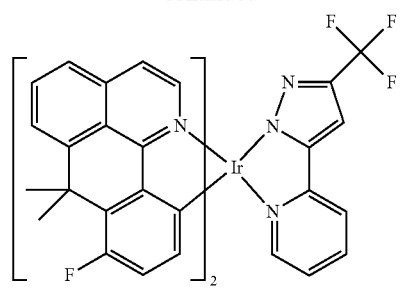
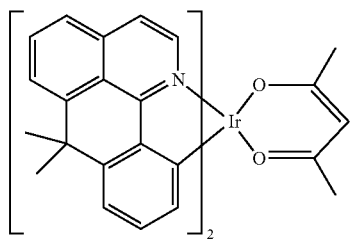
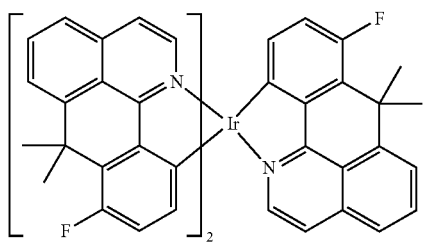
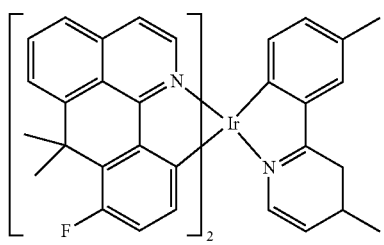
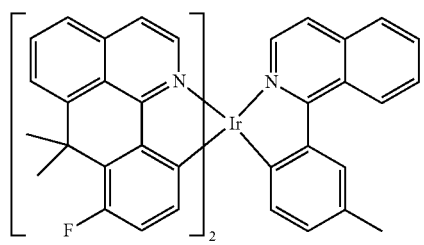
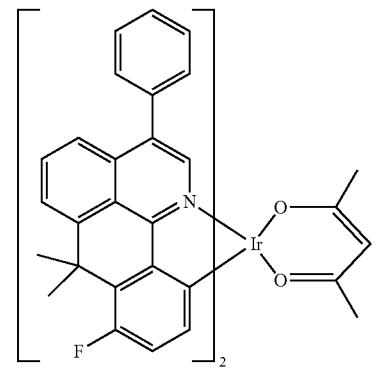
-continued
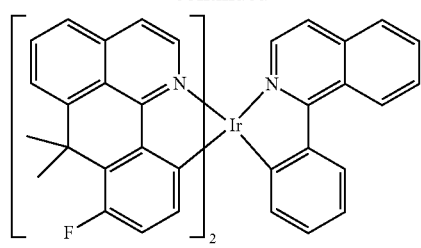
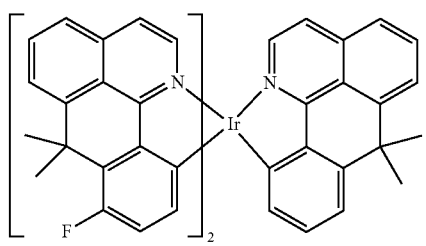
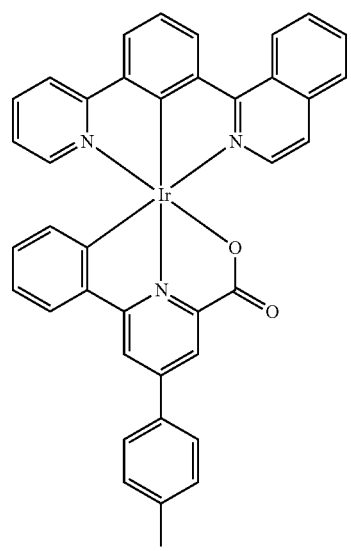
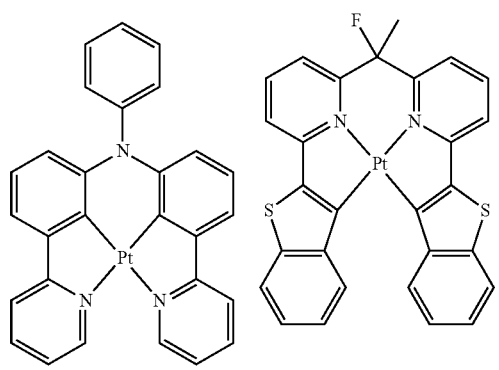

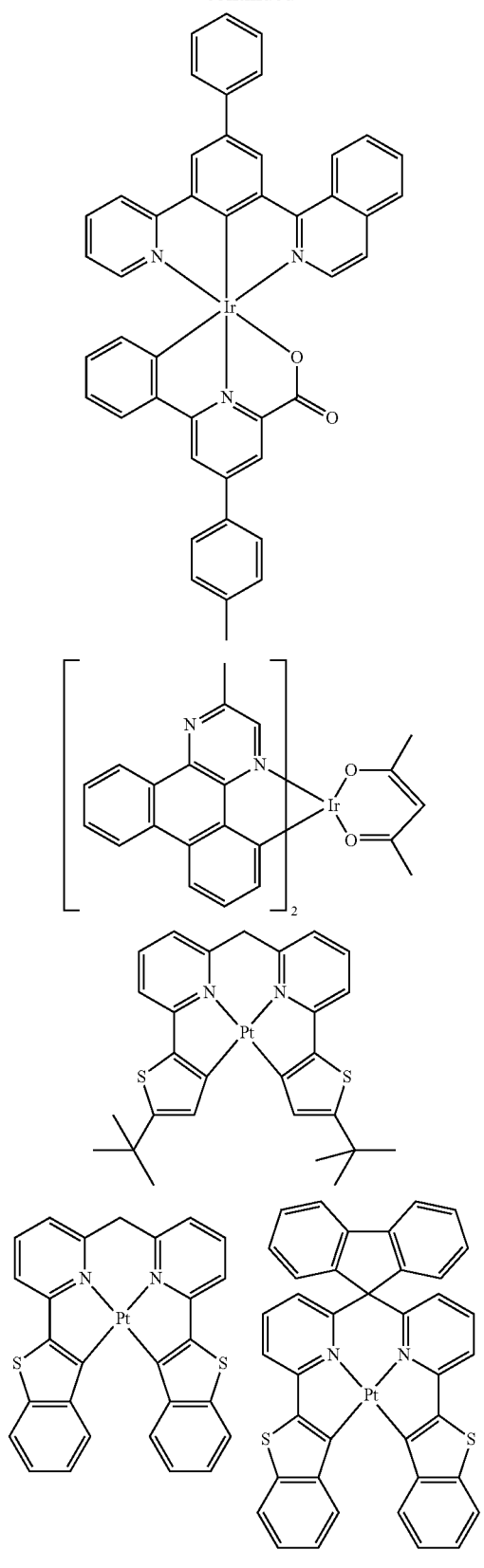

89
-continued
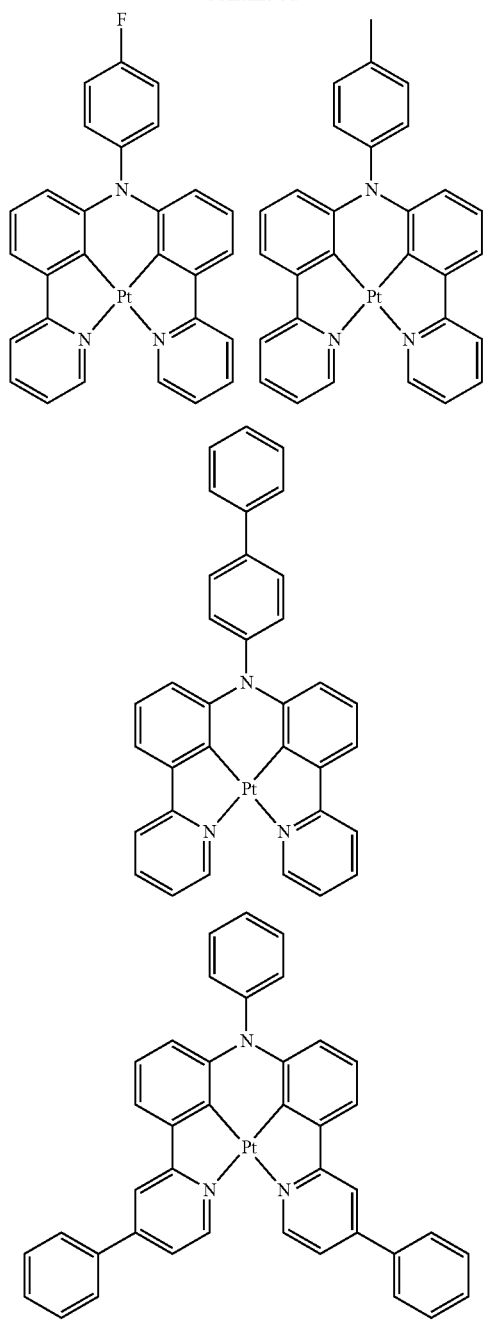
90
-continued
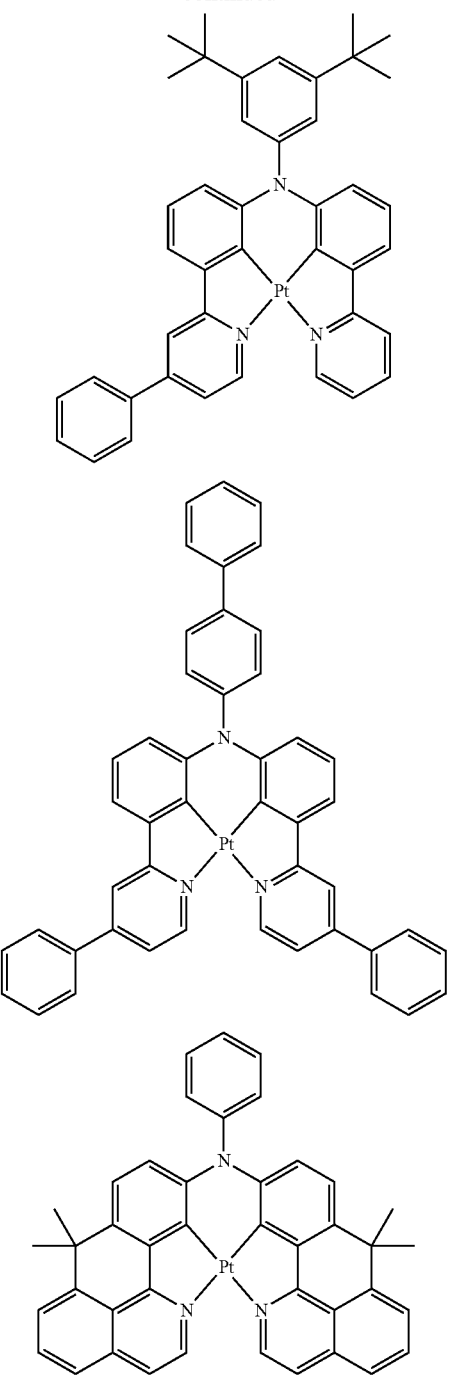

-continued
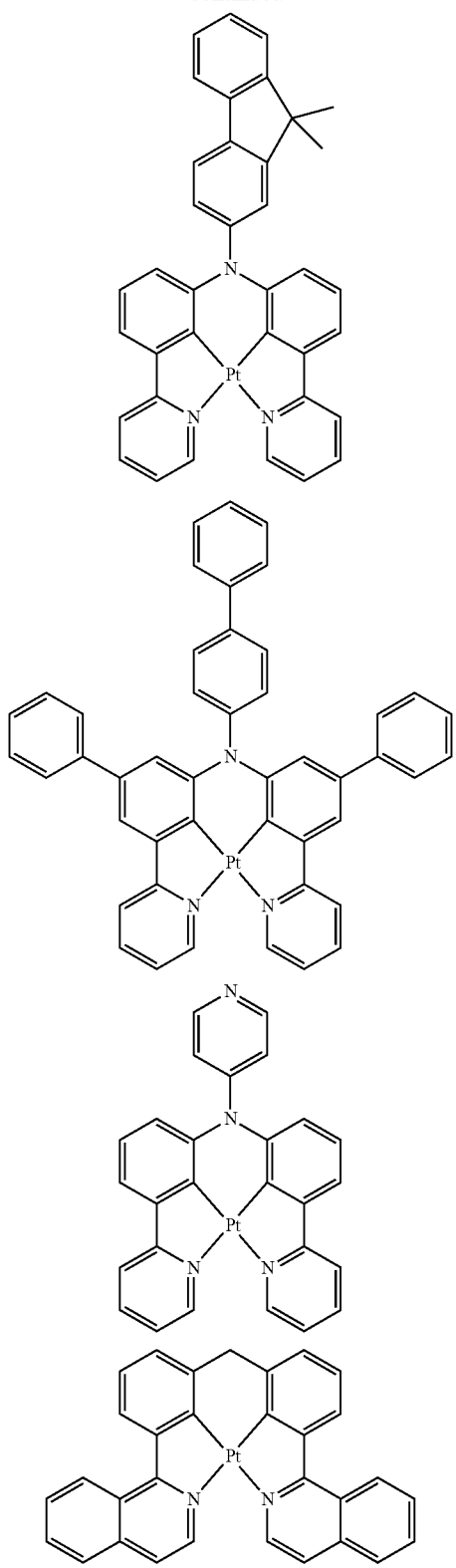
-continued
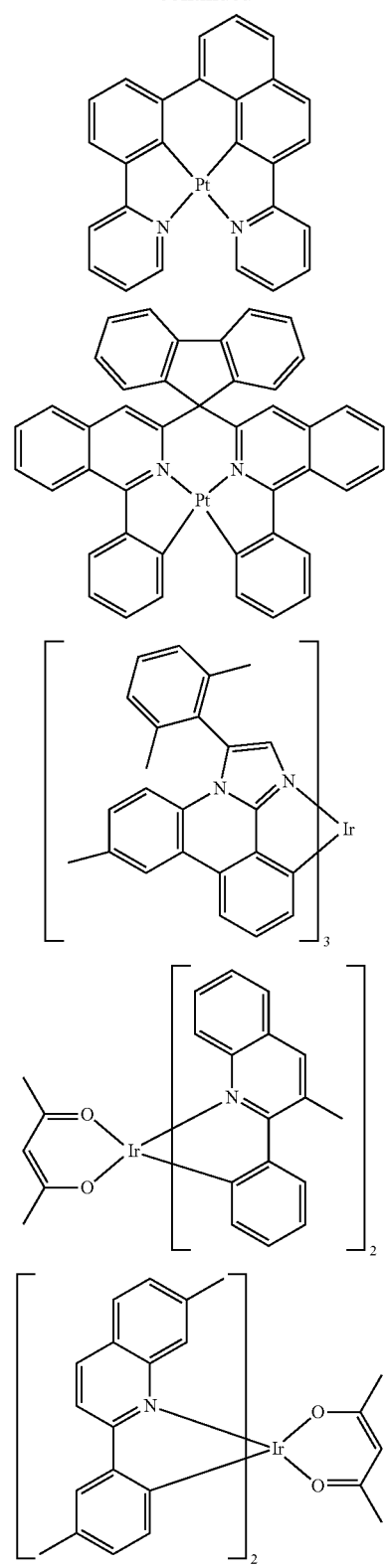

-continued
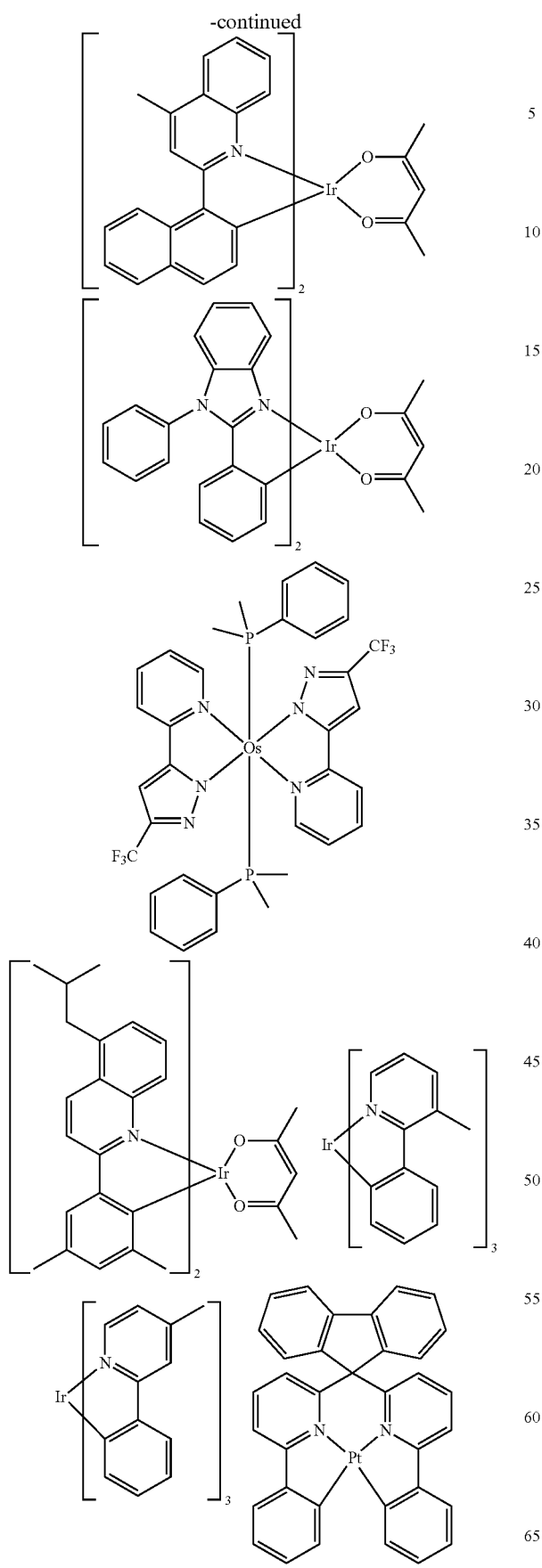
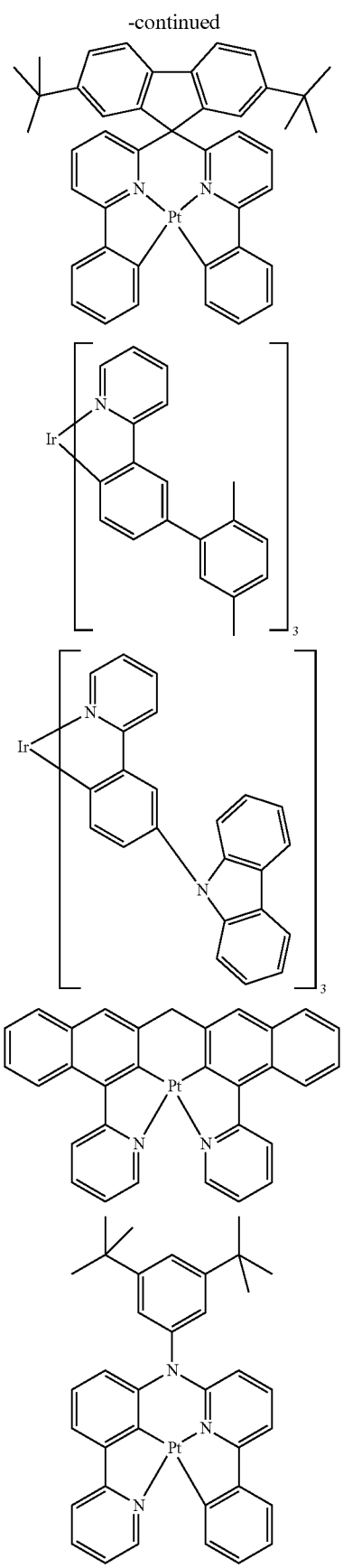

95
-continued
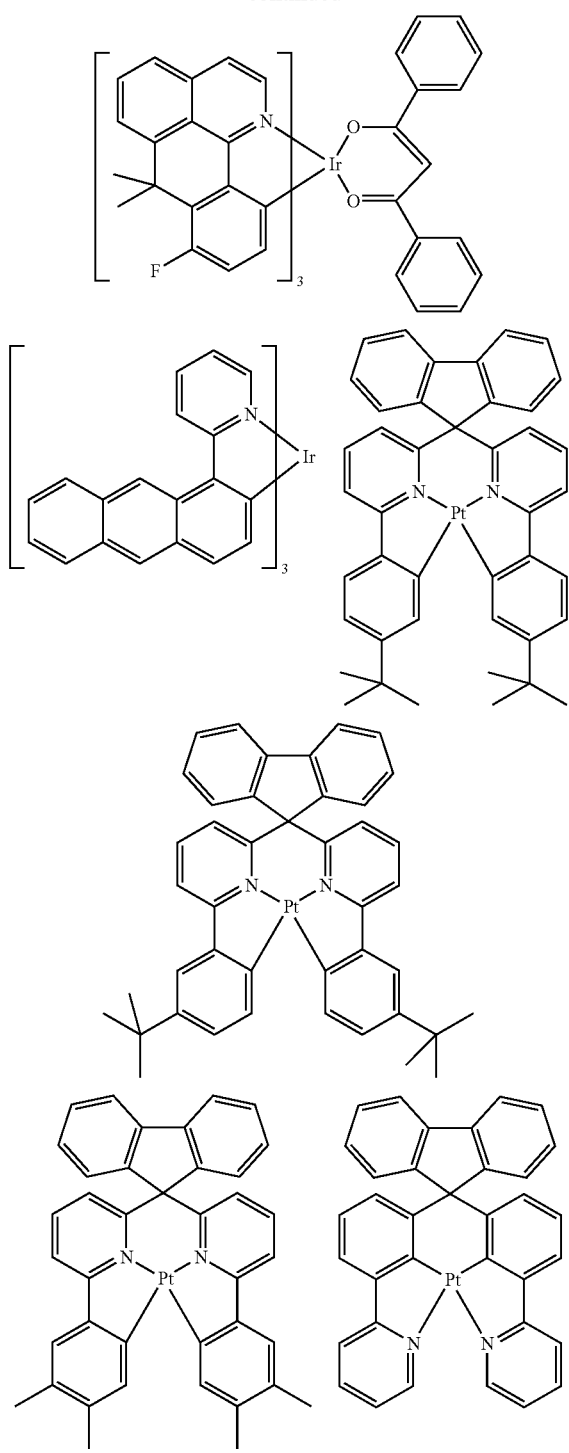
96
-continued
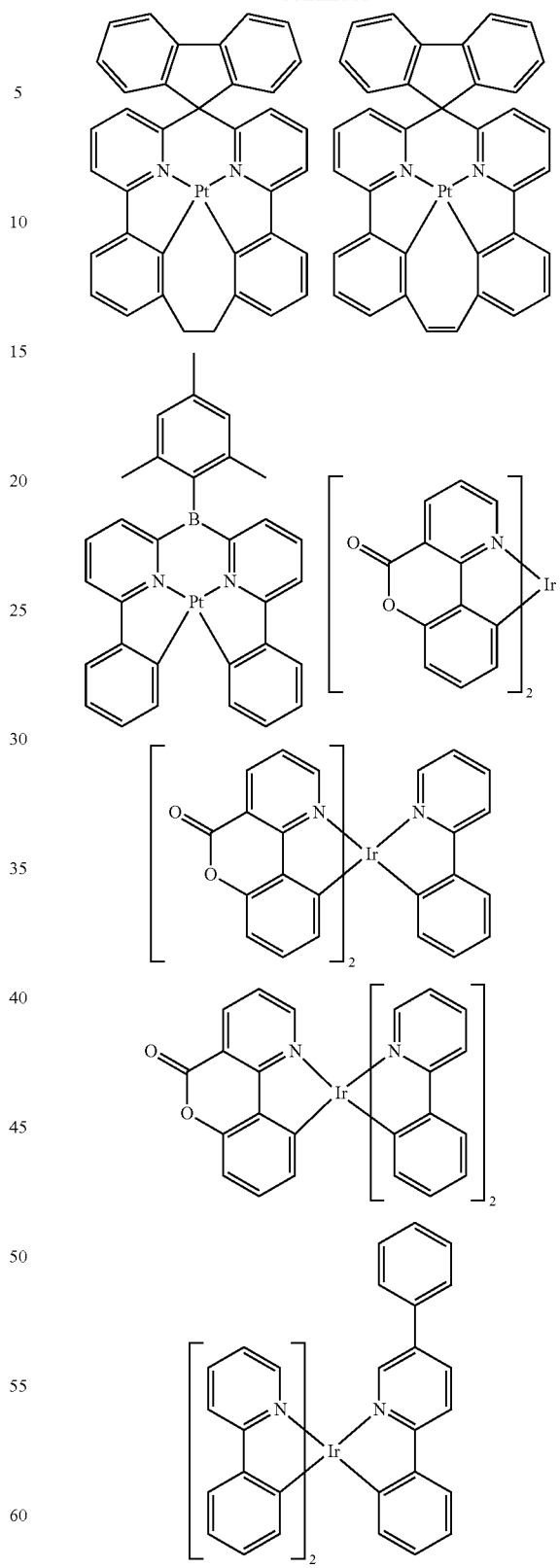

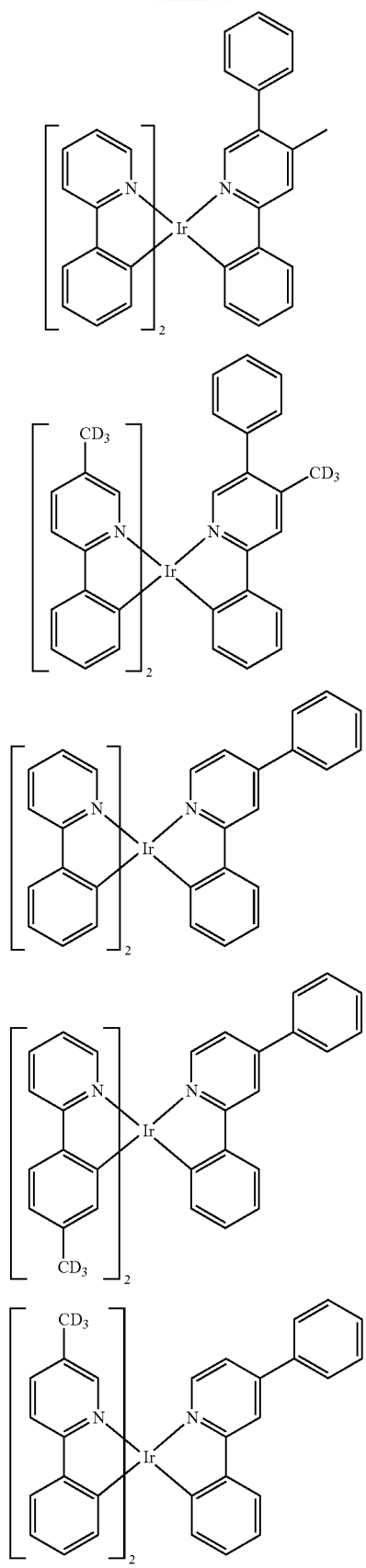
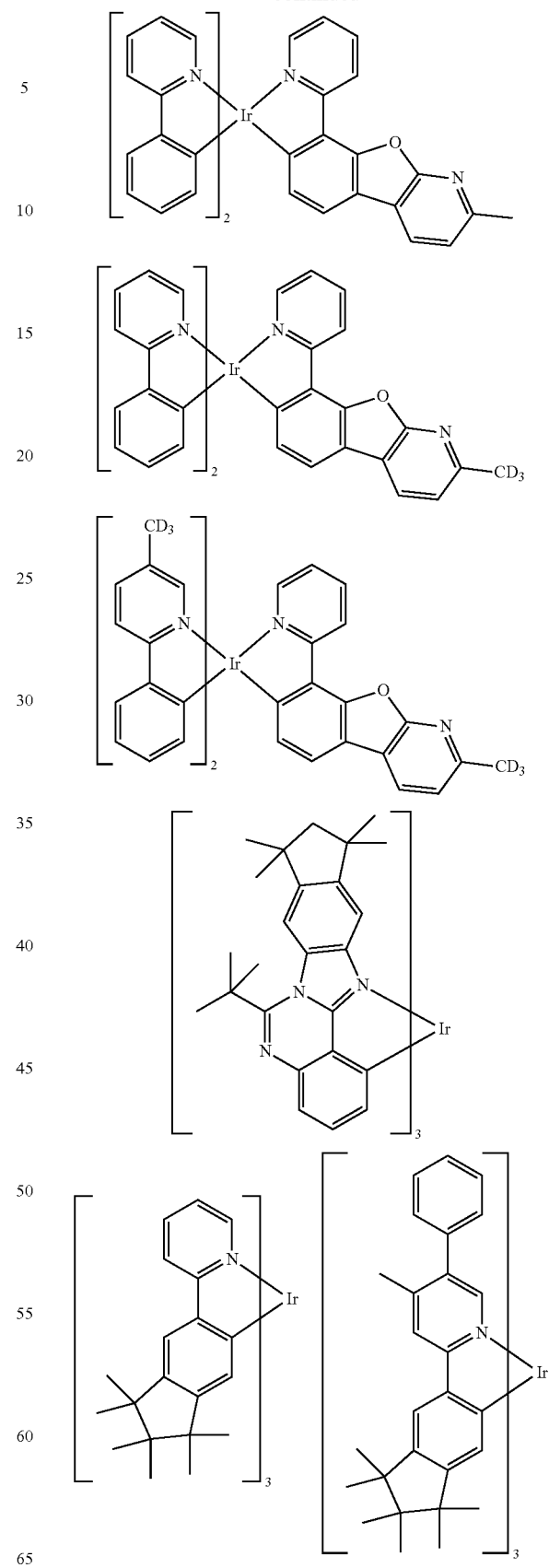

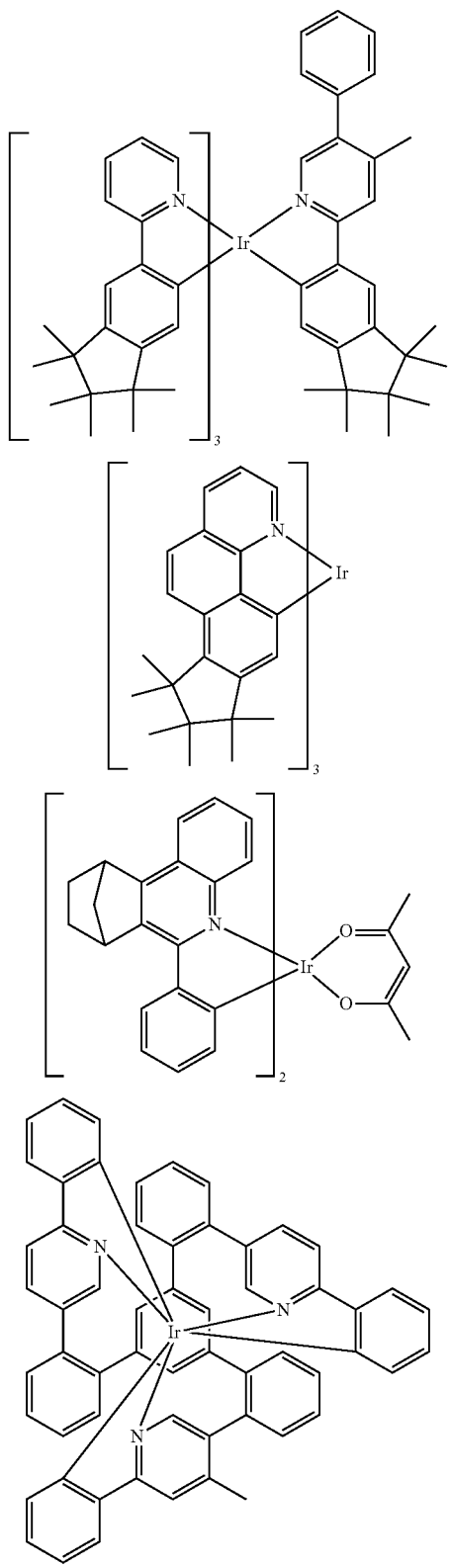
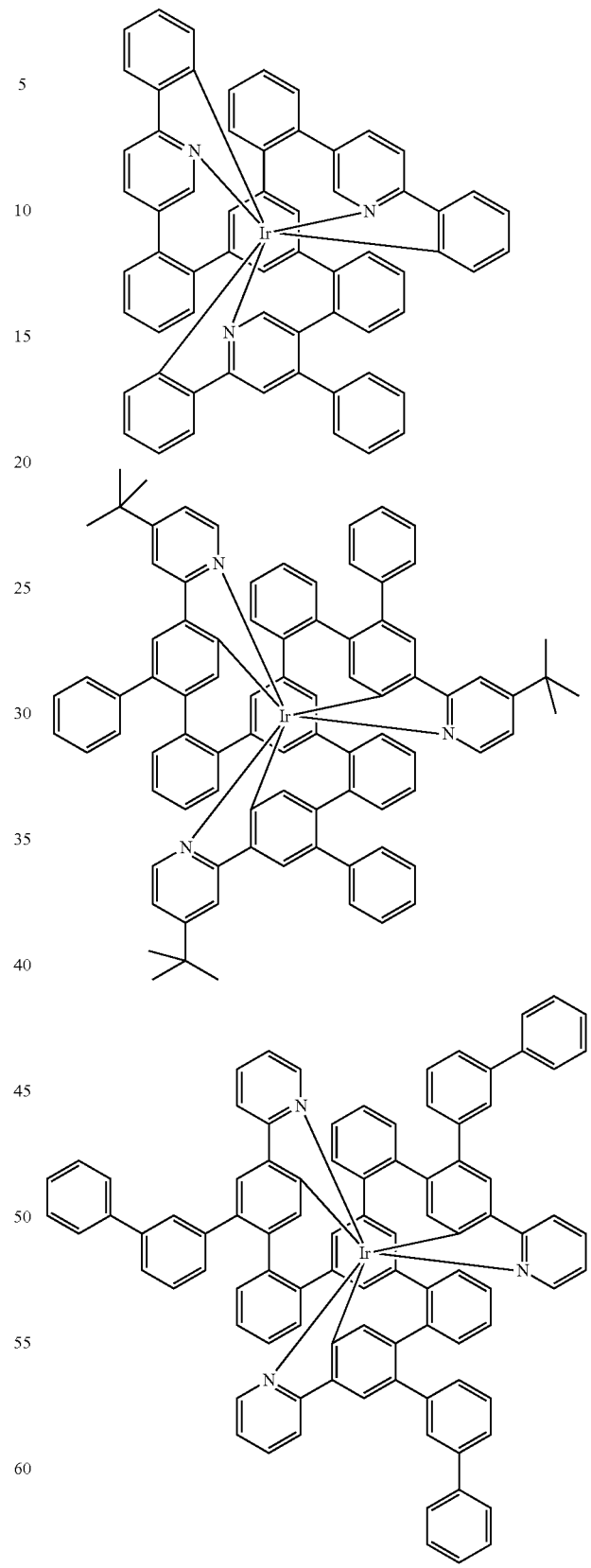

-continued

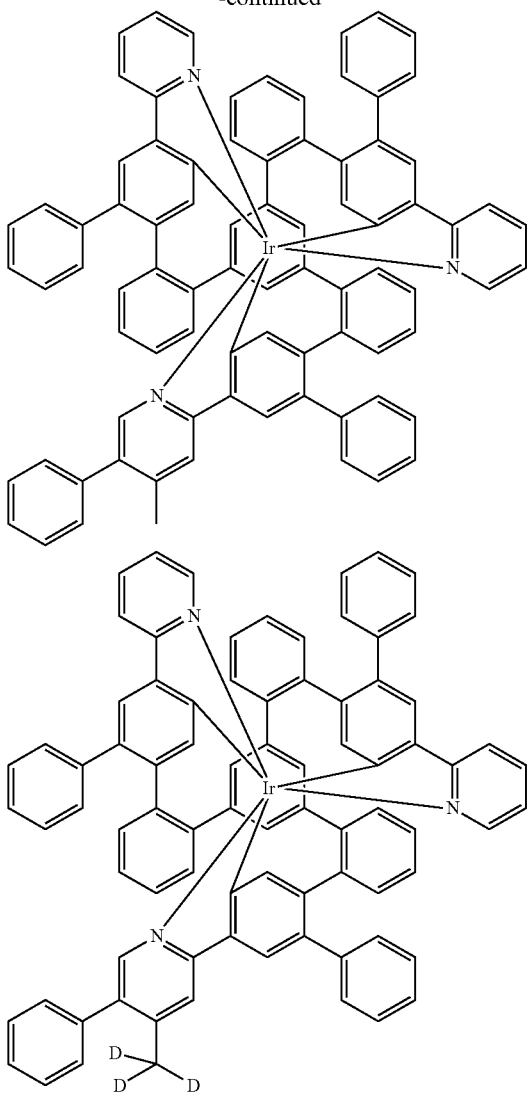

The above-described compound comprising structures of the formula (I) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (I). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices, preferably organic electroluminescent devices (OLEDs, PLEDs), especially phosphorescent OLEDs, containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Three-layer systems are especially preferred, where the three layers exhibit blue, green and orange or red emission, or systems having more than three emitting layers. Preference is further given to tandem OLEDs as well. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds of formula (I) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, 4-spirocarbazole derivatives, for example according to WO 2014/094963 or WO 2015/192939, or dibenzofuran derivatives, for example according to WO 2015/169412, WO 2016/015810, WO 2016/023608 or the as yet unpublished applications EP16158460.2 and EP16159829.7. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

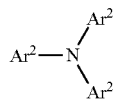

Formula (TA-1)

where $Ar^2$ is the same or different at each instance and is an aromatic or heteroaromatic ring system which has 6 to 40 carbon atoms and may be substituted in each case by one or more $R^2$ radicals, where two or more adjacent $R^2$ substituents may optionally form a mono- or polycyclic, aliphatic ring system which may be substituted by one or more $R^3$ radicals, where the symbol $R^2$ is as defined above, especially for formula (I). Preferably, $Ar^2$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^2$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^2$ groups are the same or different at each instance and are selected from the abovementioned $R^1$-1 to $R^1$-80 groups, more preferably $R^1$-1 to $R^1$-51.

In a preferred embodiment of the compounds of the formula (TA-1), at least one $Ar^2$ group is selected from a biphenyl group, which may be an ortho-, meta- or para-biphenyl group. In a further preferred embodiment of the compounds of the formula (TA-1), at least one $Ar^2$ group is selected from a fluorene group or spirobifluorene group, where these groups may each be bonded to the nitrogen atom in the 1, 2, 3 or 4 position. In yet a further preferred embodiment of the compounds of the formula (TA-1), at least one $Ar^2$ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one $Ar^2$ group is selected from a fluorene or spirobifluorene group, especially a 4-fluorene or 4-spirobifluorene group, and one $Ar^2$ group is selected from a biphenyl group, especially a para-biphenyl group, or a fluorene group, especially a 2-fluorene group, and the third $Ar^2$ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

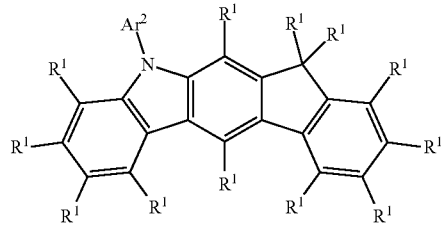

Formula (TA-2)

where $Ar^2$ and $R^1$ have the definitions listed above, especially for formulae (I) and/or (TA-1). Preferred embodiments of the $Ar^2$ group are the above-listed structures $R^1$-1 to $R^1$-80, more preferably $R^1$-1 to $R^1$-51.

A preferred embodiment of the compounds of the formula (TA-2) is the compounds of the following formula (TA-2a):

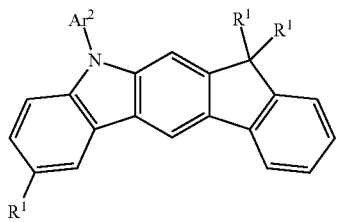

Formula (TA-2a)

where $Ar^2$ and $R^1$ have the definitions listed above, especially for formulae (I) and/or (TA-1). The two $R^1$ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two $R^1$ groups bonded to the indeno carbon atom are methyl groups. Further preferably, the R¹ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

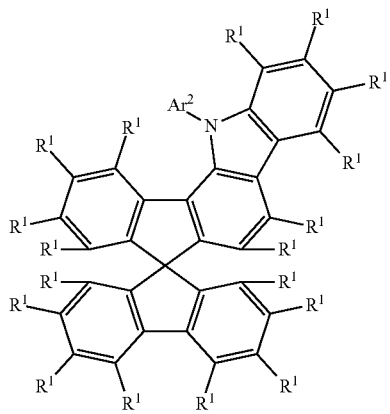

Formula (TA-3)

where Ar² and R¹ have the definitions listed above, especially for formulae (I) and/or (TA-1). Preferred embodiments of the Ar² group are the above-listed structures R¹-1 to R¹-80, more preferably R¹-1 to R¹-51.

A preferred embodiment of the compounds of the formula (TA-3) is the compounds of the following formula (TA-3a):

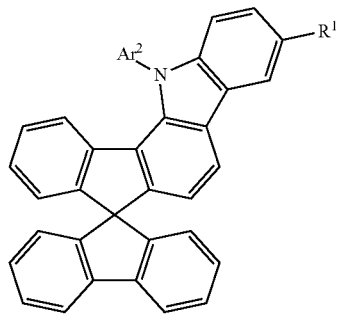

Formula (TA-3a)

where Ar² and R¹ have the definitions listed above, especially for formulae (I) and/or (TA-1). Preferred embodiments of the Ar² group are the above-listed structures R¹-1 to R¹-80, more preferably R¹-1 to R¹-51.

Preferred lactams which are used as co-host materials together with the compounds of the invention are selected from the compounds of the following formula (LAC-1):

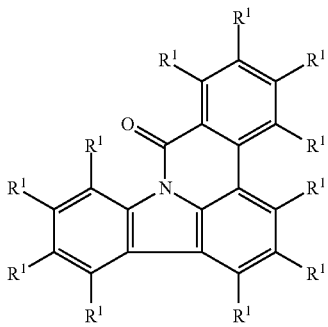

Formula (LAC-1)

where R¹ has the definition listed above, especially for formula (I).

A preferred embodiment of the compounds of the formula (LAC-1) is the compounds of the following formula (LAC-1a):

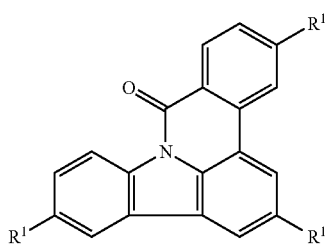

Formula (LAC-1a)

where R¹ has the definition given above, especially for formula (I). R¹ here is preferably the same or different at each instance and is H or an aromatic or heteroaromatic ring system which has 5 to 40 aromatic ring atoms and may be substituted by one or more R² radicals, where R² may have the definition given above, especially for formula (I). Most preferably, the R¹ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic R² radicals, but is preferably unsubstituted. Examples of suitable R¹ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R² radicals, but are preferably unsubstituted. Suitable R¹ structures here are the same structures as depicted above for R-1 to R-79, more preferably R¹-1 to R¹-51.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I), in a preferred embodiment, as matrix material in an emission layer of an organic electronic device, especially in an organic electroluminescent device, for example in an OLED or OLEC. In this case, the matrix material containing compound comprising structures of formula (I) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) or the preferred embodiments recited above and below are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapour deposition. For example, it is possible to apply an emitting layer comprising a compound of the invention comprising structures of formula (I) and a matrix material from solution, and to apply a hole blocker layer and/or an electron transport layer thereto by vapour deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:
1. Electronic devices, especially organic electroluminescent devices, comprising compounds, oligomers, polymers or dendrimers having structures of formula (I) or the preferred embodiments recited above and hereinafter, especially as electron-conducting materials and/or hole conductor materials or as matrix materials, have a very good lifetime.
2. Electronic devices, especially organic electroluminescent devices, comprising compounds, oligomers, polymers or dendrimers having structures of formula (I) or the preferred embodiments recited above and hereinafter, especially as electron transport materials, hole conductor materials and/or as host materials, have excellent efficiency. More particularly, efficiency is much higher compared to analogous compounds containing no structural unit of formula (I). In this context, compounds, oligomers, polymers or dendrimers of the invention having structures of formula (I) or the preferred embodiments recited above and hereinafter bring about a low operating voltage when used in electronic devices. In this context, these compounds especially bring about low roll-off, i.e. a small drop in power efficiency of the device at high luminances.
3. Electronic devices, especially organic electroluminescent devices, comprising compounds, oligomers, polymers or dendrimers having structures of formula (I) or the preferred embodiments recited above and hereinafter, as electron transport materials, hole conductor materials and/or as host materials, have excellent colour purity.
4. The compounds, oligomers, polymers or dendrimers of the invention having structures of formula (I) or the preferred embodiments recited above and hereinafter exhibit very high thermal and photochemical stability and lead to compounds having a very long lifetime.
5. Compounds, oligomers, polymers or dendrimers having structures of formula (I) or the preferred embodiments recited above and below feature excellent thermal stability, and compounds having a molar mass of less than about 1200 g/mol have good sublimability.
6. Compounds, oligomers, polymers or dendrimers having structures of formula (I) or the preferred embodiments recited above and hereinafter have excellent glass film formation.
7. Compounds, oligomers, polymers or dendrimers having structures of formula (I) or the preferred embodiments recited above and hereinafter form very good films from solutions.

These abovementioned advantages are not accompanied by a deterioration in the further electronic properties.

The compounds and mixtures of the invention are suitable for use in an electronic device. An electronic device is understood to mean a device containing at least one layer containing at least one organic compound. The component may also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as host material, hole conductor material, electron injection material and/or electron transport material, preferably as host material and/or electron transport material.

The present invention still further provides an electronic device comprising at least one of the above-detailed compounds or mixtures of the invention. In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices, preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (I) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby. The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The reactants can be sourced from ALDRICH. The numbers for the reactants known from the literature, some of which are stated in square brackets, are the corresponding CAS numbers.

SYNTHESIS EXAMPLES a) (9-Oxo-9H-xanthen-1-yl)urea

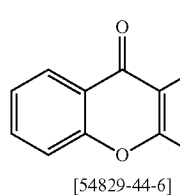

[54829-44-6]

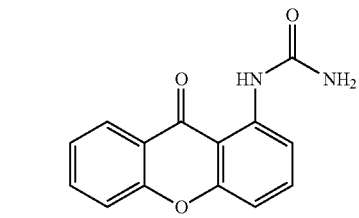

To a degassed solution of 51.1 g (244 mmol) of 1-aminoxanthen-9-one in 1300 ml of AcOH are added 27 g (319 mmol) of KOCN in portions over a period of 5 h at room temperature. The solvent is removed under reduced pressure, then $CH_2Cl_2$ and then water are added. After phase separation, the product is purified by chromatography (90:3, $CH_2Cl_2$/MeOH). Yield: 38 g (150 mmol), 62% of theory; purity: 93% by HPLC.

The following compounds can be prepared in an analogous manner.

| | Reactant 1 | Product | Yield |
|---|---|---|---|
| 1a | [40021-31-6] | | 59% |
| 2a | 96583-32-3] | | 61% |
| 3a | [124557-83-1] | | 60% |
| 4a | [151050-99-6] | | 63% | b) 3H-7-Oxa-1,3-diazabenzo[de]anthracen-2-one

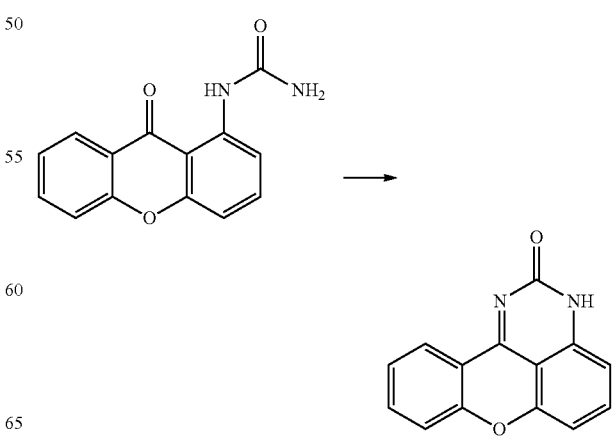

To a solution of 21 g (86 mmol) of (9-oxo-9H-xanthen-1-yl)urea in 1500 ml of EtOH are added 11.7 g (190 mmol) of KOH and the mixture is heated to boiling for 40 min. Cooling is followed by addition of CH$_2$Cl$_2$ to the mixture, which is filtered and admixed with water. Phase separation is followed by recrystallization from acetone. Yield: 17.5 g (74 mmol) of 3H-7-oxa-1,3-diaza-benzo[de]anthracen-2-one, 90% of theory; purity: 93% by HPLC.

The following compounds can be prepared in an analogous manner:

| Reactant 1 | Product | Yield |
|---|---|---|
| 1b | | 87% |
| 2b | | 91% |
| 3b | | 88% |
| 4b | | 87% | c) 2-Chloro-7-oxa-1,3-diazabenzo[de]anthracene

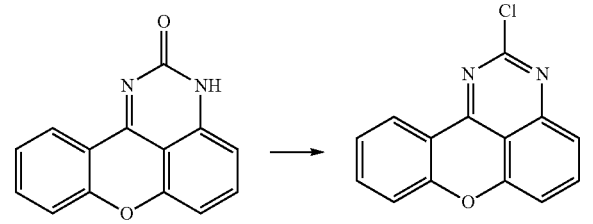 [SMILES: O=c1nc2c3c(cccc3[nH]1)Oc1ccccc1-2 ; Clc1nc2c3c(cccc3n1)Oc1ccccc1-2]

14.1 g (60 mmol) of 3H-7-oxa-1,3-diazabenzo[de]anthracen-2-one are stirred in 200 ml of POCl$_3$ at 85° C. for 5 h. Then the POCl$_3$ is removed under reduced pressure, and the pH is adjusted to 7 by adding 1 N NaOH. Then extraction is effected with CH$_2$Cl$_2$. The solvent is drawn off under reduced pressure, and the product is recrystallized from hexane under protective gas. Yield: 14.7 g (58 mmol), 97% of theory; purity: 93% by HPLC.

The following compounds can be prepared in an analogous manner:

| Reactant 1 | Product | Yield |
|---|---|---|
| 1c | | 87% |
| 2c | | 91% |
| 3c | | 88% |
| 4c | | 87% | d) 2-Chloro-4-(2-methylsulfanylphenyl)quinazoline

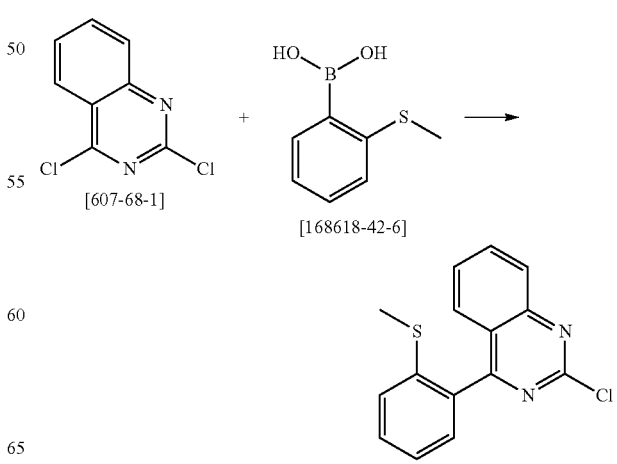

73 g (370 mmol) of 2,4-dichloroquinazoline, 58 g (350 mmol) of 2-methylsulfanylphenylboronic acid and 100 g (475 mmol) of K$_2$CO$_3$ are suspended in 400 ml of THF and 400 ml of water, the mixture is saturated with N$_2$, 1.6 g (1.5 mmol) of tetrakis(triphenylphosphine)palladium(0) are added and the mixture is heated to boiling for 2 h. The mixture is poured into 1 l of a mixture of water/MeOH/6 M HCl 1:1:1, and the beige precipitate is filtered off with suction, washed with water and dried. Yield: 86 g (300 mmol), 82% of theory; purity: 95% by HPLC.

The following compounds can be prepared in an analogous manner:

| | Reactant 1 | Reactant 2 | Product | Yield |
|---|---|---|---|---|
| 1d | 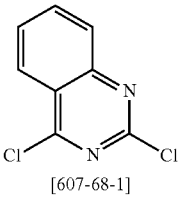 [SMILES: Clc1nc(Cl)c2ccccc2n1] [607-68-1] |  [1072944-21-8] | 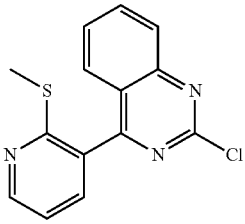 [SMILES: CSc1ncccc1-c1nc(Cl)nc2ccccc12] | 89% |
| 2d | 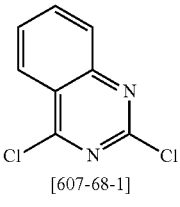 [SMILES: Clc1nc(Cl)c2ccccc2n1] [607-68-1] | 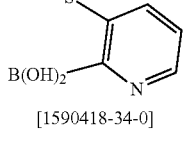 [1590418-34-0] | 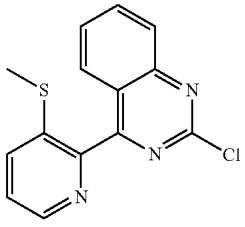 [SMILES: CSc1cccnc1-c1nc(Cl)nc2ccccc12] | 90% |
| 3d | 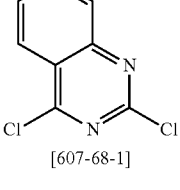 [607-68-1] | 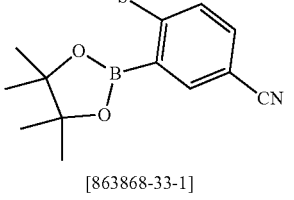 [863868-33-1] | 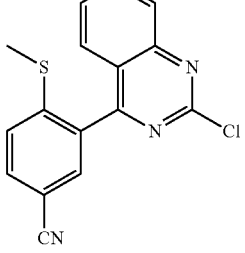 | 91% |
| 4d | 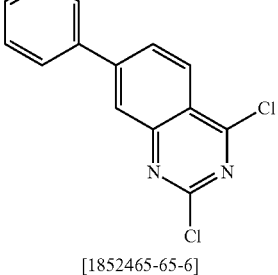 [1852465-65-6] | 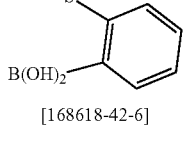 [168618-42-6] | 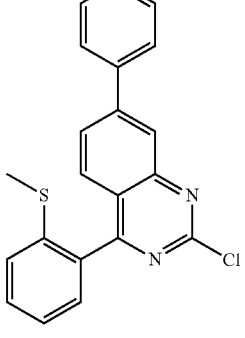 | 92% |
| 5d | 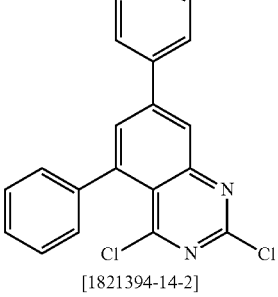 [1821394-14-2] | 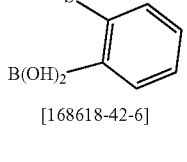 [168618-42-6] | 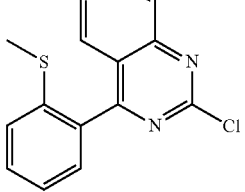 | 95% |

-continued
| | Reactant 1 | Reactant 2 | Product | Yield |
|---|---|---|---|---|
| 6d | 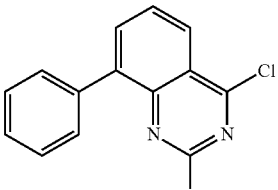 [1152237-20-1] | 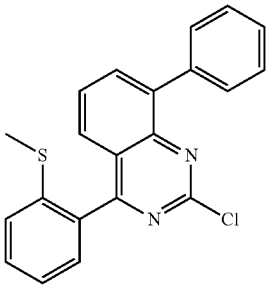 [SMILES: CSc1ccccc1-c1nc(Cl)nc2c(-c3ccccc3)cccc12] [168618-42-6] | 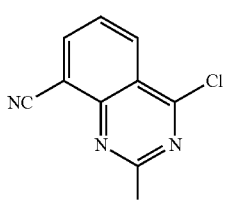 | 91% |
| 7d | 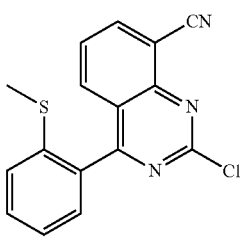 [SMILES: CSc1ccccc1-c1nc(Cl)nc2c(C#N)cccc12] [1150617-71-2] | 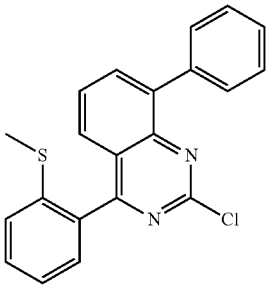 [SMILES: CSc1ccccc1-c1nc(Cl)nc2c(-c3ccccc3)cccc12] [168618-42-6] | 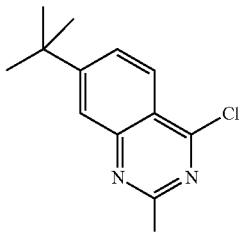 | 90% |
| 8d | 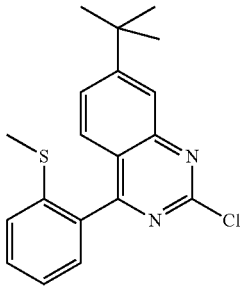 [SMILES: CSc1ccccc1-c1nc(Cl)nc2cc(C(C)(C)C)ccc12] [1093985-82-0] | 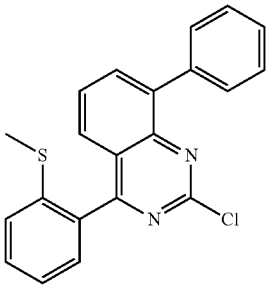 [SMILES: CSc1ccccc1-c1nc(Cl)nc2c(-c3ccccc3)cccc12] [168618-42-6] | 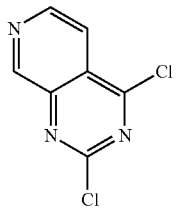 | 87% |
| 9d | 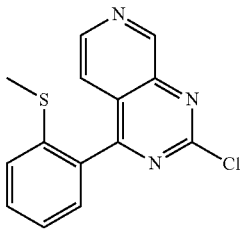 [SMILES: CSc1ccccc1-c1nc(Cl)nc2cnccc12] [908240-50-6] | 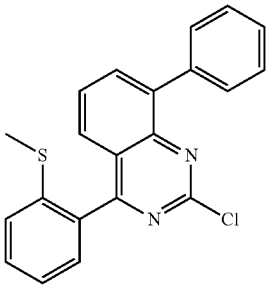 [SMILES: CSc1ccccc1-c1nc(Cl)nc2c(-c3ccccc3)cccc12] [168618-42-6] | 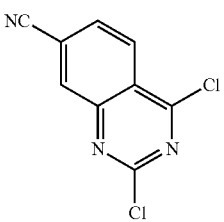 | 95% |
| 10d | 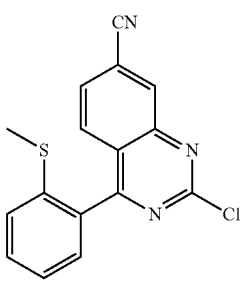 [SMILES: CSc1ccccc1-c1nc(Cl)nc2cc(C#N)ccc12] [864292-40-0] | 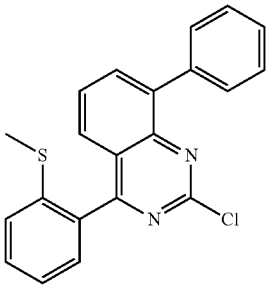 [SMILES: CSc1ccccc1-c1nc(Cl)nc2c(-c3ccccc3)cccc12] [168618-42-6] |  | 85% |

-continued

| | Reactant 1 | Reactant 2 | Product | Yield |
|---|---|---|---|---|
| 11d | 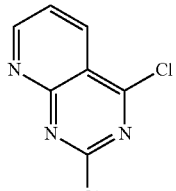 [126728-20-9] | 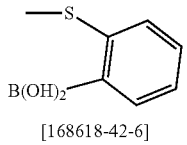 [168618-42-6] | 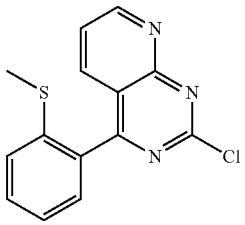 [SMILES: CSc1ccccc1-c1nc(Cl)nc2ncccc12] | 87% |
| 12d | 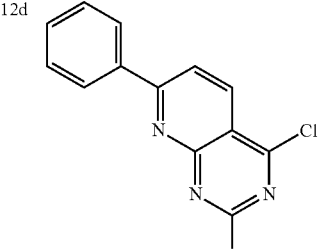 [95845-38-8] | 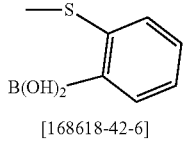 [168618-42-6] | 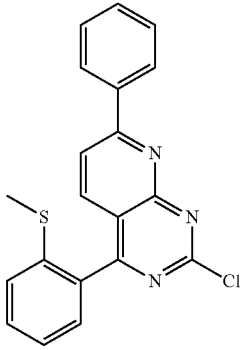 [SMILES: CSc1ccccc1-c1nc(Cl)nc2nc(-c3ccccc3)ccc12] | 91% | e) 2-Chloro-4-(2-methanesulfinylphenyl)quinazoline

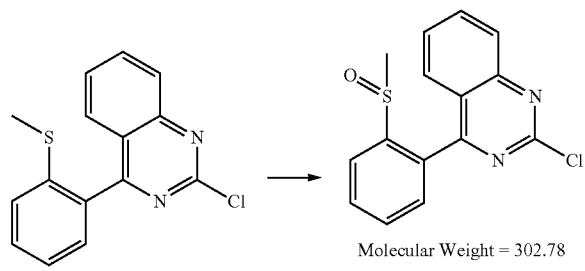

Molecular Weight = 286.79   Molecular Weight = 302.78

Under protective gas, an initial charge of 86 g (300 mmol) of 2-chloro-4-(2-methylsulfanylphenyl)quinazoline in 1.1 l of glacial acetic acid and 125 ml of dichloromethane is cooled to 0° C. To this solution are added dropwise 500 ml (309 mmol) of 30% $H_2O_2$ solution, and the mixture is stirred overnight. The mixture is admixed with $Na_2SO_3$ solution, the phases are separated and the solvent is removed under reduced pressure. Yield: 86 g (285 mmol), 80% of theory; purity: 96% by HPLC.

The following compounds can be prepared in an analogous manner:

| | Reactant 1 | Product | Yield |
|---|---|---|---|
| 1e | 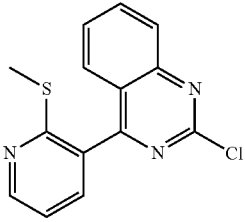 | 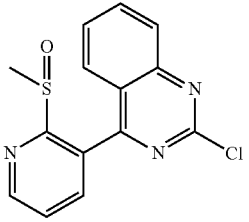 [SMILES: CS(=O)c1ncccc1-c1nc(Cl)nc2ccccc12] | 78% |

-continued

| | Reactant 1 | Product | Yield |
|---|---|---|---|
| 2e | | | 75% |
| 3e | | | 77% |
| 4e | | | 76% |
| 5e | | | 78% |
| 6e | | | 76% |

-continued

| | Reactant 1 | Product | Yield |
|---|---|---|---|
| 7e | | | 68% |
| 8e | | | 88% |
| 9e | | | 82% |
| 10e | | | 84% |
| 11e | | | 80% |

-continued

| Reactant 1 | Product | Yield |
|---|---|---|
| 12e 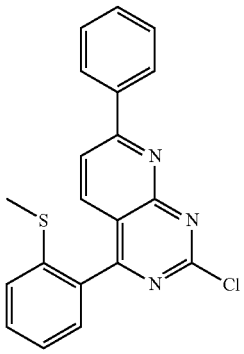 [SMILES: CSc1ccccc1-c1nc(Cl)nc2nc(-c3ccccc3)ccc12] | 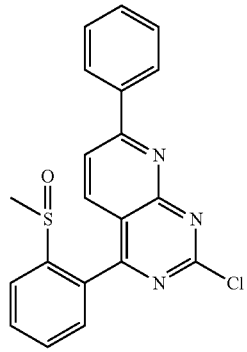 [SMILES: CS(=O)c1ccccc1-c1nc(Cl)nc2nc(-c3ccccc3)ccc12] | 87% |
| 13e 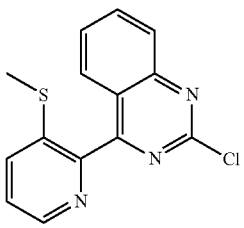 [SMILES: CSc1cccnc1-c1nc(Cl)nc2ccccc12] | 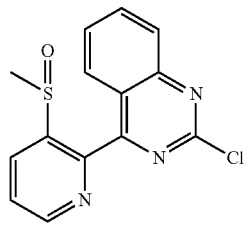 [SMILES: CS(=O)c1cccnc1-c1nc(Cl)nc2ccccc12] | 88% |
| 14e 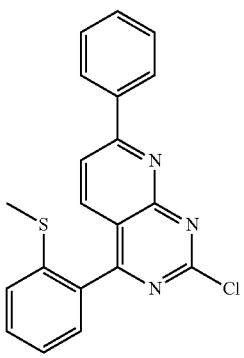 [SMILES: CSc1ccccc1-c1nc(Cl)nc2nc(-c3ccccc3)ccc12] | 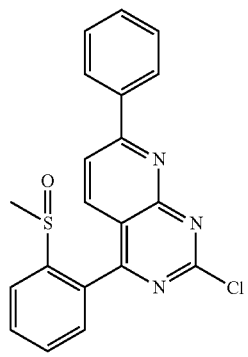 [SMILES: CS(=O)c1ccccc1-c1nc(Cl)nc2nc(-c3ccccc3)ccc12] | | f) 2-Chloro-7-thia-1,3-diazabenzo[de]anthracene

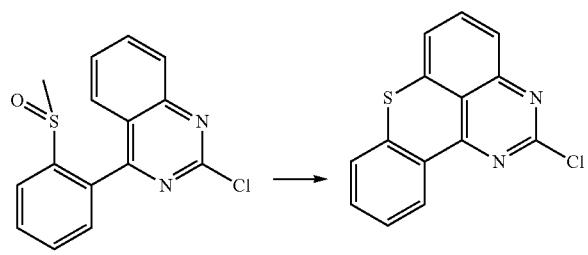 [SMILES: CS(=O)c1ccccc1-c1nc(Cl)nc2ccccc12 ; Clc1nc2c3c(cccc3n1)Sc1ccccc1-2]

A mixture of 85 g (280 mmol) of 2-chloro-4-(2-methanesulfinylphenyl)quinazoline and 737 ml (8329 mmol) of trifluoromethanesulfonic acid is stirred at 5° C. for 48 h. Subsequently, the mixture is admixed with 2.4 l of water/pyridine 5:1 and heated under reflux for 20 min. After cooling to room temperature, 500 ml of water and 1000 ml of dichloromethane are added cautiously. The organic phase is washed with 4×50 ml of $H_2O$ and dried over $MgSO_4$, and the solvents are removed under reduced pressure. The pure product is obtained by recrystallization from toluene. Yield: 72 g (267 mmol), 95% of theory; purity: 95% by HPLC.

The following compounds can be prepared in an analogous manner:

| | Reactant 1 | Product | Yield |
|---|---|---|---|
| 1f | | | 91% |
| 2f | | | 79% |
| 3f | | | 87% |
| 4f | | | 85% |
| 5f | | | 91% |

-continued

| | Reactant 1 | Product | Yield |
|---|---|---|---|
| 6f | | | 87% |
| 7f | | | 89% |
| 8f | | | 92% |
| 9f | | | 85% |
| 10f | | | 87% |

131

-continued

| | Reactant 1 | Product | Yield |
|---|---|---|---|
| 11f | | | 76% |
| 12f | | | 91% |
| 13f | | | 89% | g) 4-(7-Thia-1,3-diazabenzo[de]anthracen-2-yl)-14H-13-thia-14-azabenzo[c]indeno[2,1-a]fluorene

[1313395-18-4]

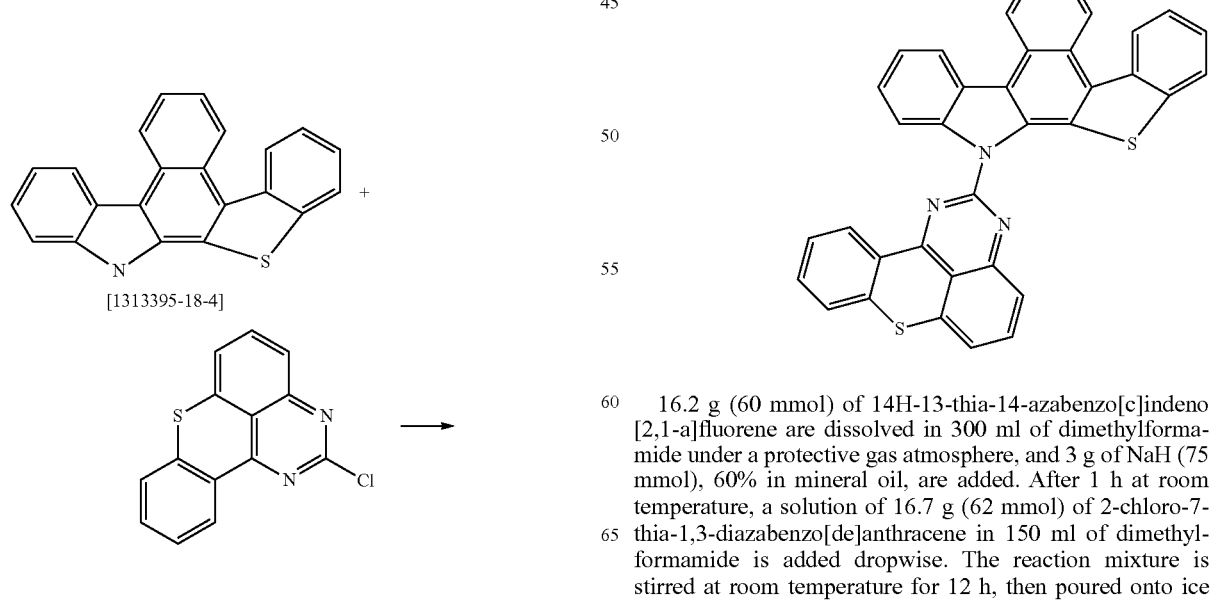

16.2 g (60 mmol) of 14H-13-thia-14-azabenzo[c]indeno[2,1-a]fluorene are dissolved in 300 ml of dimethylformamide under a protective gas atmosphere, and 3 g of NaH (75 mmol), 60% in mineral oil, are added. After 1 h at room temperature, a solution of 16.7 g (62 mmol) of 2-chloro-7-thia-1,3-diazabenzo[de]anthracene in 150 ml of dimethylformamide is added dropwise. The reaction mixture is stirred at room temperature for 12 h, then poured onto ice and extracted three times with dichloromethane. The combined organic phases are dried over $Na_2SO_4$ and concentrated. The residue is recrystallized with toluene and finally fractionally sublimed twice (p about $10^{-6}$ mbar, T=375-390° C.). Yield: 26.7 g (47 mmol), 80% of theory; purity: 99.9% by HPLC.

The following compounds can be prepared in an analogous manner:

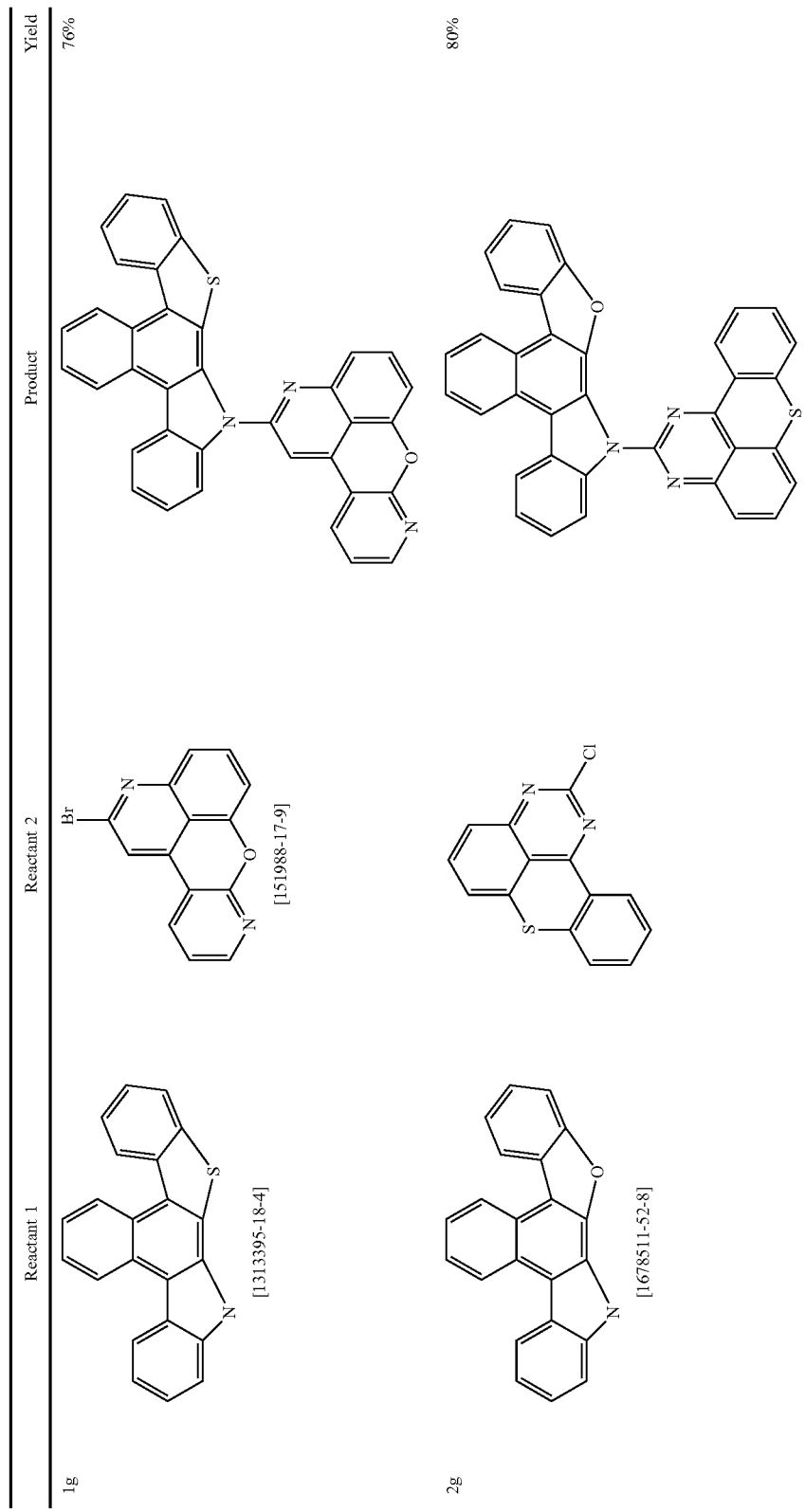

-continued
| | Reactant 1 | Reactant 2 | Product | Yield |
|---|---|---|---|---|
| 3g | 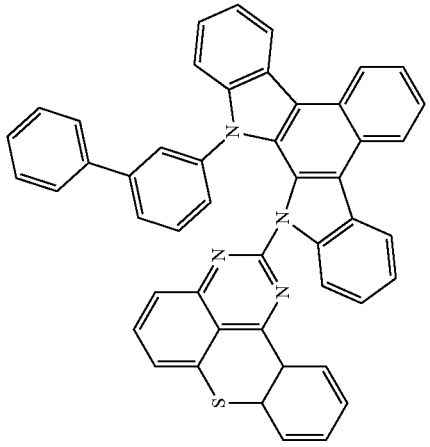 [1639394-10-7] | 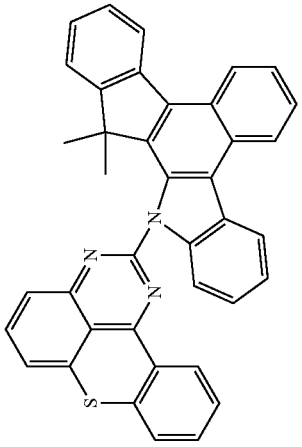 | 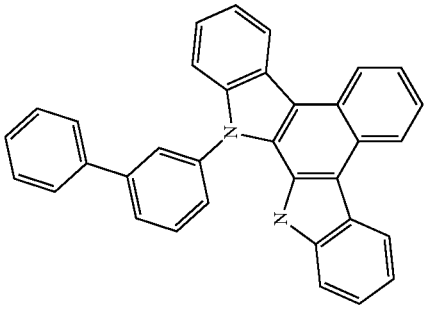 | 86% |
| 4g | 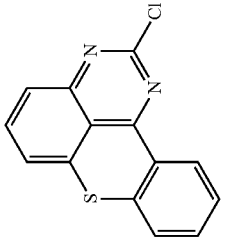 [1447709-49-0] | 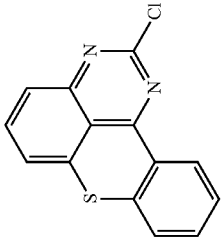 | 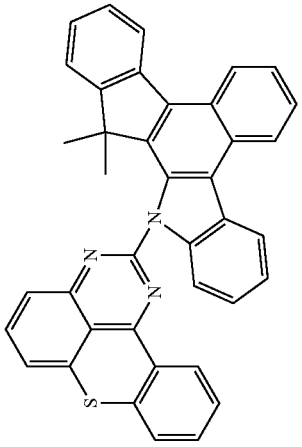 | 81% |

-continued
| | Reactant 1 | Reactant 2 | Product | Yield |
|---|---|---|---|---|
| 5g | 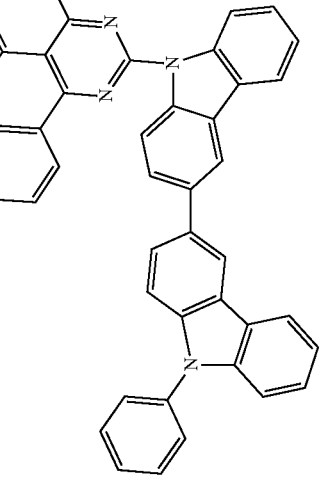 [1345202-03-0] | 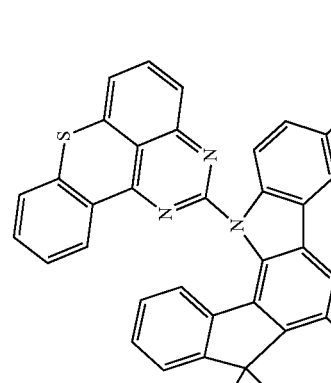 | 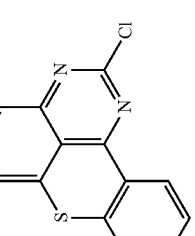 | 82% |
| 6g | 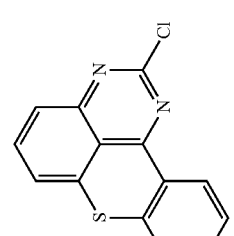 [1447708-58-8] | 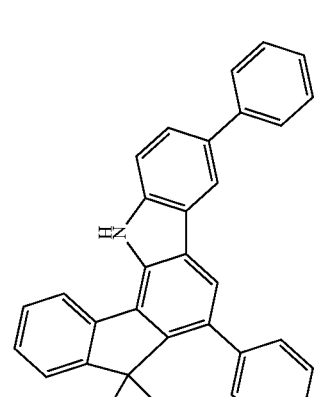 | | 78% |

| | Reactant 1 | Reactant 2 | Product | Yield |
|---|---|---|---|---|
| 7g | [1407183-66-7] | | | 75% |
| 8g | [1257220-47-5] | | | 77% |

| | Reactant 1 | Reactant 2 | Product | Yield |
|---|---|---|---|---|
| 9g | [1373281-72-1] | | | 80% |
| 10g | [1024598-06-8] | | | 84% |

| | Reactant 1 | Reactant 2 | Product | Yield |
|---|---|---|---|---|
| 11g | [1361126-04-6] | | | 89% |
| 12g | [1345202-03-0] | | | 85% |

-continued
| | Reactant 1 | Reactant 2 | Product | Yield |
|---|---|---|---|---|
| 13g | 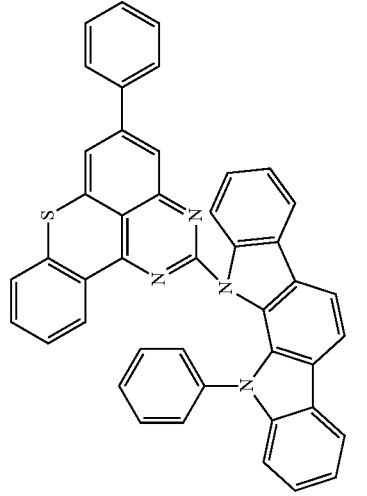 [1024598-06-8] | 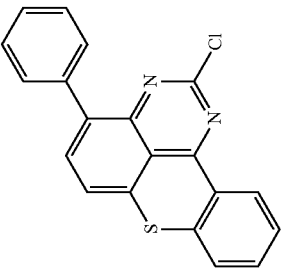 | 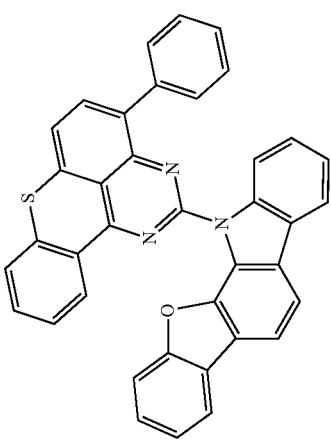 | 84% |
| 14g | 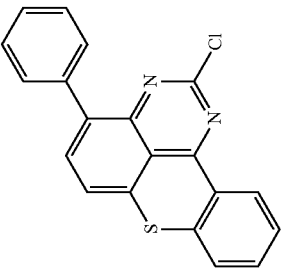 [1338919-70-2] | 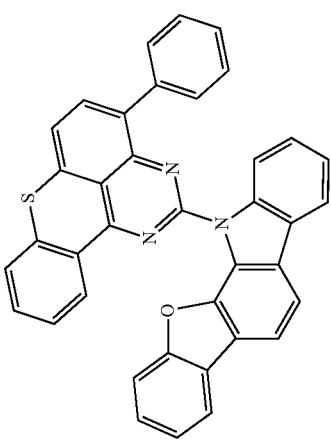 |  | 83% |

| | Reactant 1 | Reactant 2 | Product | Yield |
|---|---|---|---|---|
| 15g | [1373281-72-1] | | | 91% |
| 16g | [953805-18-0] | | | 83% |

| Reactant 1 | Reactant 2 | Product | Yield |
|---|---|---|---|
| 17g [103012-26-6] | | | 85% |
| 18g [1439927-96-4] | | | 84% |

-continued
| | Reactant 1 | Reactant 2 | Product | Yield |
|---|---|---|---|---|
| 19g | 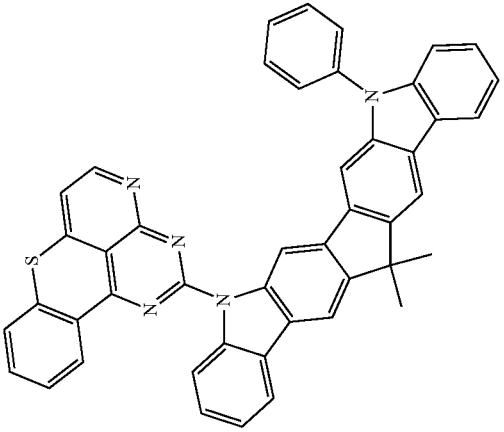 [1439889-64-1] | 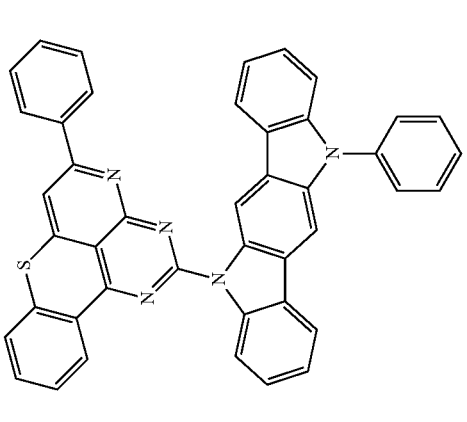 | 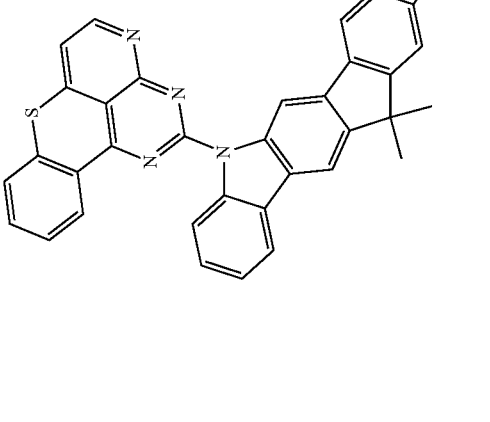 | 73% |
| 20g | 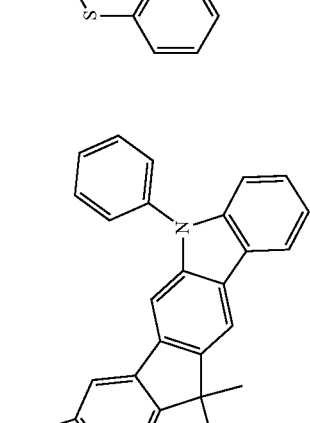 [1316311-27-9] | 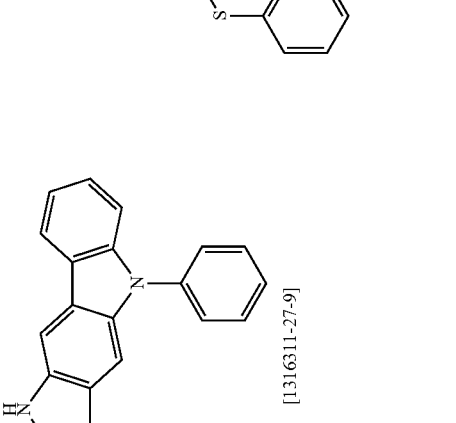 | 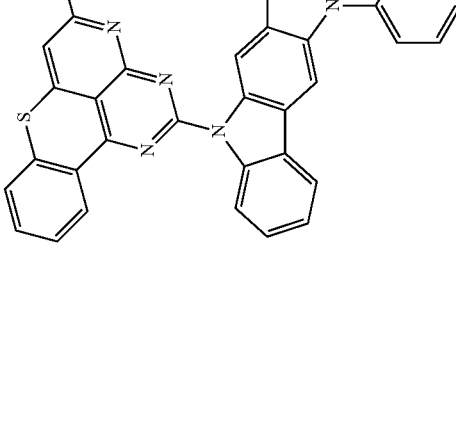 | 74% |

| | Reactant 1 | Reactant 2 | Product | Yield |
|---|---|---|---|---|
| 21g | [1257246-14-8] | | | 81% |
| 22g | [1361126-04-6] | | | 85% |

| | Reactant 1 | Reactant 2 | Product | Yield |
|---|---|---|---|---|
| 23g | 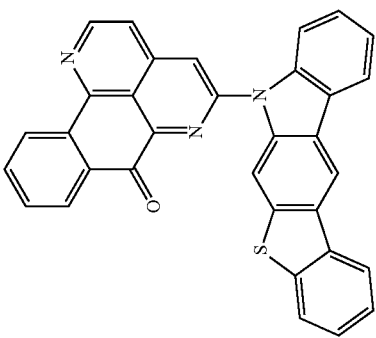 [1255309-04-6] | 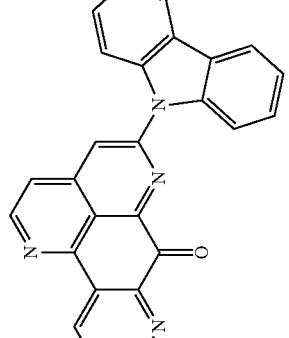 [760976-86-1] | 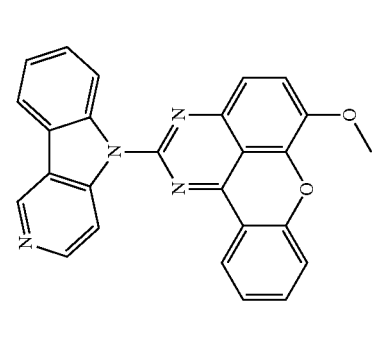 | 77% |
| 24g | 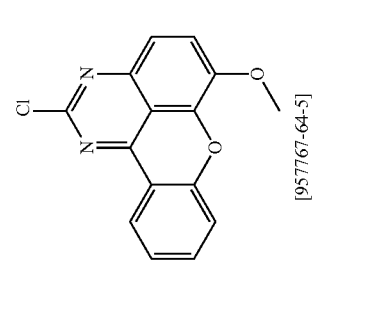 [96-74-8] | 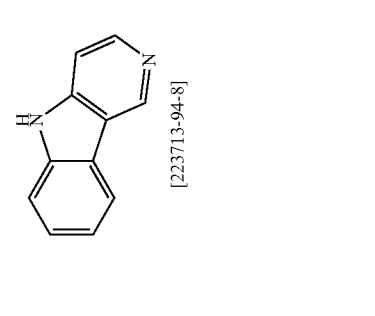 [741281-31-2] | | 87% |
| 25g | 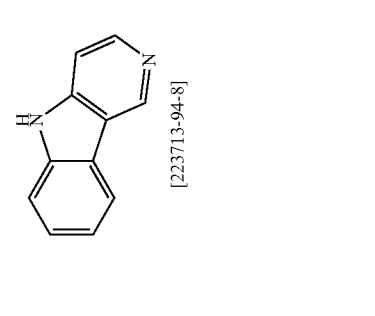 [2237713-94-8] | [957767-64-5] | | 88% |

| | Reactant 1 | Reactant 2 | Product | Yield |
|---|---|---|---|---|
| 26g | WO 2010/136109 | [853924-93-3] | | 76% |
| 27g | WO 2010/136109 | [348616-78-4] | | 75% |

-continued

| | Reactant 1 | Reactant 2 | Product | Yield |
|---|---|---|---|---|
| 28g | WO 2010/136109 | [159181-73-4] | | 76% |
| 29g | [1345202-03-0] | [159181-72-3] | | 77% |
| 30g | [1345202-03-0] | [151051-08-0] | | 80% |

| | Reactant 1 | Reactant 2 | Product | Yield |
|---|---|---|---|---|
| 31g | [1345202-03-0] | [151988-17-9] | | 72% |
| 32g | [1345202-03-0] | | | 70% |
| 33g | [1313395-18-4] | [59500-27-5] | | 73% |

-continued

| Reactant 1 | Reactant 2 | Product | Yield |
|---|---|---|---|
| 34g [1345202-03-0] | | | 69% |
| 35g [1345202-03-0] | [59500-27-5] | | 87% |

| | Reactant 1 | Reactant 2 | Product | Yield |
|---|---|---|---|---|
| 36g | 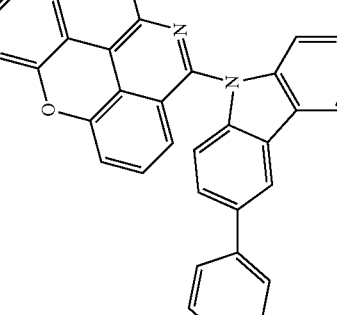 [1345202-03-0] | 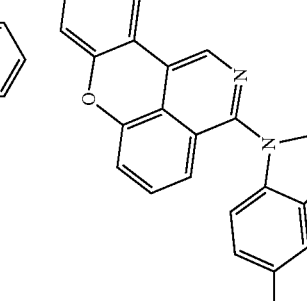 [72240-51-8] | 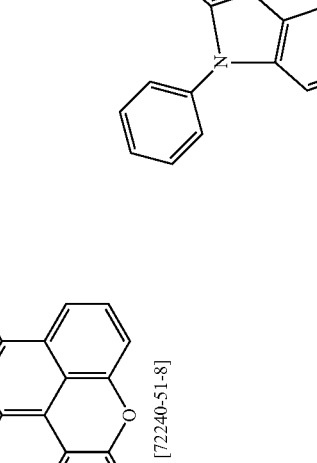 | 72% |
| 37g | 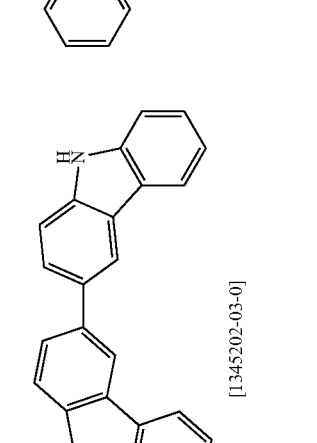 [1345202-03-0] | 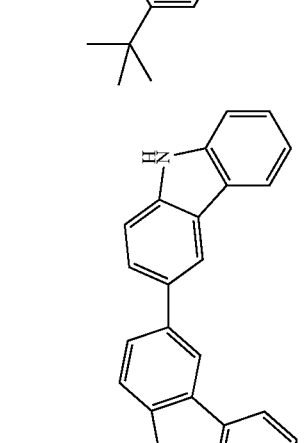 [59500-40-2] | 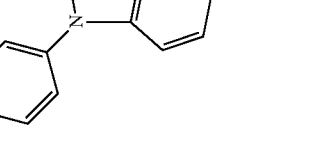 | 70% |

| Reactant 1 | Reactant 2 | Product | Yield |
|---|---|---|---|
| 38g | [59500-30-0] | | 81% |
| 39g | [1025849-63-1] | | 78% |
| 40g | [348616-78-4] | | 76% |
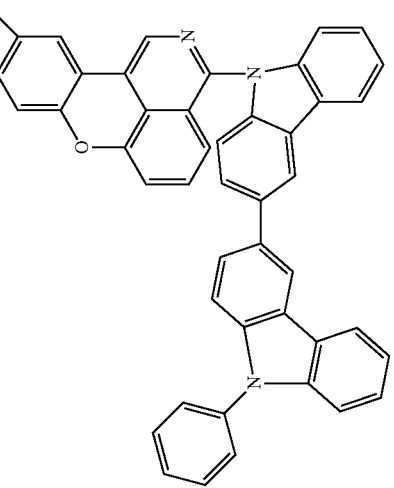

| | Reactant 1 | Reactant 2 | Product | Yield |
|---|---|---|---|---|
| 41g | 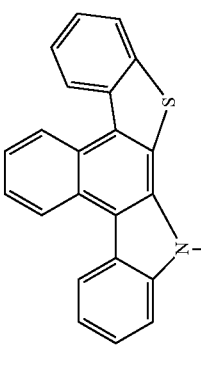 [1313395-18-4] | 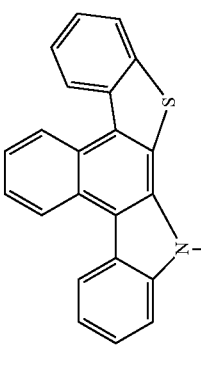 [348616-78-4] | 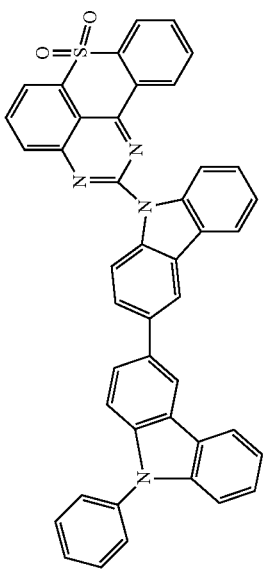 | 77% |
| 42g | 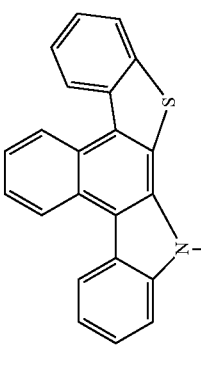 [1345202-03-0] | 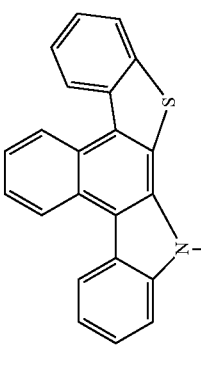 | 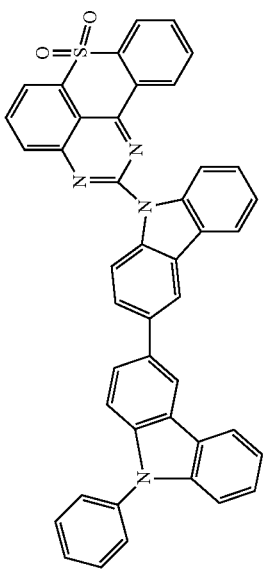 | 71% |
| 43g | 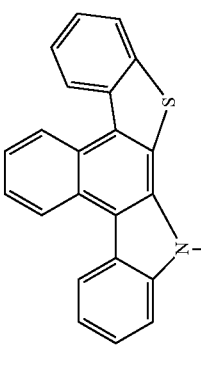 [1345202-03-0] | 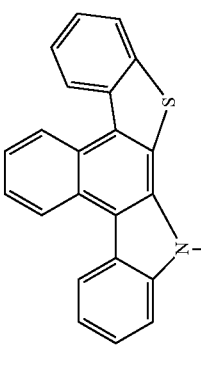 | 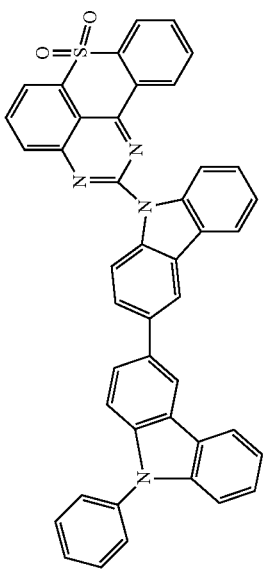 | 69% |

-continued

| Reactant 1 | Reactant 2 | Product | Yield |
|---|---|---|---|
| 44g [1345202-03-0] | | | 60% |
| 45g [1345202-03-0] | | | 74% |
| 46g [1345202-03-0] | | | 72% |

-continued

| Reactant 1 | Reactant 2 | Product | Yield |
|---|---|---|---|
| 47g [1615703-28-0] | | | 70% |
| 48g [1616231-39-0] | | | 67% |

Production of the OLEDs

Examples I1 to I8 which follow (see Table 1) present the use of the materials of the invention in OLEDs.

Pretreatment for Examples I1 to I8:

Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 2.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC2:TER1 (50%:45%:5%) mean here that the material IC1 is present in the layer in a proportion by volume of 50%, IC2 in a proportion of 45% and TER1 in a proportion of 5%. Analogously, the electron transport layer may also consist of a mixture of two materials.

The OLEDs are characterized in a standard manner. The electroluminescence spectra are determined at a luminance of 1000 cd/m$^2$, and the CIE 1931 x and y colour coordinates are calculated therefrom.

Use of Mixtures of the Invention in OLEDs

The materials of the invention can be used in the emission layer in phosphorescent red OLEDs. The inventive compounds EG1 to EG6 are used in Examples 11 to 18 as matrix material in the emission layer. The colour coordinates of the electroluminescence spectra of the OLEDs are CIEx=0.67 and CIEy=0.33. The materials are thus suitable for use in the emission layer of red-phosphorescing OLEDs.

In addition, the materials of the invention can be used successfully in the hole blocker layer (HBL) or electron blocker layer (EBL). This is shown in Examples 17 and 18. Here too, the colour coordinates of the spectrum of the OLED are CIEx=0.67 and CIEy=0.33.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| I1 | HATCN 5 nm | SpMA1 125 nm | SpMA2 10 nm | IC2:EG1:TER1 (50%:45%:5%) 40 nm | — | ST1:LiQ (50%:50%) 35 nm | — |
| I2 | HATCN 5 nm | SpMA1 125 nm | SpMA2 10 nm | EG2:TER1 (95%:5%) 40 nm | — | ST1:LiQ (50%:50%) 35 nm | — |
| I3 | HATCN 5 nm | SpMA1 125 nm | SpMA2 10 nm | IC1:EG3:TER1 (50%:45%:5%) 40 nm | — | ST1:LiQ (50%:50%) 35 nm | — |
| I4 | HATCN 5 nm | SpMA1 125 nm | SpMA2 10 nm | EG4:TER1 (95%:5%) 40 nm | — | ST1:LiQ (50%:50%) 35 nm | — |
| I5 | HATCN 5 nm | SpMA1 125 nm | SpMA2 10 nm | IC2:EG5:TER1 (50%:45%:5%) 40 nm | — | ST1:LiQ (50%:50%) 35 nm | — |
| I6 | HATCN 5 nm | SpMA1 125 nm | SpMA2 10 nm | IC2:EG6:TER1 (50%:45%:5%) 40 nm | — | ST1:LiQ (50%:50%) 35 nm | — |
| I7 | HATCN 5 nm | SpMA1 125 nm | SpMA2 10 nm | EG4:TER1 (95%:5%) 40 nm | EG4 5 nm | ST1:LiQ (50%:50%) 30 nm | — |
| I8 | HATCN 5 nm | SpMA1 125 nm | EG4 10 nm | EG4:TER1 (95%:5%) 40 nm | — | ST1:LiQ (50%:50%) 35 nm | — |

TABLE 2

Structural formulae of the materials for the OLEDs

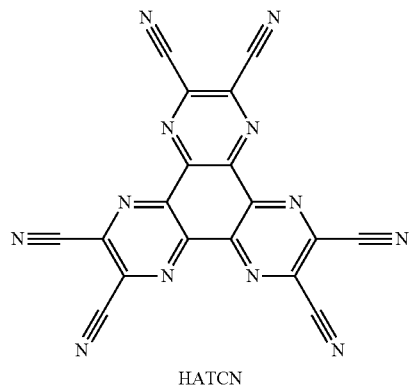

HATCN

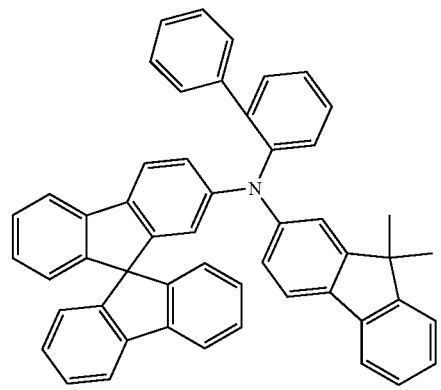

SpMA1

TABLE 2-continued
Structural formulae of the materials for the OLEDs
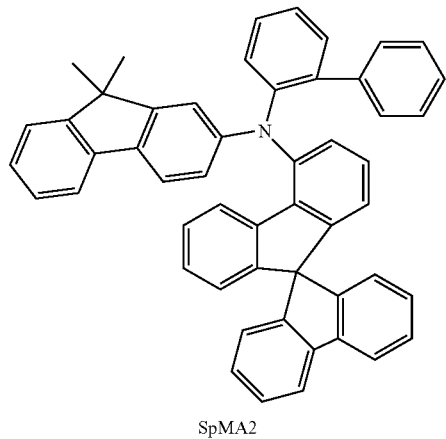 [SMILES: CC1(C)c2ccccc2-c2ccc(N(c3ccccc3-c3ccccc3)c3cccc4c3-c3ccccc3C43c4ccccc4-c4ccccc43)cc21]
SpMA2
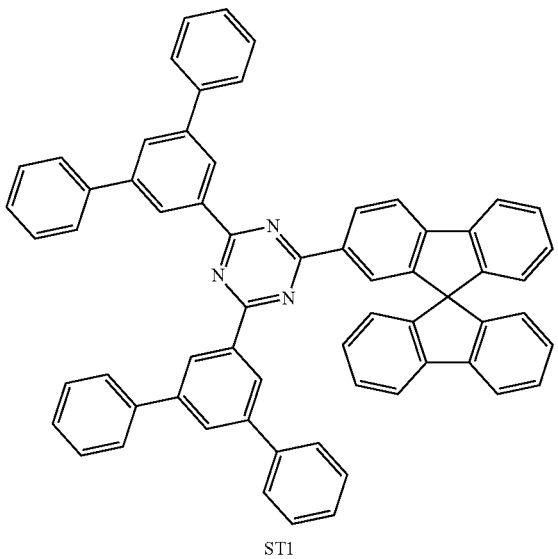
ST1
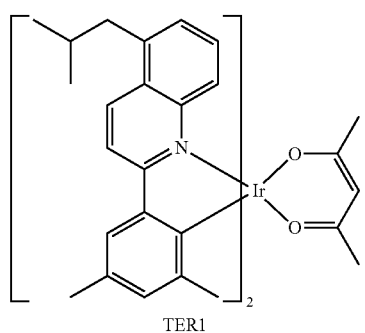
TER1
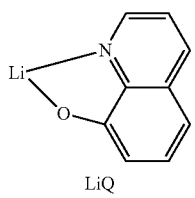
LiQ
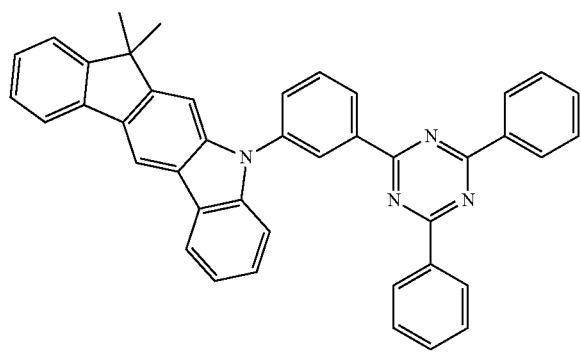
IC1
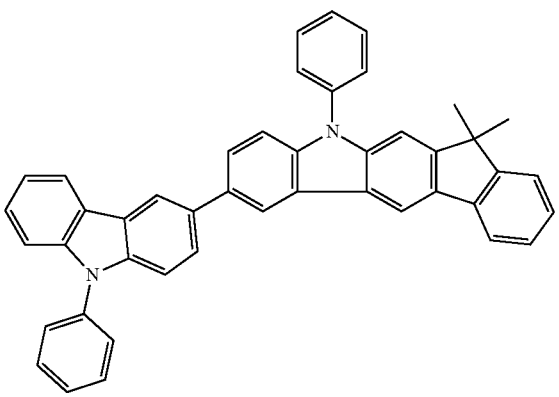
IC2

TABLE 2-continued
Structural formulae of the materials for the OLEDs
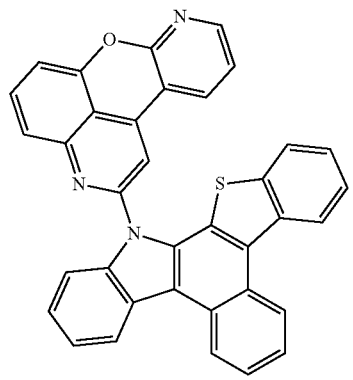
EG1
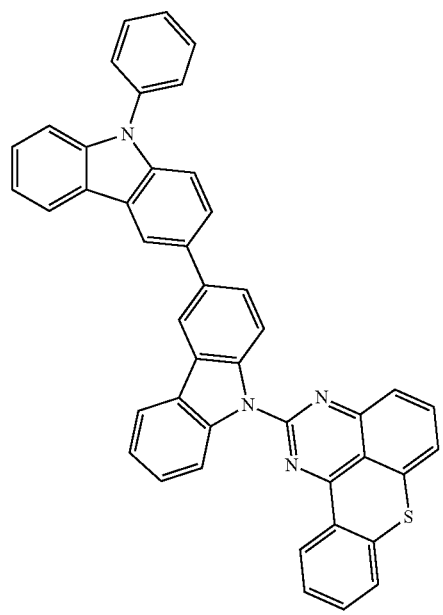
EG2
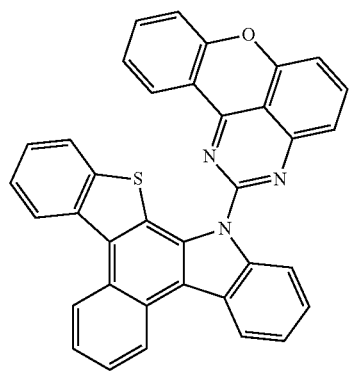
EG3
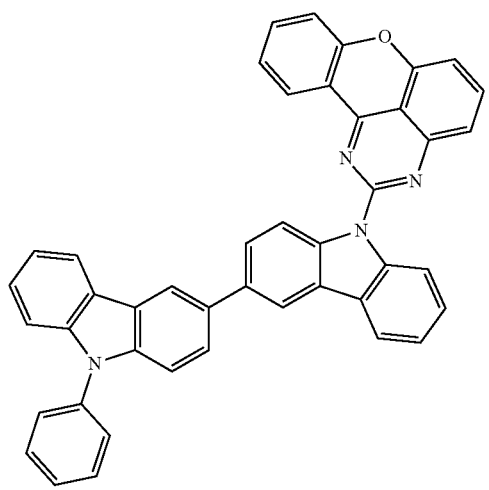
EG4
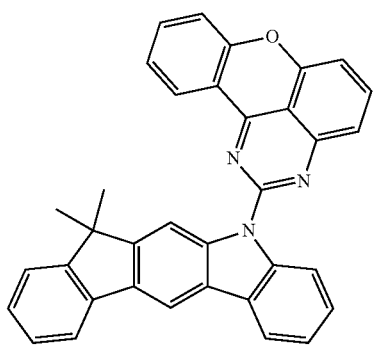
EG5
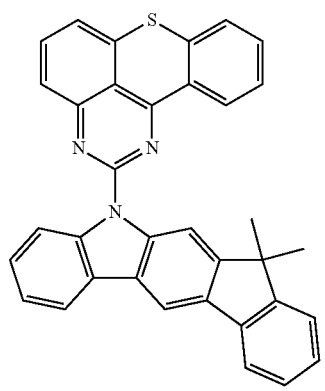
EG6

The invention claimed is:
1. Compound comprising at least one structure of the (IIIa), (IIIb), (IIIc) or (IIId)

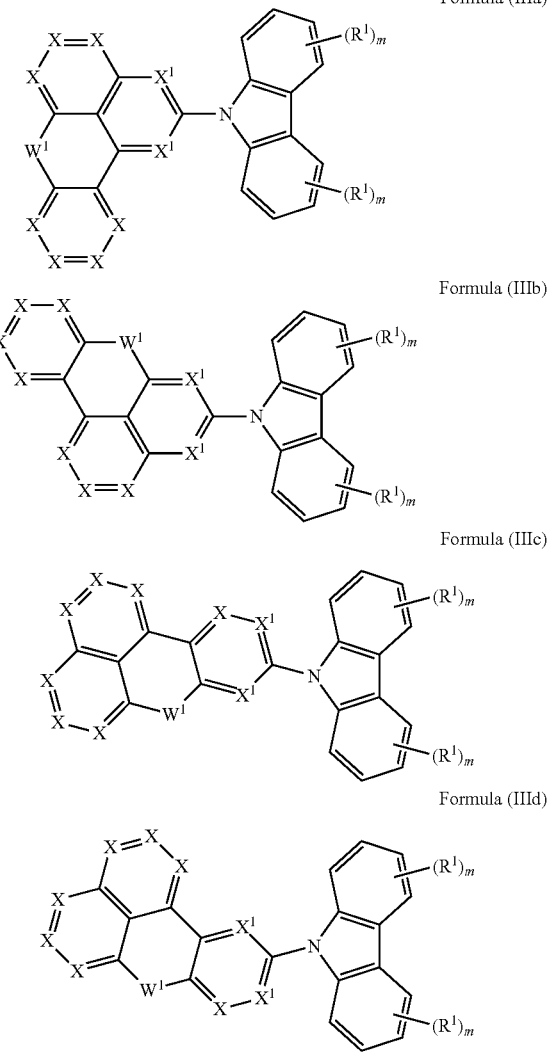

Formula (IIIa)

Formula (IIIb)

Formula (IIIc)

Formula (IIId)

where in Formula (IIIa), (IIIb), (IIIc), and (IIId) $W^1$ is SO, $SO_2$, $Si(R^1)_2$ or C=O;
where in Formulae (IIIa), (IIIb), (IIIc), and (IIId), the symbols used are as follows:
X is the same or different at each instance and is N or $CR^1$;
$X^1$ is N or $CR^1$ where at least one $X^1$ group is N;
$R^1$ is the same or different at each instance and is H, D, F, Cl, Br, I, CN, $NO_2$, $OAr^1OR^2$, $SAr^1$, $SR^2$, C(=O) $Ar^1$, C(=O)$R^2$, P(=O)($Ar^1$)$_2$, P($Ar^1$)$_2$, B($Ar^1$)$_2$, Si($Ar^1$)$_3$, Si($R^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, and where one or more nonadjacent $CH_2$ groups may be replaced by -$R^2$C=C$R^2$-, —C≡C—, Si($R^2$)$_2$, C=O, C=S, C=N$R^2$, —C(=O)O—, —C(=O) N$R^2$—, N$R^2$, P(=O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals; at the same time, two or more R' substituents together may also form a mono- or polycyclic, aliphatic, heteroaliphatic, aromatic or heteroaromatic ring system with the proviso that a substituent $R^1$ does not form a ring system with a substituent $R^2$;
$Ar^1$ is the same or different at each instance and is an aromatic or heteroaromatic ring system which has 5 to 30 aromatic ring atoms and may be substituted by one or more nonaromatic $R^2$ radicals; at the same time, it is possible for two $Ar^1$ radicals bonded to the same silicon atom, nitrogen atom, phosphorus atom or boron atom also to be joined together via a bridge by a single bond or a bridge selected from B($R^2$), C($R^2$)$_2$, Si($R^2$)$_2$, C=O, C=N$R^2$, C=C($R^2$)$_2$, O, S, S=O, $SO_2$, N($R^2$), P($R^2$) and P(=O)$R^2$;
$R^2$ is the same or different at each instance and is H, D, F, Cl, Br, I, CN, B(O$R^3$)$_2$, O$R^3$, S$R^3$, $NO_2$, C(=O)$R^3$, C$R^3$=C($R^3$)$_2$, C(=O)O$R^3$, C(=O)N($R^3$)$_2$, Si($R^3$)$_3$, P($R^3$)$_2$, B($R^{13}$)$_2$, N($R^3$)$_2$, $NO_2$, P(=O)($R^3$)$_2$, $OSO_2R^3$, O$R^3$, S(=O) $R^3$, S(=O)$_2R^3$, straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, and where one or more nonadjacent $CH_2$ groups may be replaced by -$R^3$C=C$R^3$-, —C≡C—, Si($R^3$)$_2$, C=O, C=S, C=N$R^3$, —C(=O)O—, —C(=O)N$R^3$, N$R^3$, P(=O) ($R^3$), —O—, —S—, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^3$ radicals, or an aryloxy or heteroaryloxy group which has 5 to 40 aromatic ring atoms and may be substituted by one or more $R^3$ radicals; at the same time, two or more $R^2$ substituents together may also form a mono- or polycyclic, aliphatic, heteroaliphatic, aromatic or heteroaromatic ring system with the proviso that a substituent $R^2$ does not form a ring system with a substituent $R^1$;
$R^3$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more $R^3$ substituents together to form a mono- or polycyclic, aliphatic ring system;
where m is 4;
wherein, if two adjacent substituents $R^1$ form an aromatic or heteroaromatic ring system, at least one such ring system is selected from the groups of formula (DB-1)

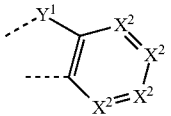

Formula (DB-1)

where $X^2$ is the same or different at each instance and is N or $CR^2$, $Y^1$ is O, S, $C(R^2)_2$, or $NR^2$ and the dotted lines represent direct bonds to the formula (IIIa), (IIIb), (IIIc), or (IIId);

wherein if $Y^1$ in DB-1 is $C(R^2)_2$, the $R^2$ in the $C(R^2)_2$, in DB-1 does not form a mono- or polycyclic, aliphatic, heteroaliphatic, aromatic or heteroaromatic ring system.

2. Compound according to claim 1, comprising at least one structure of the formula (IVa), (IVb), (IVc) or (IVd)

Formula (IVa)
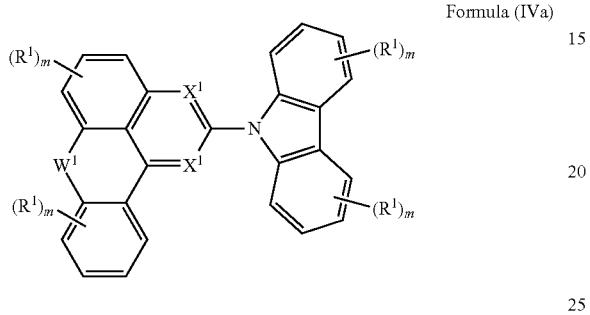

Formula (IVb)
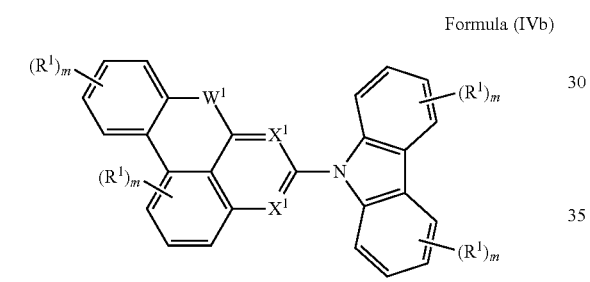

Formula (IVc)
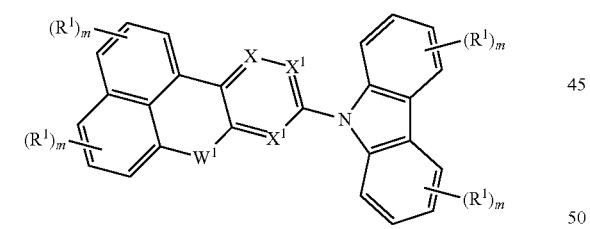

Formula (IVd)
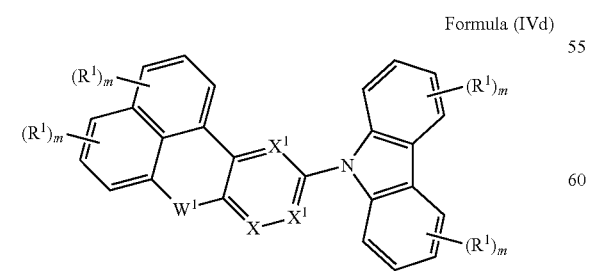

wherein m is 4, n is 3, and $X^1$ is N or $CR^1$ where at least one $X^1$ group is N.

3. Compound according to claim 2, comprising at least one structure of the formula (Va), (Vb), (Vc) or (Vd)

Formula (Va)
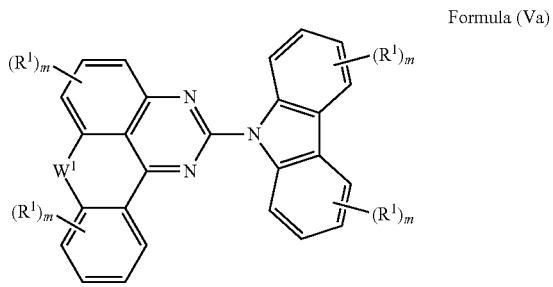

Formula (Vb)
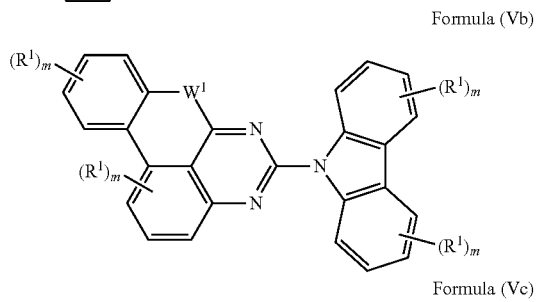

Formula (Vc)
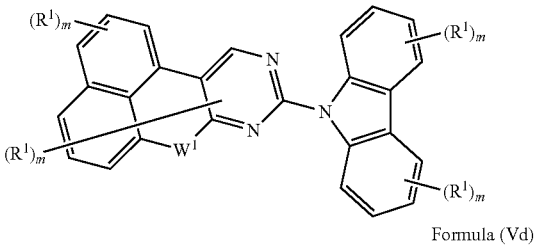

Formula (Vd)
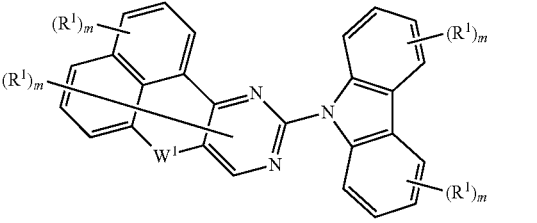

where m is 4, and n is 3.

4. Compound according to claim 1, characterized in that two adjacent $R^1$ radicals form a ring of the formula (DB-1) and optionally two adjacent $R^1$ form a ring of formula (DB-2) or (DB-3)

Formula (DB-2)

Formula (DB-3)

where $X^2$ is the same or different at each instance and is N or $CR^2$, $Y^1$ and $Y^2$ independently at each instance are O, S, (CR²)₂ or NR² and the dotted lines represent bonds to the formula (IIIa), (IIIb), (IIIc), or (IIId), where X¹ and R² have the definition given in claim 1.

5. Compound according to claim 4, comprising at least one structure of the formula (VIa), (VIb), (VIc) or (VId)

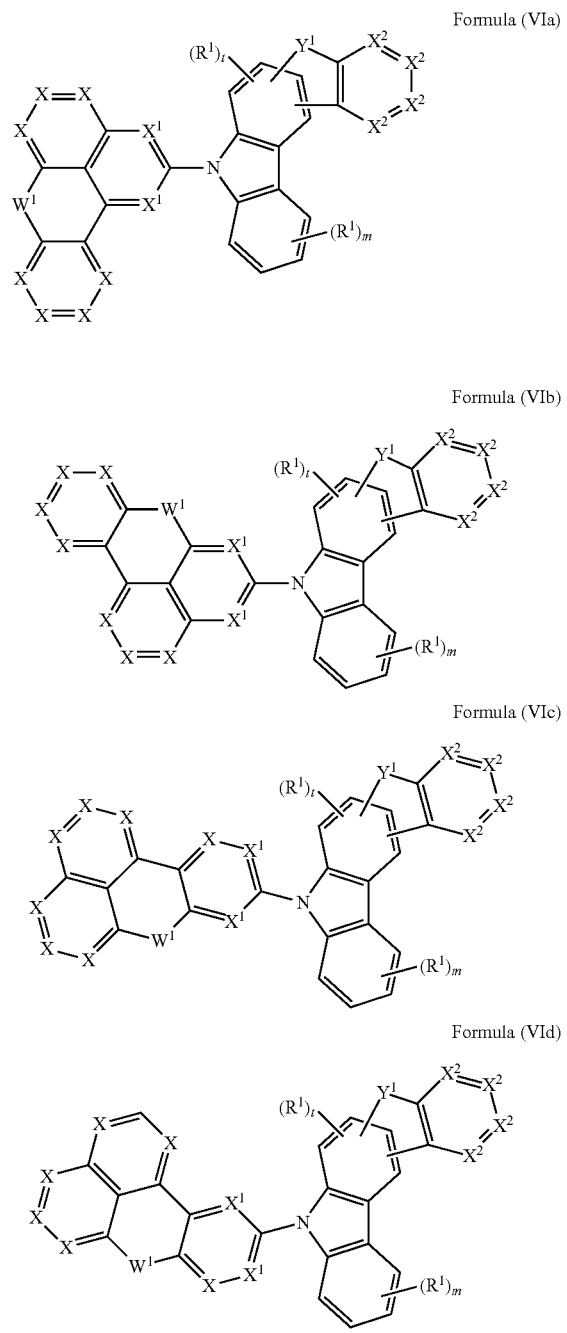

Formula (VIa)

Formula (VIb)

Formula (VIc)

Formula (VId)

where the symbols X¹ and X² have the definition given in claim 4, l is 2, m is 4 and X¹ is N or CR¹, where at least one X¹ group adjacent to the carbon atom to which the carbazole derivative group is bonded is N.

6. Compound according to claim 5, comprising at least one structure of the formula (VIIa), (VIIb), (VIIc), (VIId), (XIIIa), (XIIIb), (XIIIc) or (XIIId)

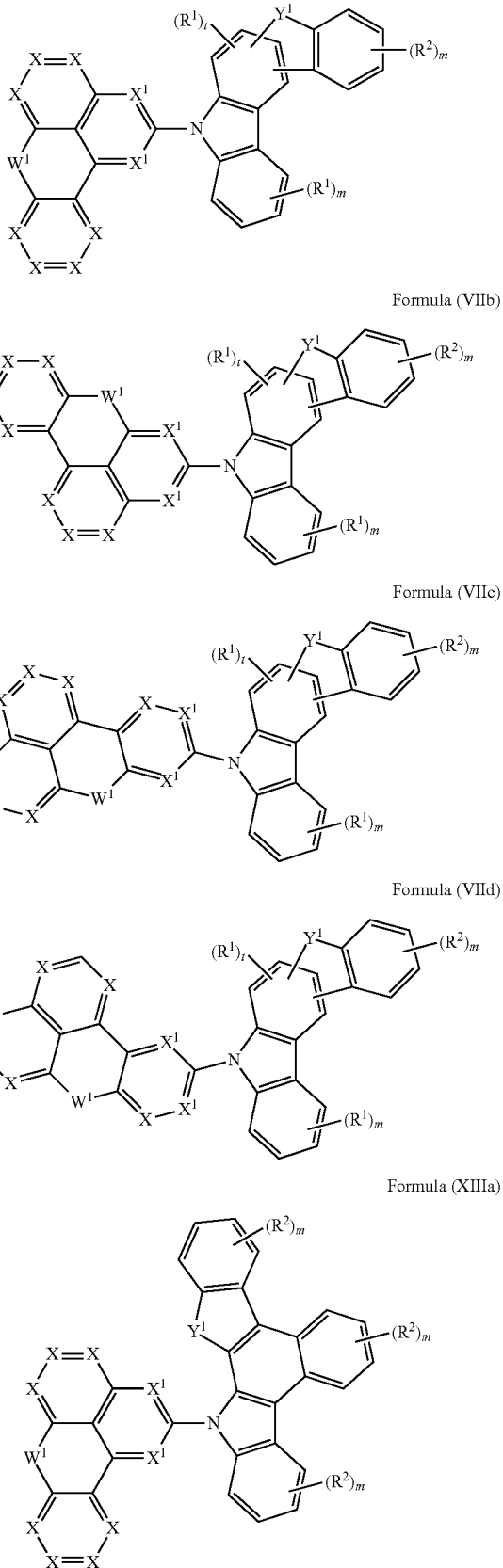

Formula (VIIa)

Formula (VIIb)

Formula (VIIc)

Formula (VIId)

Formula (XIIIa)

Formula (XIIIb)
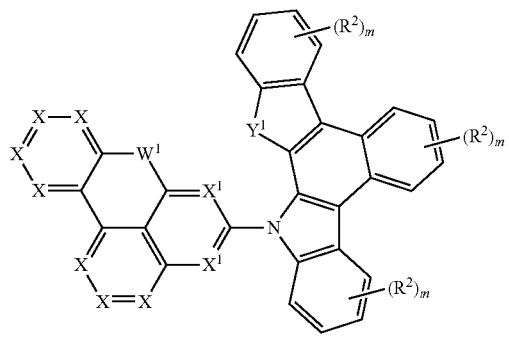
Formula (XIIIc)
Formula (XIIId)
where m is 4, and $X^1$ is N or $CR^1$, where at least one $X^1$ group is N.
7. Compound according to claim 6, comprising at least one structure of the formula (VIIIa), (VIIIb), (VIIIc), (VIIId), (XIVa), (XIVb), (XIVc) or (XIVd)
Formula (VIIIa)
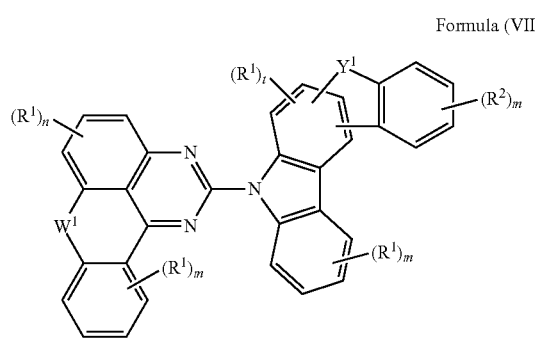
Formula (VIIIb)
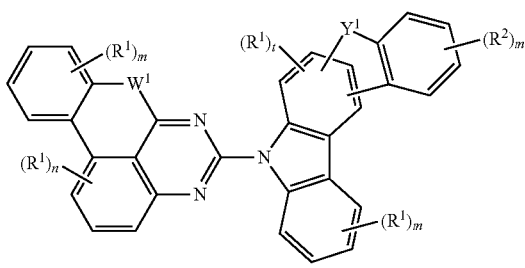
Formula (VIIIc)
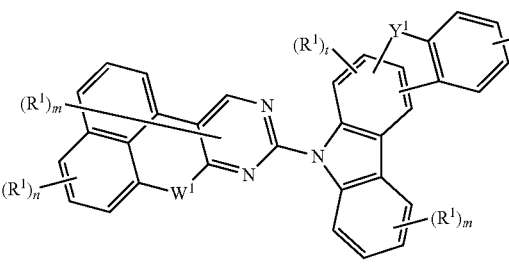
Formula (VIIId)
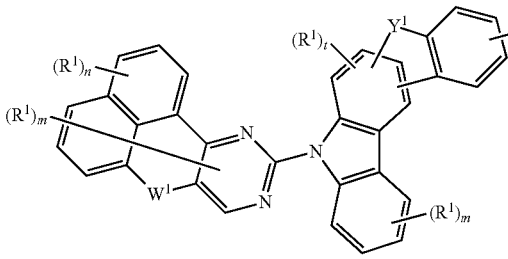
Formula (XIVa)
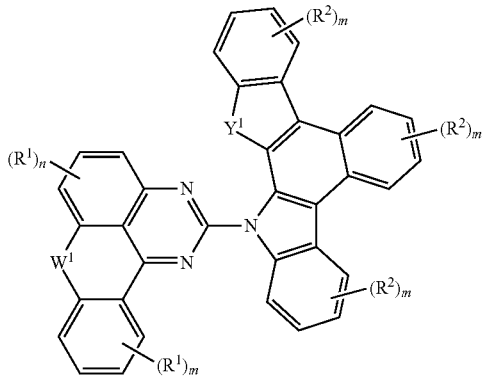
Formula (XIVb)
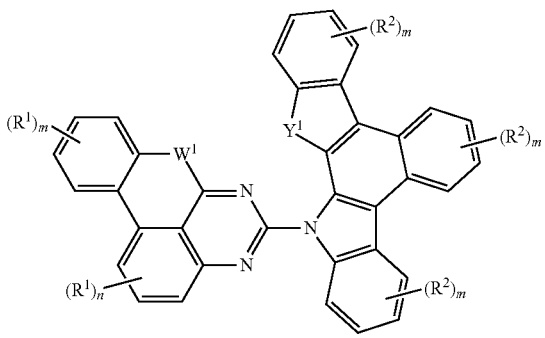

-continued

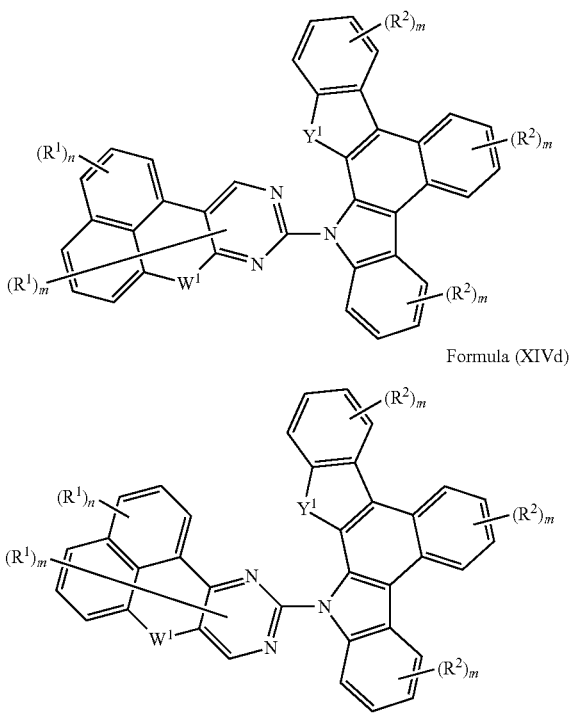

Formula (XIVc)

Formula (XIVd)

where l is 2, n is 3 and m is 4.

8. Compound according to claim 1, characterized in that not more than four X groups are N.

9. Composition comprising at least one compound according to claim 1 and at least one further compound selected from the group consisting of fluorescent emitters, phosphorescent emitters, emitters that exhibit TADF, host materials, electron transport materials, electron injection materials, hole conductor materials, hole injection materials, electron blocker materials and hole blocker materials.

10. Formulation comprising at least one compound according to claim 1 and at least one solvent.

11. Use of a compound according to claim 1, in an electronic device.

12. Process for preparing a compound according to claim 1, characterized in that, in a coupling reaction, a compound comprising at least one nitrogen-containing heterocyclic group is joined a compound comprising at least one carbazole group.

13. Electronic device comprising at least one compound according to claim 1, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells and organic laser diodes.

* * * * *